(12) United States Patent
Ginggen et al.

(10) Patent No.: US 11,324,534 B2
(45) Date of Patent: May 10, 2022

(54) DEVICES AND METHODS FOR ABLATION OF THE SKIN

(71) Applicant: Cytrellis Biosystems, Inc., Woburn, MA (US)

(72) Inventors: Alec Ginggen, Plymouth, MA (US); Douglas Levinson, Sherborn, MA (US)

(73) Assignee: Cytrellis Biosystems, Inc., Woburn, MA (US)

(*) Notice: Subject to any disclaimer, the term of this patent is extended or adjusted under 35 U.S.C. 154(b) by 632 days.

(21) Appl. No.: 15/526,299

(22) PCT Filed: Nov. 13, 2015

(86) PCT No.: PCT/US2015/060685
§ 371 (c)(1),
(2) Date: May 11, 2017

(87) PCT Pub. No.: WO2016/077759
PCT Pub. Date: May 19, 2016

(65) Prior Publication Data
US 2017/0367729 A1   Dec. 28, 2017

Related U.S. Application Data

(60) Provisional application No. 62/079,822, filed on Nov. 14, 2014.

(51) Int. Cl.
*A61B 17/34*  (2006.01)
*A61B 17/3205* (2006.01)
(Continued)

(52) U.S. Cl.
CPC ........ *A61B 17/3417* (2013.01); *A61B 17/205* (2013.01); *A61B 17/545* (2013.01);
(Continued)

(58) Field of Classification Search
CPC .......... A61B 5/14514; A61B 5/150984; A61B 5/150099; A61B 2017/00747;
(Continued)

(56) References Cited

U.S. PATENT DOCUMENTS 2,426,535 A   8/1947  Turkel
2,496,111 A   1/1950  Turkel
(Continued)

FOREIGN PATENT DOCUMENTS

AU   2012 211 122 B2   7/2016
CA         1275215 C   10/1990
(Continued)

OTHER PUBLICATIONS

Lemperle, G. et al., A Classification of Facial Wrinkles, Plastic and Reconstructive Surgery, 108(6):1735-1750 (2001).
(Continued)

*Primary Examiner* — Majid Jamialahmadi
(74) *Attorney, Agent, or Firm* — Onello & Mello, LLP

(57) ABSTRACT

Disclosed herein are apparatuses, systems, kits, and methods for treating skin, such as skin tightening or for treating diseases, disorders, and conditions that would benefit from tissue area or volume reduction, skin restoration, skin tightening, skin lifting, and/or skin repositioning and/or for generally improving skin function or appearance (e.g., the removal of unwanted skin features or irregularities such as sebaceous glands, sweat glands, hair follicles, necrosis, and fibrosis). Such apparatuses, systems, kits, and methods comprise an apparatus having a handheld main body and a detachably attachable tip comprising one or more needles.

28 Claims, 16 Drawing Sheets

(51) Int. Cl.

| | | |
|---|---|---|
| *A61B 17/00* | (2006.01) | |
| *A61B 17/20* | (2006.01) | |
| *A61B 17/54* | (2006.01) | |
| A61B 17/3203 | (2006.01) | |
| A61B 50/13 | (2016.01) | |
| A61B 17/32 | (2006.01) | |
| A61B 17/3213 | (2006.01) | |
| A61B 18/14 | (2006.01) | |
| A61B 18/20 | (2006.01) | |
| A61B 18/18 | (2006.01) | |
| A61N 7/00 | (2006.01) | |

(52) U.S. Cl.
CPC ..... *A61B 17/32002* (2013.01); *A61B 17/3203* (2013.01); *A61B 17/3213* (2013.01); *A61B 17/32053* (2013.01); *A61B 17/3478* (2013.01); *A61B 18/14* (2013.01); *A61B 18/203* (2013.01); *A61B 50/13* (2016.02); *A61B 2017/0023* (2013.01); *A61B 2017/00402* (2013.01); *A61B 2017/00424* (2013.01); *A61B 2017/00473* (2013.01); *A61B 2017/00544* (2013.01); *A61B 2017/00734* (2013.01); *A61B 2017/00747* (2013.01); *A61B 2017/00752* (2013.01); *A61B 2017/00756* (2013.01); *A61B 2017/00761* (2013.01); *A61B 2017/00769* (2013.01); *A61B 2017/00796* (2013.01); *A61B 2017/320004* (2013.01); *A61B 2017/32035* (2013.01); *A61B 2017/3437* (2013.01); *A61B 2017/3454* (2013.01); *A61B 2018/1807* (2013.01); *A61B 2217/005* (2013.01); *A61N 7/00* (2013.01)

(58) Field of Classification Search
CPC .... A61B 2018/00452; A61M 37/0015; A61M 2037/0061; A61M 5/3298
USPC ........................................................ 606/131
See application file for complete search history.

(56) References Cited

U.S. PATENT DOCUMENTS

| | | |
|---|---|---|
| 2,881,763 A | 4/1959 | Robbins |
| 3,001,522 A | 9/1961 | Silverman |
| 3,086,530 A | 4/1963 | Groom |
| 3,214,869 A | 11/1965 | Stryker |
| 3,598,108 A | 8/1971 | Jamshidi et al. |
| 3,640,279 A | 2/1972 | Brown et al. |
| 3,683,892 A | 8/1972 | Harris |
| 3,788,320 A | 1/1974 | Dye |
| 3,867,942 A | 2/1975 | Bellantoni et al. |
| 3,929,123 A | 12/1975 | Jamshidi |
| 4,108,096 A | 8/1978 | Ciecior |
| 4,159,659 A | 7/1979 | Nightingale |
| 4,167,179 A | 9/1979 | Kirsch |
| 4,403,617 A | 9/1983 | Tretinyak |
| 4,458,678 A | 7/1984 | Yannas et al. |
| 4,476,864 A | 10/1984 | Tezel |
| 4,604,346 A | 8/1986 | Bell et al. |
| 4,640,296 A | 2/1987 | Schnepp-Pesch et al. |
| 4,649,918 A | 3/1987 | Pegg et al. |
| D297,375 S | 8/1988 | Liu |
| 4,815,462 A | 3/1989 | Clark |
| 4,865,026 A | 9/1989 | Barrett |
| 4,903,709 A | 2/1990 | Skinner |
| D323,034 S | 1/1992 | Reinstein |
| 5,152,763 A | 10/1992 | Johnson |
| D338,070 S | 8/1993 | Lam |
| 5,242,453 A | 9/1993 | Gubich |
| D342,138 S | 12/1993 | Wollman et al. |
| 5,269,316 A | 12/1993 | Spitalny |
| 5,306,490 A | 4/1994 | Barley, Jr. |
| 5,324,305 A | 6/1994 | Kanner |
| 5,331,972 A | 7/1994 | Wadhwani et al. |
| 5,415,182 A | 5/1995 | Chin et al. |
| 5,417,683 A | 5/1995 | Shiao |
| 5,419,761 A | 5/1995 | Narayanan et al. |
| 5,439,475 A | 8/1995 | Bennett |
| 5,458,112 A | 10/1995 | Weaver |
| D377,404 S | 1/1997 | Izumi |
| 5,593,381 A | 1/1997 | Tannenbaum et al. |
| 5,611,810 A | 3/1997 | Arnold et al. |
| 5,615,690 A | 4/1997 | Giurtino et al. |
| 5,639,654 A | 6/1997 | Bernard et al. |
| 5,643,308 A | 7/1997 | Markman |
| D388,543 S | 12/1997 | Eguchi et al. |
| 5,713,375 A | 2/1998 | McAllister |
| 5,749,895 A | 5/1998 | Sawyer et al. |
| 5,792,169 A | 8/1998 | Markman |
| 5,810,857 A | 9/1998 | Mackool |
| 5,827,297 A | 10/1998 | Boudjema |
| 5,868,744 A | 2/1999 | Willmen |
| 5,879,326 A | 3/1999 | Godshall et al. |
| 5,885,211 A | 3/1999 | Eppstein et al. |
| 5,885,226 A | 3/1999 | Rubinstein et al. |
| 5,902,319 A | 5/1999 | Daley |
| 5,922,000 A | 7/1999 | Chodorow |
| 5,925,002 A | 7/1999 | Wollman |
| 5,928,162 A | 7/1999 | Giurtino et al. |
| 5,931,855 A | 8/1999 | Buncke |
| 5,989,273 A | 11/1999 | Arnold |
| 6,022,324 A | 2/2000 | Skinner |
| D425,241 S | 5/2000 | Nishizawa et al. |
| 6,059,807 A | 5/2000 | Soudjema |
| 6,063,094 A | 5/2000 | Rosenberg |
| 6,178,346 B1 | 1/2001 | Amundson et al. |
| 6,197,039 B1 | 3/2001 | Ashraf |
| 6,211,598 B1 | 4/2001 | Dhuler et al. |
| 6,241,687 B1 | 6/2001 | Voegele et al. |
| 6,241,739 B1 | 6/2001 | Waldron |
| 6,251,097 B1 | 6/2001 | Kline et al. |
| 6,264,618 B1 | 7/2001 | Landi et al. |
| 6,342,213 B1 | 1/2002 | Barley et al. |
| D457,265 S | 5/2002 | Gebhard |
| D458,710 S | 6/2002 | Altamore et al. |
| 6,419,641 B1 | 7/2002 | Mark et al. |
| 6,432,098 B1 | 8/2002 | Kline et al. |
| 6,440,086 B1 | 8/2002 | Hohenberg |
| 6,461,369 B1 | 10/2002 | Kim |
| 6,494,844 B1 | 12/2002 | Van Bladel et al. |
| 6,537,264 B1 | 3/2003 | Cormier et al. |
| 6,562,037 B2 | 5/2003 | Paton et al. |
| 6,669,618 B2 | 12/2003 | Reising et al. |
| 6,669,694 B2 | 12/2003 | Shadduck |
| 6,733,496 B2 | 5/2004 | Sharkey et al. |
| 6,733,498 B2 | 5/2004 | Paton et al. |
| D500,391 S | 12/2004 | Nielsen et al. |
| 6,881,203 B2 | 4/2005 | Delmore et al. |
| 6,887,250 B1 | 5/2005 | Dority et al. |
| 6,893,388 B2 | 5/2005 | Reising et al. |
| 6,936,039 B2 | 8/2005 | Kline et al. |
| D509,301 S | 9/2005 | Talbot et al. |
| 6,997,923 B2 | 2/2006 | Anderson et al. |
| 7,073,510 B2 | 7/2006 | Redmond et al. |
| 7,131,951 B2 | 11/2006 | Angel |
| D538,430 S | 3/2007 | Ohta |
| 7,618,429 B2 | 11/2009 | Mulholland |
| 7,651,507 B2 | 1/2010 | Mishra et al. |
| 7,658,728 B2 | 2/2010 | Yuzhakov |
| 7,926,401 B2 | 4/2011 | Mishra et al. |
| 8,128,639 B2 | 3/2012 | Tippett |
| 8,209,006 B2 | 6/2012 | Smith et al. |
| 8,226,664 B2 | 7/2012 | Drews et al. |
| 8,246,611 B2 | 8/2012 | Paithankar et al. |
| 8,349,554 B2 | 1/2013 | Bahrami et al. |
| 8,435,791 B2 | 5/2013 | Galun et al. |
| 8,480,592 B2 | 7/2013 | Chudzik et al. |
| 8,696,686 B2 | 4/2014 | Drews et al. |
| 8,900,181 B2 | 12/2014 | Knowlton |
| 8,951,266 B2 | 2/2015 | Zingaretti et al. |
| 9,017,343 B2 | 4/2015 | Westerling, Jr. et al. |

(56) References Cited

U.S. PATENT DOCUMENTS

| | | |
|---|---|---|
| 9,060,803 B2 | 6/2015 | Anderson et al. |
| 9,084,465 B2 | 7/2015 | Oostman, Jr. et al. |
| 9,119,945 B2 | 9/2015 | Simons et al. |
| 9,408,691 B2 | 8/2016 | Oostman et al. |
| 9,439,673 B2 | 9/2016 | Austen |
| 9,561,051 B2 | 2/2017 | Austen et al. |
| D797,286 S | 9/2017 | Ginggen et al. |
| 10,245,066 B2 | 4/2019 | Austen et al. |
| 10,251,792 B2 | 4/2019 | Levinson et al. |
| 10,278,677 B2 | 5/2019 | Austen et al. |
| 10,327,800 B2 | 6/2019 | Austen |
| 10,543,127 B2 | 1/2020 | Levinson et al. |
| 10,555,754 B2 | 2/2020 | Ginggen et al. |
| 10,624,698 B2 | 4/2020 | Anderson et al. |
| 10,687,842 B2 | 6/2020 | Austen et al. |
| 10,716,591 B2 | 7/2020 | Anderson et al. |
| 10,736,654 B2 | 8/2020 | Anderson et al. |
| 10,953,143 B2 | 3/2021 | Ginggen et al. |
| 11,166,743 B2 | 11/2021 | Levinson et al. |
| 2001/0018572 A1 | 8/2001 | Kinsey et al. |
| 2002/0022854 A1 | 2/2002 | Irion et al. |
| 2002/0022861 A1 | 2/2002 | Jacobs et al. |
| 2002/0045859 A1 | 4/2002 | Gartstein et al. |
| 2002/0103500 A1 | 8/2002 | Gildenberg |
| 2002/0120260 A1 | 8/2002 | Morris et al. |
| 2002/0169431 A1 | 11/2002 | Kline et al. |
| 2002/0183688 A1 | 12/2002 | Lastovich et al. |
| 2002/0187556 A1* | 12/2002 | Shartle .............. A61B 5/14514 |
| | | 436/149 |
| 2002/0188280 A1 | 12/2002 | Nguyen et al. |
| 2003/0023196 A1 | 1/2003 | Liguori |
| 2003/0083607 A1 | 5/2003 | Bobo, Jr. |
| 2003/0088220 A1 | 5/2003 | Molander et al. |
| 2003/0119641 A1 | 6/2003 | Reising |
| 2003/0135161 A1 | 7/2003 | Fleming et al. |
| 2003/0144656 A1* | 7/2003 | Ocel ...................... A61B 5/042 |
| | | 606/41 |
| 2003/0153960 A1 | 8/2003 | Chornenky et al. |
| 2003/0158521 A1 | 8/2003 | Ameri |
| 2003/0158566 A1 | 8/2003 | Brett |
| 2003/0163160 A1 | 8/2003 | O'Malley et al. |
| 2003/0181936 A1 | 9/2003 | Trautman et al. |
| 2003/0195625 A1 | 10/2003 | Garcia Castro et al. |
| 2003/0199811 A1 | 10/2003 | Sage et al. |
| 2003/0212415 A1* | 11/2003 | Karasiuk ................ A61B 17/54 |
| | | 606/131 |
| 2003/0233082 A1 | 12/2003 | Kline et al. |
| 2004/0002723 A1 | 1/2004 | Ball |
| 2004/0010268 A1 | 1/2004 | Gabehart |
| 2004/0019297 A1 | 1/2004 | Angel |
| 2004/0023771 A1 | 2/2004 | Reising et al. |
| 2004/0054410 A1 | 3/2004 | Barrows |
| 2004/0073195 A1 | 4/2004 | Cucin |
| 2004/0087992 A1 | 5/2004 | Gartstein et al. |
| 2004/0122471 A1 | 6/2004 | Toby et al. |
| 2004/0138680 A1 | 7/2004 | Twitchell et al. |
| 2004/0162566 A1 | 8/2004 | Carson et al. |
| 2004/0175690 A1 | 9/2004 | Mishra et al. |
| 2004/0220589 A1 | 11/2004 | Feller |
| 2005/0049582 A1 | 3/2005 | DeBenedictis et al. |
| 2005/0090765 A1 | 4/2005 | Fisher |
| 2005/0130821 A1 | 6/2005 | Reising et al. |
| 2005/0165329 A1 | 7/2005 | Taylor et al. |
| 2005/0171480 A1* | 8/2005 | Mukerjee .......... A61M 37/0015 |
| | | 604/173 |
| 2005/0203575 A1 | 9/2005 | Carson et al. |
| 2005/0209567 A1 | 9/2005 | Sibbitt |
| 2005/0215921 A1 | 9/2005 | Hibner et al. |
| 2005/0215970 A1 | 9/2005 | Kline et al. |
| 2005/0215971 A1 | 9/2005 | Roe et al. |
| 2005/0226856 A1 | 10/2005 | Ahlfors |
| 2005/0234419 A1 | 10/2005 | Kline et al. |
| 2005/0245952 A1 | 11/2005 | Feller |
| 2005/0283141 A1 | 12/2005 | Giovannoli |
| 2006/0047234 A1 | 3/2006 | Glucksman et al. |
| 2006/0064031 A1 | 3/2006 | Miller |
| 2006/0116605 A1 | 6/2006 | Nakao |
| 2006/0155266 A1 | 7/2006 | Manstein et al. |
| 2006/0161179 A1 | 7/2006 | Kachenmeister |
| 2006/0184153 A1 | 8/2006 | Mark et al. |
| 2006/0193819 A1 | 8/2006 | Lu et al. |
| 2006/0216781 A1 | 9/2006 | Gebing |
| 2006/0259006 A1 | 11/2006 | McKay et al. |
| 2006/0264926 A1 | 11/2006 | Kochamba |
| 2006/0271070 A1 | 11/2006 | Eriksson et al. |
| 2006/0276806 A1 | 12/2006 | Martinez Zunino |
| 2007/0010810 A1 | 1/2007 | Kochamba |
| 2007/0038181 A1 | 2/2007 | Melamud et al. |
| 2007/0038236 A1 | 2/2007 | Cohen |
| 2007/0060888 A1 | 3/2007 | Goff et al. |
| 2007/0073217 A1 | 3/2007 | James |
| 2007/0073327 A1 | 3/2007 | Giovannoli |
| 2007/0078359 A1* | 4/2007 | Luloh ................ A61F 9/00763 |
| | | 600/576 |
| 2007/0078466 A1 | 4/2007 | Bodduluri et al. |
| 2007/0078473 A1 | 4/2007 | Bodduluri et al. |
| 2007/0106306 A1 | 5/2007 | Bodduluri et al. |
| 2007/0142722 A1 | 6/2007 | Chang |
| 2007/0142744 A1 | 6/2007 | Provencher |
| 2007/0142885 A1 | 6/2007 | Hantash et al. |
| 2007/0149991 A1 | 6/2007 | Mulholland |
| 2007/0156161 A1 | 7/2007 | Weadock et al. |
| 2007/0167958 A1 | 7/2007 | Sulamanidze et al. |
| 2007/0179455 A1 | 8/2007 | Geliebter et al. |
| 2007/0183938 A1 | 8/2007 | Booker |
| 2007/0198000 A1 | 8/2007 | Miyamoto et al. |
| 2007/0213634 A1 | 9/2007 | Teague |
| 2007/0239236 A1 | 10/2007 | Manstein |
| 2007/0239260 A1 | 10/2007 | Palanker et al. |
| 2007/0249960 A1 | 10/2007 | Williamson |
| 2007/0270710 A1* | 11/2007 | Frass .................. A61B 10/0045 |
| | | 600/567 |
| 2008/0009802 A1 | 1/2008 | Lambino et al. |
| 2008/0009896 A1 | 1/2008 | Shiao |
| 2008/0009901 A1 | 1/2008 | Redmond et al. |
| 2008/0033334 A1 | 2/2008 | Gurtner et al. |
| 2008/0045858 A1 | 2/2008 | Tessitore et al. |
| 2008/0045861 A1 | 2/2008 | Miller et al. |
| 2008/0132979 A1 | 6/2008 | Gerber |
| 2008/0146982 A1 | 6/2008 | Rastegar et al. |
| 2008/0183167 A1 | 7/2008 | Britva et al. |
| 2008/0208146 A1 | 8/2008 | Brandwein et al. |
| 2008/0221548 A1 | 9/2008 | Danenberg et al. |
| 2008/0234602 A1 | 9/2008 | Oostman et al. |
| 2008/0234699 A1 | 9/2008 | Oostman Jr et al. |
| 2008/0269735 A1 | 10/2008 | Vila Echague et al. |
| 2008/0275378 A1 | 11/2008 | Herndon |
| 2008/0300507 A1 | 12/2008 | Figueredo et al. |
| 2008/0306471 A1 | 12/2008 | Altshuler et al. |
| 2008/0312648 A1 | 12/2008 | Peterson |
| 2009/0030340 A1 | 1/2009 | Mc Clellan |
| 2009/0048557 A1 | 2/2009 | Yeshurun et al. |
| 2009/0088720 A1 | 4/2009 | Oostman, Jr. |
| 2009/0093864 A1 | 4/2009 | Anderson |
| 2009/0146068 A1 | 6/2009 | Agarwal |
| 2009/0163877 A1* | 6/2009 | Christoffersen ...... A61M 5/3286 |
| | | 604/240 |
| 2009/0198336 A1 | 8/2009 | Qiao et al. |
| 2009/0227895 A1 | 9/2009 | Goldenberg |
| 2009/0312749 A1 | 12/2009 | Pini et al. |
| 2010/0023003 A1 | 1/2010 | Mulholland |
| 2010/0030152 A1 | 2/2010 | Lee et al. |
| 2010/0041938 A1 | 2/2010 | Stoianovici et al. |
| 2010/0057100 A1 | 3/2010 | Zeevi |
| 2010/0082042 A1 | 4/2010 | Drews |
| 2010/0121307 A1 | 5/2010 | Lockard et al. |
| 2010/0145373 A1 | 6/2010 | Alon |
| 2010/0160822 A1 | 6/2010 | Parihar et al. |
| 2010/0185116 A1 | 7/2010 | Al-Mohizea |
| 2010/0286618 A1 | 11/2010 | Choi |
| 2010/0330589 A1 | 12/2010 | Bahrami et al. |
| 2011/0009882 A1 | 1/2011 | Remsburg et al. |
| 2011/0028898 A1 | 2/2011 | Clark, III et al. |
| 2011/0040497 A1 | 2/2011 | Olesen |

(56) References Cited

U.S. PATENT DOCUMENTS

| | | |
|---|---|---|
| 2011/0046616 A1 | 2/2011 | Manstein |
| 2011/0092844 A1 | 4/2011 | Bargo et al. |
| 2011/0105949 A1 | 5/2011 | Wiksell |
| 2011/0152738 A1 | 6/2011 | Zepeda et al. |
| 2011/0166520 A1 | 7/2011 | Iwase et al. |
| 2011/0172745 A1 | 7/2011 | Na et al. |
| 2011/0245834 A1 | 10/2011 | Miklosovic |
| 2011/0251602 A1 | 10/2011 | Anderson et al. |
| 2011/0257588 A1 | 10/2011 | Knowlton |
| 2011/0270274 A1 | 11/2011 | Hull, Jr. |
| 2011/0282238 A1 | 11/2011 | Houser et al. |
| 2011/0313345 A1 | 12/2011 | Schafer |
| 2011/0313429 A1 | 12/2011 | Anderson et al. |
| 2012/0041430 A1 | 2/2012 | Anderson et al. |
| 2012/0065551 A1 | 3/2012 | Aviad et al. |
| 2012/0136387 A1 | 5/2012 | Redmond et al. |
| 2012/0158100 A1 | 6/2012 | Schomacker |
| 2012/0179189 A1 | 7/2012 | Zingaretti et al. |
| 2012/0209283 A1 | 8/2012 | Zhu |
| 2012/0226214 A1 | 9/2012 | Gurtner et al. |
| 2012/0226268 A1 | 9/2012 | Liu et al. |
| 2012/0226306 A1 | 9/2012 | Jackson et al. |
| 2012/0245629 A1 | 9/2012 | Gross et al. |
| 2012/0253333 A1 | 10/2012 | Garden et al. |
| 2012/0259237 A1* | 10/2012 | Axelrod ............ A61M 5/1452 600/506 |
| 2012/0271320 A1 | 10/2012 | Hall et al. |
| 2013/0006168 A1 | 1/2013 | Del Vecchio |
| 2013/0041397 A1* | 2/2013 | Nishimura .......... A61H 39/086 606/189 |
| 2013/0045171 A1 | 2/2013 | Utecht et al. |
| 2013/0110026 A1 | 5/2013 | Jackson et al. |
| 2013/0131635 A1 | 5/2013 | Rimsa et al. |
| 2013/0204238 A1 | 8/2013 | Lederman et al. |
| 2014/0036523 A1 | 2/2014 | Thullier et al. |
| 2014/0039523 A1 | 2/2014 | Austen |
| 2014/0163582 A1 | 6/2014 | Austen et al. |
| 2014/0200484 A1 | 7/2014 | Austen et al. |
| 2014/0249547 A1* | 9/2014 | Boone, III ............ A61B 17/545 606/131 |
| 2014/0276959 A1 | 9/2014 | Oostman et al. |
| 2014/0277055 A1 | 9/2014 | Austen, Jr. |
| 2014/0296741 A1 | 10/2014 | Austen |
| 2014/0296796 A1 | 10/2014 | Lim |
| 2014/0303648 A1 | 10/2014 | Knowlton |
| 2014/0343481 A1* | 11/2014 | Ignon ................ A61M 5/3298 604/21 |
| 2015/0143713 A1 | 5/2015 | Cheng |
| 2015/0173991 A1 | 6/2015 | Anderson et al. |
| 2015/0216545 A1 | 8/2015 | Anderson et al. |
| 2015/0238214 A1 | 8/2015 | Anderson et al. |
| 2015/0258319 A1 | 9/2015 | Simmers |
| 2015/0320990 A1 | 11/2015 | Burton et al. |
| 2015/0366719 A1 | 12/2015 | Levinson et al. |
| 2016/0082241 A1 | 3/2016 | Burton et al. |
| 2016/0095592 A1 | 4/2016 | Levinson et al. |
| 2016/0121091 A1* | 5/2016 | Burton .............. A61M 37/0015 604/173 |
| 2016/0129198 A1* | 5/2016 | Bitar .................. A61M 5/3202 604/115 |
| 2016/0136406 A1 | 5/2016 | Berry et al. |
| 2016/0192961 A1 | 7/2016 | Ginggen et al. |
| 2016/0317721 A1 | 11/2016 | Ginggen et al. |
| 2016/0367280 A1 | 12/2016 | Austen |
| 2017/0105749 A1 | 4/2017 | Austen et al. |
| 2018/0008500 A1 | 1/2018 | Anderson et al. |
| 2018/0021087 A1 | 1/2018 | Anderson et al. |
| 2018/0036029 A1 | 2/2018 | Anderson et al. |
| 2018/0078278 A1 | 3/2018 | Levinson et al. |
| 2018/0140316 A1 | 5/2018 | Anderson et al. |
| 2018/0185196 A1 | 7/2018 | Levinson et al. |
| 2018/0193054 A1 | 7/2018 | Austen |
| 2018/0206875 A1 | 7/2018 | Austen et al. |
| 2019/0099199 A1 | 4/2019 | Levinson et al. |
| 2019/0231324 A1 | 8/2019 | Austen et al. |
| 2019/0366067 A1 | 12/2019 | Ginggen et al. |
| 2020/0038051 A1 | 2/2020 | Austen |
| 2020/0121354 A1 | 4/2020 | Ginggen et al. |
| 2020/0188184 A1 | 6/2020 | Levinson et al. |
| 2020/0214766 A1 | 7/2020 | Anderson et al. |
| 2020/0246039 A1 | 8/2020 | Levinson et al. |
| 2020/0360039 A1 | 11/2020 | Anderson et al. |
| 2020/0360043 A1 | 11/2020 | Anderson et al. |
| 2021/0059703 A1 | 3/2021 | Austen et al. |
| 2021/0178028 A1 | 6/2021 | Ginggen et al. |
| 2021/0322005 A1 | 10/2021 | Levinson et al. |

FOREIGN PATENT DOCUMENTS

| | | |
|---|---|---|
| CA | 2361777 A1 | 5/2002 |
| CN | 2126570 Y | 1/1993 |
| CN | 1115629 A | 1/1996 |
| CN | 201005966 Y | 1/2008 |
| CN | 101128156 A | 2/2008 |
| CN | 101208128 A | 6/2008 |
| CN | 101232858 A | 7/2008 |
| CN | 101277657 A | 10/2008 |
| CN | 101312692 A | 11/2008 |
| CN | 101347346 A | 1/2009 |
| CN | 101563113 A | 10/2009 |
| CN | 101670145 A | 3/2010 |
| CN | 102119006 A | 7/2011 |
| CN | 102143724 A | 8/2011 |
| CN | 102178616 A | 9/2011 |
| CN | 202113484 U | 1/2012 |
| CN | 103547226 A | 1/2014 |
| DE | 287651 A5 | 3/1991 |
| DE | 202004010659 U1 | 10/2004 |
| DE | 102007026973 A1 | 12/2008 |
| EA | 9092 | 10/2007 |
| EP | 0027974 A1 | 5/1981 |
| EP | 1224949 A1 | 7/2002 |
| EP | 1278061 A1 | 1/2003 |
| EP | 1396230 A1 | 3/2004 |
| EP | 1618925 A1 | 1/2006 |
| EP | 2181732 A1 | 5/2010 |
| EP | 1278061 B1 | 2/2011 |
| EP | 2409727 A1 | 1/2012 |
| FR | 2846221 B1 | 7/2005 |
| JP | S57-163208 A | 10/1982 |
| JP | 2000-139929 A | 5/2000 |
| JP | 2001-187058 A | 7/2001 |
| JP | 2002-505605 A | 2/2002 |
| JP | 2003-515424 A | 5/2003 |
| JP | 2003-518975 A | 6/2003 |
| JP | 2003-532480 A | 11/2003 |
| JP | 2004-503342 A | 2/2004 |
| JP | 2005-000642 A | 1/2005 |
| JP | 2005-87519 A | 4/2005 |
| JP | 2005-87520 A | 4/2005 |
| JP | 2005-103276 A | 4/2005 |
| JP | 2006-516201 A | 6/2006 |
| JP | 2006-517814 A | 8/2006 |
| JP | 2007-041267 A | 2/2007 |
| JP | 2007-100140 A | 4/2007 |
| JP | 2008-036393 A | 2/2008 |
| JP | 2008-528207 A | 7/2008 |
| JP | 2009-502413 A | 1/2009 |
| JP | 2009-507773 A | 2/2009 |
| JP | 2009-509671 A | 3/2009 |
| JP | 2009-172418 A | 8/2009 |
| JP | 2009-219858 A | 10/2009 |
| JP | 2009-545382 A | 12/2009 |
| JP | 2010-000210 A | 1/2010 |
| JP | 4431637 B2 | 3/2010 |
| JP | 2010-515469 A | 5/2010 |
| JP | 2010-524591 A | 7/2010 |
| JP | 2010-525887 A | 7/2010 |
| JP | 2010532178 | 10/2010 |
| JP | 2011-516169 A | 5/2011 |
| JP | 2013-526300 A | 6/2013 |
| JP | 2014506498 | 3/2014 |
| JP | 5944925 B2 | 7/2016 |

(56) References Cited

FOREIGN PATENT DOCUMENTS

| | | |
|---|---|---|
| KR | 2008-0030553 A | 4/2008 |
| KR | 2008-0049793 A | 6/2008 |
| KR | 2010-0135863 A | 12/2010 |
| KR | 2010/0135864 A | 12/2010 |
| KR | 101571291 B1 | 11/2015 |
| RU | 1801391 | 3/1993 |
| RU | 1801391 C | 3/1993 |
| RU | 2119304 C1 | 9/1998 |
| RU | 11679 | 11/1999 |
| RU | 28328 | 3/2003 |
| RU | 50799 | 1/2006 |
| RU | 58359 | 11/2006 |
| RU | 2289332 C2 | 12/2006 |
| RU | 2308873 C2 | 10/2007 |
| RU | 2325859 C2 | 6/2008 |
| SU | 1426740 | 9/1988 |
| TW | 402497 B | 8/2000 |
| TW | 200841866 A | 11/2008 |
| WO | WO-93/22971 A1 | 11/1993 |
| WO | WO-1995/28896 A1 | 11/1995 |
| WO | WO-97/18758 A1 | 5/1997 |
| WO | WO-98/26719 A1 | 6/1998 |
| WO | WO-98/57587 A1 | 12/1998 |
| WO | WO-99/29243 A1 | 6/1999 |
| WO | WO-0141651 A2 | 6/2001 |
| WO | WO-01/49186 A2 | 7/2001 |
| WO | WO-01/85035 A2 | 11/2001 |
| WO | WO-02/05890 A2 | 1/2002 |
| WO | WO-02/096321 A1 | 12/2002 |
| WO | WO-2004/045671 A2 | 6/2004 |
| WO | WO-2004/107984 A1 | 12/2004 |
| WO | WO-2005/013830 A1 | 2/2005 |
| WO | WO-2005/072181 A2 | 8/2005 |
| WO | WO-2005/109799 A2 | 11/2005 |
| WO | WO-2006/081556 A2 | 8/2006 |
| WO | WO-2006/116281 A2 | 11/2006 |
| WO | WO-2006/118804 A1 | 11/2006 |
| WO | WO-2007/011788 A2 | 1/2007 |
| WO | WO-2007/015232 A1 | 2/2007 |
| WO | WO-2007/015247 A2 | 2/2007 |
| WO | WO-2007/024038 A1 | 3/2007 |
| WO | WO-2007/041267 A2 | 4/2007 |
| WO | WO-2007/066339 A1 | 6/2007 |
| WO | WO-2007/080596 A2 | 7/2007 |
| WO | WO-2007/106170 A2 | 9/2007 |
| WO | WO-2008/019051 A2 | 2/2008 |
| WO | WO-2008/033873 A2 | 3/2008 |
| WO | WO-2008/052189 A2 | 5/2008 |
| WO | 2008121920 | 10/2008 |
| WO | WO-2008/131302 A2 | 10/2008 |
| WO | WO-2009/040493 A1 | 4/2009 |
| WO | WO-2009/072711 A2 | 6/2009 |
| WO | WO-2009/099988 A2 | 8/2009 |
| WO | WO-2009/137288 A2 | 11/2009 |
| WO | WO-2009/146053 A1 | 12/2009 |
| WO | WO-2009/146068 A1 | 12/2009 |
| WO | WO-2009/146072 A1 | 12/2009 |
| WO | WO-2010/027188 A2 | 3/2010 |
| WO | WO-2010/080014 A2 | 7/2010 |
| WO | WO-2010/095456 A1 | 8/2010 |
| WO | WO-2010/097790 A1 | 9/2010 |
| WO | WO-2011/006009 A1 | 1/2011 |
| WO | WO-2011/019859 A2 | 2/2011 |
| WO | WO-2011/075676 A2 | 6/2011 |
| WO | WO-2011/104875 A1 | 9/2011 |
| WO | WO-2011/123218 A1 | 10/2011 |
| WO | WO-2011/075676 A3 | 11/2011 |
| WO | WO-2011140497 A2 | 11/2011 |
| WO | WO-2012/052986 A2 | 4/2012 |
| WO | WO-2012/103483 A2 | 8/2012 |
| WO | WO-2012/103488 A1 | 8/2012 |
| WO | WO-2012/103492 A1 | 8/2012 |
| WO | WO-2012/119131 A1 | 9/2012 |
| WO | WO-2012/135828 A1 | 10/2012 |
| WO | WO-2013/013196 A1 | 1/2013 |
| WO | WO-2013/013199 A2 | 1/2013 |
| WO | WO-2013/104414 A1 | 7/2013 |
| WO | WO-2014/008470 A1 | 1/2014 |
| WO | WO-2014/008481 A1 | 1/2014 |
| WO | 2014028626 | 2/2014 |
| WO | WO-2014/089488 A2 | 6/2014 |
| WO | WO-2014/130359 A1 | 8/2014 |
| WO | WO-2014/151104 A1 | 9/2014 |
| WO | WO-2014/179729 A1 | 11/2014 |
| WO | WO-2015/021434 A2 | 2/2015 |
| WO | WO-2015/051164 A2 | 4/2015 |
| WO | WO-2015/095675 A1 | 6/2015 |
| WO | WO-2015/126926 A1 | 8/2015 |
| WO | WO-2016/033584 A1 | 3/2016 |
| WO | WO-2016/033586 A1 | 3/2016 |
| WO | WO-2016/077759 A1 | 5/2016 |
| WO | WO-2016/127091 A1 | 8/2016 |
| WO | WO-2017/139773 A2 | 8/2017 |
| WO | WO-2017/172920 A1 | 10/2017 |
| WO | WO-2017/192723 A1 | 11/2017 |
| WO | WO-2018/057630 A1 | 3/2018 |
| WO | WO-2018/057637 A1 | 3/2018 |
| WO | WO-2020/097244 A1 | 5/2020 |

OTHER PUBLICATIONS

Narins, R. et al., Validated Assessment Scales for the Lower Face, Dermatology Surgery, 38:333-342 (2012).
Alsberg, E. et al., Engineering growing tissues, PNAS, 99(19):12025-12030 (2002).
Banzhaf, C. et al., Spatiotemporal Closure of Fractional Laser-Ablated Channels Imaged by Optical Coherence Tomography and Reflectance Confocal Microscopy, Lasers in Surgery and Medicine, 48:157-165 (2016).
Bedi, V. et al.. The effects of pulse energy variations on the dimensions of microscopic thermal treatment zones in nonablative fractional resurfacing, Lasers Surg Med, 39(2):145-55 (2007).
Cevc, Gregor, Drug delivery across the skin, Expert Opinion Investigational Drugs, 6(12):1887-937 (1997).
Chang, Te-Sheng, An updated review of tyrosinase inhibitors, Int J Mol Sci, 10(6):2440-2475 (2009).
International Search Report for International Patent Application No. PCT/US2012/022980 dated Aug. 9, 2012.
International Written Opinion for International Patent Application No. PCT/US2012/022980 dated Aug. 9, 2012.
Czech, Z. et al., Pressure-sensitive adhesives for medical applications, Wide Spectra of Quality Control, Akyar, 309-332 (2011).
De las Heras Alarcon et al., Stimuli responsive polymers for biomedical applications, Chem Soc Rev. 34(3):276-85 (2005).
Dini, G. et al., Grasping leather plies by Bernoulli grippers, CIRP Ann Manuf Technol. 58(1):21-4 (2009).
Dujardin, J. et al., In vivo assessment of skin electroporation using sguare wave pulses, J Control Release, 79(1-3):219-27 (2002).
Dunkin, C. et al., Scarring occurs at a critical depth of skin injury: precise measurement in a graduated dermal scratch in human volunteers, Plast Reconstr Surg, 119(6):1722-32 (2007).
European Patent Office, Supplementary European Search Report, Application No. EP13813955.5, dated Mar. 18, 2016.
European Search Report for European Application No. 12739664.6 dated May 20, 2014.
Extended European Search Report, Application No. 12814711.3, dated Feb. 11, 2015.
Fernandes, J. et al., Micro-mechanical fractional skin rejuvenation, Plast Reconstr Surg, 130(5S-1):28 (2012).
Fernandes, J. et al., Micro-mechanical fractional skin rejuvenation, Plast Reconstr Surg, 131(2):216-23 (2013).
Galaev., 'Smart' polymers in biotechnology and medicine, Russ Chem Rev. 64(5):471-489 (1995).
Hale, G. and Querry, M. , Optical constants of water in the 200-nm to 200-microm wavelength region, Appl Opt, 12(3):555-63 (1973).
Han, H. et al., Combined, Minimally Invasive, Thread-based Facelift, Archives of Aesthetic Plastic Surgery, 20(3):160-164 (2014).
Huang, W.M. et al., Shape memory materials, Material Today, 13(7-8):54-61 (2010).

(56) References Cited

OTHER PUBLICATIONS

International Preliminary Report on Patentability for International Patent Application No. PCT/US2009/039125, dated Oct. 5, 2010 (6 pages).
International Preliminary Report on Patentability for International Patent Application No. PCT/US2012/022987, dated Jul. 30, 2013 (5 pages).
International Preliminary Report on Patentability for International Patent Application No. PCT/US2012/022993, dated Jul. 30, 2013 (5 pages).
International Preliminary Report on Patentability for International Patent Application No. PCT/US2012/047716, dated Nov. 4, 2014 (4 pages).
International Preliminary Report on Patentability for International Patent Application No. PCT/US2013/049445, dated Jan. 6, 2015 (4 pages).
International Preliminary Report on Patentability for International Patent Application No. PCT/US2014/036638, dated Nov. 3, 2015 (7 pages).
International Preliminary Report on Patentability for International Patent Application No. PCT/US2014/050426, dated Feb. 9, 2016 (8 pages).
International Search Report and Written Opinion for International Patent Application No. PCT/US2009/039125, dated Nov. 16, 2009 (9 pages).
International Search Report and Written Opinion for International Patent Application No. PCT/US2012/022987, dated Apr. 12, 2012 (6 pages).
International Search Report and Written Opinion for International Patent Application No. PCT/US2012/022993, dated May 17, 2012 (6 pages).
International Search Report and Written Opinion for International Patent Application No. PCT/US2012/047716, dated Oct. 25, 2012 (5 pages).
International Search Report and Written Opinion for International Patent Application No. PCT/US2013/049445, dated Oct. 18, 2013 (5 pages).
International Search Report and Written Opinion for International Patent Application No. PCT/US2014/016483, dated May 6, 2014 (9 pages).
International Search Report and Written Opinion for International Patent Application No. PCT/US2014/036638, dated Oct. 2, 2014 (10 pages).
International Search Report and Written Opinion for International Patent Application No. PCT/US2014/050426, dated Feb. 4, 2015 (11 pages).
International Search Report and Written Opinion for PCT/US2009/039125 dated Nov. 16, 2009.
International Search Report and Written Opinion for PCT/US2011/035613, dated May 6, 2011.
International Search Report and Written Opinion issued by the Korean Intellectual Property Office as International Searching Authority for International Application No. PCT/US2009/039114 dated Nov. 16, 2009 (10 pages).
International Search Report and Written Opinion dated Oct. 18, 2013 in connection with PCT/US2013/049445.
International Search Report for International Patent Application No. PCT/US2012/022987 dated Apr. 12, 2012.
International Search Report for International Patent Application No. PCT/US2012/022993 dated May 17, 2012.
International Search Report for International Patent Application No. PCT/US2012/047708.
International Search Report for PCT/US14/36638, 4 pages (dated Oct. 2, 2014).
International Search Report for PCT/US14/71443, 3 pages (dated Mar. 19, 2015).
International Search Report for PCT/US2014/016483, 3 pages (dated May 6, 2014).
International Search Report for PCT/US2015/060685, 3 pages (dated Feb. 2, 2016).
International Search Report for PCT/US2017/024752, 8 pages (dated Aug. 29, 2017).
International Search Report for PCT/US2017/052528 (Devices and Methods for Cosmetic Skin Resurfacing, filed Sep. 20, 2017), issued by ISA/US, 5 pages (dated Jan. 4, 2018).
International Search Report for PCT/US2017/052539 (Rapid Skin Treatment Using Microcoring, filed Sep. 20, 2017), issued by ISA/US, 7 pages (dated Nov. 22, 2017).
International Searching Report and Written Opinion issued by the Korean Intellectual Property Office as International Search Authority for International Application No. PCT/US2011/035613 dated Jan. 12, 2012 (6 pages).
International Written Opinion for International Patent Application No. PCT/US2012/022993 dated May 17, 2012.
International Written Opinion or International Patent Application No. PCT/US2012/022987 dated Apr. 12, 2012.
Kakasheva-Mazenkovska, L. et al., Variations of the histomorphological characteristics of human skin of different body regions in subjects of different age, Contributions, 32(2):119-28 (2011).
Konermann, W. et al., Ultrasonographically guided needle biopsy of benign and malignant soft tissue and bone tumors, J Ultrasound Med, 19(7):465-71 (2000).
Lien, T.K. and Davis, P.G.G., A novel gripper for limp materials based on lateral Coanda ejectors, CIRP Ann Manuf Technol, 57(1):33-6 (2008).
Majid, Imran, Microneedling therapy in atrophic facial scars: an objective assessment, J Cutan Aesthet Surg. 2(1):26-30 (2009).
Moore, J. et al., Modeling of the Plane Needle Cutting Edge Rake and Inclination Angles for Biopsy, Journal of Manufacturing Science and Engineering, 132:051005-1-051005-8 (2010).
PCT International Preliminary Report on Patentability, PCT/US2014/036638, dated Nov. 3, 2015, 7 pages.
PCT International Preliminary Report on Patentability, PCT/US2014/050426, dated Feb. 9, 2016, 8 pages.
PCT International Search Report and Written Opinion, PCT/US2014/036638, dated Oct. 2, 2014, 10 pages.
PCT International Search Report and Written Opinion, PCT/US2014/050426, dated Feb. 4, 2015, 18 pages.
Pliquett, U. et al., A propagating heatwave model of skin electroporation, J Theor Biol, 251(2):195-201 (2008).
Prausnitz, M. et al.. Electroporation of mammalian skin: a mechanism to enhance transdermal drug delivery, Proc Natl Acad Sci USA, 90(22):10504-8 (1993).
Salam, G. and Amin, J., The basic Z-plasty, Am Fam Physician, 67(11):2329-32 (2003).
Written Opinion for International Patent Application No. PCT/US2012/047708.
Written Opinion for PCT/US14/36638, 6 pages (dated Oct. 2, 2014).
Written Opinion for PCT/US14/71443, 4 pages (dated Mar. 19, 2015).
Written Opinion for PCT/US2014/016483, 6 pages (dated May 6, 2014).
Written Opinion for PCT/US2015/060685, 4 pages (dated Feb. 2, 2016).
Written Opinion for PCT/US2017/024752, 11 pages (dated Aug. 29, 2017).
Written Opinion for PCT/US2017/052528 (Devices and Methods for Cosmetic Skin Resurfacing, filed Sep. 20, 2017), issued by ISA/US, 17 pages (dated Jan. 4, 2018).
Written Opinion for PCT/US2017/052539 (Rapid Skin Treatment Using Microcoring, filed Sep. 20, 2017), issued by ISA/US, 8 pages (dated Nov. 22, 2017).
Zhu, J. et al., The Efficacy and Safety of Fractional CO2 Laser Combined with Topical Type A Botulinum Toxin for Facial Rejuvenation: A Randomized Controlled Split-Face Study, BioMed Research International, 7 pages (2016).
International Search Report for PCT/US2019/060131 (Systems and Methods for Skin Treatment, filed Nov. 6, 2019) received from ISA/EP, 5 pages (dated Mar. 27, 2020).
Written Opinion for PCT/US2019/060131 (Systems and Methods for Skin Treatment, filed Nov. 6, 2019) received from ISA/EP, 7 pages (dated Mar. 27, 2020).

(56) References Cited

OTHER PUBLICATIONS

Australian Office Action dated Jul. 10, 2020 issued in corresponding Australian Application No. 2015346141.
Australian Office Action dated May 26, 2021 issued in corresponding Australian Application No. 2015346141.
Brazilian Office Action dated Mar. 3, 2020 issued in corresponding Brazilian Application No. 112017009805-9, with English summary.
Extended European Search Report dated Jun. 8, 2018 issued in corresponding European Application No. 15858273.4.
Japanese Office Action dated Sep. 3, 2019 issued in corresponding Japanese Application No. 2017-525564, with English translation.
Japanese Office Action dated Aug. 4, 2020 issued in corresponding Japanese Application No. 2017-525564, with English translation.
Dai, et al., Magnetically-Responsive Self Assembled Composites, Chemical Society Reviews, 2010, 39:4057-4066.
Glogau, Aesthetic and Anatomic Analysis of the Aging Skin, Seminars in Cutaneous Medicine and Surgery, 1996, 15 (3):134-138.
"Method and Apparatus for Damage and Removal of Fat", Specification, Drawings and Prosecution History of U.S. Appl. No. 15/916,020, filed Mar. 8, 2018, by William G. Austen, which is stored in the United States Patent and Trademark Office (USPTO).
"Method and Apparatus for Damage and Removal of Fat", Specification, Drawings and Prosecution History of U.S. Appl. No. 14/233,985, filed Jun. 3, 2014, by William G. Austen, which is stored in the United States Patent and Trademark Office (USPTO).
European Office Action dated Jan. 13, 2022 issued in corresponding European Application No. 15858273.4.
Canadian Office Action dated Jan. 31, 2022 issued in corresponding Canadian Application No. 2967636.
Brazilian Office Action dated Feb. 15, 2022 issued in corresponding Brazilian Application No. 112017009805-9, with English translation.

* cited by examiner

DEVICES AND METHODS FOR ABLATION OF THE SKIN

FIELD OF THE INVENTION

The field of the present invention relates to treatments for skin and proximal tissue layers (e.g., skin tightening, treating diseases, disorders, and conditions of the skin, skin restoration, skin lifting, skin repositioning, and tattoo removal).

BACKGROUND OF THE INVENTION

Many human health issues arise from the damage or loss of tissue due to disease, advanced age, and/or injury. In aesthetic medicine, elimination of excess tissue and/or skin laxity is an important concern that affects more than 25% of the U.S. population. Conventional surgical therapies (e.g., a face lift, brow lift, or breast lift) can be effective but are often invasive, inconvenient, and expensive, while scarring limits the applicability of surgery to certain treatment sites.

Although minimally invasive methods are available, such methods are generally less effective than surgical methods. Methods using energy sources (e.g., laser, non-coherent light, radiofrequency, and ultrasound) can be effective at improving the architecture and texture of the skin but are much less effective at tightening the skin or reducing skin laxity. Neurotoxins, such as botulinum toxin, reduce the formation of dynamic wrinkles by paralysis of the injected muscles, but such toxins have minimal or no direct effect on skin tightness or laxity. Finally, dermal fillers, such as hyaluronic acid, can be injected in the dermal layer to smooth out wrinkles and improve contours, but such fillers do not directly tighten or reduce laxity of the skin. Thus, surgical therapies remain the gold standard for lifting and/or tightening skin, as compared to energy-based techniques (e.g., laser, radiofrequency, and ultrasound) and injection-based techniques (e.g., botulinum toxin and fillers such as hyaluronic acid- and collagen-based fillers).

Tissue ablative methods such as ablative fractional laser treatment create micro-ablations with photo-thermal energy. The use of such energy generates a coagulation zone in tissue that interferes with closure of the ablation zones thereby inhibiting tissue tightening. These methods also require longer patient healing times due to the biological reparative response to coagulated and dead tissue during the remodeling process. Laser ablation depth is typically limited by the depth of the laser beam focus. Ablation of deeper tissue layers than is possible with available laser systems is desirable for the treatment of scars, for example.

Accordingly, there is a need for improved methods and devices that provide increased effectiveness over currently available minimally-invasive techniques while maintaining convenience, affordability, and accessibility to patients desiring tissue restoration.

SUMMARY OF THE INVENTION

This invention relates to apparatuses, systems, kits, and methods for non-thermal tissue ablation. The invention features a device for non-thermal tissue ablation including a skin-penetrating component and a mechanism for removing ablated tissue.

In one aspect, the invention features an apparatus for non-thermal tissue ablation having a main body configured for handheld operation, a tip (e.g., in the form of a detachable cartridge) including a skin-penetrating component with one or more ablation members (e.g., needles (e.g., hollow coring needles), drill bits, abrading elements, punches, and/or blades) configured for penetration into and retraction from skin, and, optionally, a pressure generating source. The ablation members may be configured to penetrate into the skin to a depth in the range of about 0.01 mm to about 15 mm and/or to produce an ablated tissue portion that results in the removal of an area or volumetric fraction of tissue (e.g., skin) in the range of about 5% to about 70%. If the pressure generating source is present, the ablation members are configured to be in fluid communication therewith (e.g., the ablation members can be connected, e.g., via one or more connectors, such as a tube, to the pressure generating source). The tip may be detachably attached to the main body. The pressure generating source, if present, may be a source of high or low pressure and may, for example, be disposed within the main body of the apparatus. For example, the pressure generating source may produce vacuum or suction to convey one or more ablated tissue portions produced by the one or more ablation members (e.g., needles, such as hollow coring needles) through the ablation members and away from the skin or proximal tissue layer or it may produce a force that injects a fluid (e.g., including one or more of a therapeutic agent, saline, a filler, and other material) into the skin or proximal tissue layers. The pressure generating source, if present, may remove waste materials (e.g., tissue, blood, and/or interstitial fluids) from one or more ablation members to prevent clogging, facilitate detachment of ablated tissue portions from surrounding tissue in a treatment area, and/or remove waste materials from a treatment area. In some embodiments, the apparatus may additionally include a reservoir for collecting waste materials. The reservoir may be disposed within the tip or main body of the apparatus or it may be separate from the apparatus. The reservoir may also be configured to be in fluid communication with the ablation members of the tip. In an embodiment, the pressure generating source is configured to exert force that conveys one or more ablated tissue portions produced by the one or more ablation members through the ablation members and into the reservoir.

In a second aspect, the invention features an apparatus for non-thermal tissue ablation having a main body configured for handheld operation, a tip (e.g., in the form of a detachable cartridge) including a skin-penetrating component with one or more ablation members (e.g., needles (e.g., hollow coring needles), drill bits, abrading elements, punches, and/or blades) configured for penetration into and retraction from skin, and a reservoir for collecting waste materials (e.g., tissue, blood, and/or interstitial fluids), in which the needles are configured to be in fluid communication with the reservoir. The ablation members may be configured to penetrate into the skin to a depth in the range of about 0.01 mm to about 15 mm and/or to produce an ablated tissue portion that results in the removal of an area or volumetric fraction of tissue (e.g., skin) in the range of about 5% to about 70%. The tip may be detachably attached to the main body. The reservoir may be disposed within the tip or main body of the apparatus or it may be separate from the apparatus. The apparatus may further include a pressure generating source that is a source of high or low pressure and may be disposed within the main body of the apparatus. For example, the pressure generating source may produce vacuum or suction to convey one or more ablated tissue portions produced by the one or more ablation members (e.g., needles, such as hollow coring needles) through the ablation members and into the reservoir or it may produce a force that injects a fluid (e.g., including one or more of a therapeutic agent, saline, a filler, and other material) into the skin or proximal tissue layers. The pressure generating source may remove waste materials from one or more ablation members to prevent clogging, facilitate detachment of ablated tissue portions from surrounding tissue in a treatment area, and/or remove waste materials from a treatment area.

In a third aspect, the invention features an apparatus for non-thermal tissue ablation having a main body configured for handheld operation and a tip (e.g., in the form of a detachable cartridge) including a skin-penetrating component with one or more ablation members (e.g., needles (e.g., hollow coring needles), drill bits, abrading elements, punches, and/or blades) configured for penetration into and retraction from skin, in which the tip is detachably attached to the main body. The ablation members may be configured to penetrate into the skin to a depth in the range of about 0.01 mm to about 15 mm and/or to produce an ablated tissue portion that results in the removal of an area or volumetric fraction of tissue (e.g., skin) in the range of about 5% to about 70%. The ablation members may further be configured to be in fluid communication with a pressure generating source (e.g., the ablation members can be connected, e.g., via one or more connectors, such as a tube, to the pressure generating source). For example, the pressure generating source may produce vacuum or suction to convey one or more ablated tissue portions produced by the one or more ablation members (e.g., needles, such as hollow coring needles) through the ablation members and away from the skin surface or it may produce a force that injects a fluid (e.g., including one or more of a therapeutic agent, saline, a filler, and other material) into the skin or proximal tissue layers. The pressure generating source may remove waste materials (e.g., tissue, blood, and/or interstitial fluids) from one or more ablation members to prevent clogging, facilitate detachment of ablated tissue portions from surrounding tissue in a treatment area, and/or remove waste materials from a treatment area.

In a fourth aspect, the invention features a system for non-thermal tissue ablation including an apparatus of the invention (e.g., an apparatus of the first, second, and third aspects, and any apparatus described herein) and a reservoir for collecting waste materials (e.g., tissue, blood, and/or interstitial fluids) that is in fluid communication with the apparatus. The system may further have a base unit (e.g., a dock, computer, control center, and/or charging station) and/or a pressure generating source. The reservoir may be disposed within the tip, the main body, the base unit (if present), or a separate module, or it may be external to these components. A pressure generating source may be a source of high or low pressure (e.g., a vacuum pump or fluid jet), and may be disposed within the main body or the base unit (if present), or it may be separate from the system. For example, the ablation members (e.g., needles, such as hollow coring needles), reservoir, and pressure generating source may be in fluid communication such that generation of vacuum by the pressure generating source draws ablated tissue portions produced by the one or more ablation members through the ablation members and into the reservoir.

In a fifth aspect, the invention features a kit for non-thermal tissue ablation including an apparatus or system of the invention (e.g., an apparatus of the first, second, third, and fourth aspects, and any apparatus described herein) having a main body configured for handheld operation and a tip (e.g., a cartridge) including a skin-penetrating component with one or more ablation members (e.g., needles (e.g., hollow coring needles), drill bits, abrading elements, punches, and/or blades), in which the tip is detachably attached to the main body and the ablation members are configured to be in fluid communication with a pressure generating source. The kit may further include a reservoir for collecting waste materials (e.g., tissue, blood, and/or interstitial fluids) that is configured to be in fluid communication with the ablation members. For example, a pressure generating source may provide vacuum or suction to draw one or more ablated tissue portions produced by one or more ablation members (e.g., needles, such as hollow coring needles) through the ablation members and into the reservoir. The kit may include the pressure generating source that may be a source of high or low pressure (e.g., a vacuum pump or fluid jet). The kit may also feature a base unit (e.g., a dock, computer, control center, and/or charging station). The reservoir may be disposed within the tip, the main body, the base unit (if present), or a separate module, or it may be external to these components. The pressure generating source may be disposed within the main body or the base unit (if present), or it may be external to these components.

In some embodiments, the main body and/or base unit may further include one or more user interfaces (e.g., one or more buttons, toggles, spin-wheels, dials, cursors, screws, keys, screens, touch screens, computers, displays, and/or switches) that may include indicators of device configurations, powered status, and/or other information including operation mode and needle number and arrangement. The user interface(s) of the main body and/or base unit may allow for control of device parameters, operation mode, and other features.

In some embodiments, the base unit of a system or kit includes a power source (e.g., one or more alternators, generators, power cords, connections to mains electricity, and/or battery charging stations). In some embodiments, the base unit is electrically coupled to the apparatus. The base unit may be coupled to the apparatus via a cable that provides power, information, fluid flow, and/or vacuum or suction. In other embodiments, the base unit may be wirelessly coupled to the apparatus.

In some embodiments, systems and kits of the invention additionally include a positioning apparatus for positioning skin (e.g., tensioning rods, adhesives, vacuum grippers, and needle or hook grippers).

In some embodiments, the skin-penetrating component of the apparatus includes 1-100 ablation members (e.g., needles (e.g., hollow coring needles), drill bits, abrading elements, punches, and/or blades) (e.g., 1-10, 1-20, 1-30, 1-40, 1-50, 1-60, 1-70, 1-80, 1-90, 1-100, 3-10, 3-20, 3-30, 3-40, 3-50, 3-60, 3-70, 3-80, 3-90, 3-100, 5-10, 5-20, 5-30, 5-40, 5-50, 5-60, 5-70, 5-80, 5-90, 5-100, 10-20, 10-40, 10-60, 10-80, 10-100, 20-40, 20-60, 20-80, 20-100, 40-60, 40-80, 40-100, 60-80, 60-100, and 80-100 needles). In some embodiments, 3-50 ablation members may be present. The ablation members may be arranged in a 1- or 2-dimensional array. In some embodiments, the minimum distance between ablation members may be between about 0.1 mm to about 50 mm (e.g., from 0.1 mm to 0.2 mm, 0.1 mm to 0.5 mm, 0.1 mm to 1 mm, 0.1 mm to 2 mm, 0.1 mm to 5 mm, 0.1 mm to 10 mm, 0.1 mm to 15 mm, 0.1 mm to 20 mm, 0.1 mm to 30 mm, 0.1 mm to 40 mm, 0.1 mm to 50 mm, 0.2 mm to 0.5 mm, 0.2 mm to 1 mm, 0.2 mm to 2 mm, 0.2 mm to 5 mm, 0.2 mm to 10 mm, 0.2 mm to 15 mm, 0.2 mm to 20 mm, 0.2 mm to 30 mm, 0.2 mm to 40 mm, 0.2 mm to 50 mm, 0.5 mm to 1 mm, 0.5 mm to 2 mm, 0.5 mm to 5 mm, 0.5 mm to 10 mm, 0.5 mm to 15 mm, 0.5 mm to 20 mm, 0.5 mm to 30 mm, 0.5 mm to 40 mm, 0.5 mm to 50 mm, 1 mm to 2 mm, 1 mm to 5 mm, 1 mm to 10 mm, 1 mm to 15 mm, 1 mm to 20 mm, 1 mm to 30 mm, 1 mm to 40 mm, 1 mm to 50 mm, 2 mm to 5 mm, 2 mm to 10 mm, 2 mm to 15 mm, 2 mm to 20 mm, 2 mm to 30 mm, 2 mm to 40 mm, 2 mm to 50 mm, 5 mm to 10 mm, 5 mm to 15 mm, 5 mm to 20 mm, 5 mm to 30 mm, 5 mm to 40 mm, 5 mm to 50 mm, 10 mm to 15 mm, 10 mm to 20 mm, 10 mm to 30 mm, 10 mm to 40 mm, 10 mm to 50 mm, 15 mm to 20 mm, 15 mm to 30 mm, 15 mm to 40 mm, 15 mm to 50 mm, 20 mm to 30 mm, 20 mm to 40 mm, 20 mm to 50 mm, 30 mm to 40 mm, 30 mm to 50 mm, and 40 mm to 50 mm). In some embodiments, the minimum distance between ablation members is about 0.5 mm to about 2 mm apart. The minimum distance between ablation members may correspond to the minimal size of the array of a plurality of ablation members. For example, an array including 10 ablation members each spaced about 1 mm apart may form a 1-dimensional array that is about 10 mm long or a 2-dimensional array arranged as 2 ablation members by 5 ablation members that is about 2 mm wide and about 5 mm long. The size of an array may correspond to the size of a skin region (e.g., a treatment area). For example, a 2 mm by 5 mm array may be used on a 2 mm by 5 mm treatment area. The skin-penetrating component may be applied more than one time to treat a larger region of skin. For example, a skin-penetrating component including a 2 mm by 5 mm array of ablation members may be applied three times to treat a 6 mm by 5 mm skin region.

In some embodiments, one or more (e.g., all of) the ablation members may be hollow needles (e.g., hollow coring needles). One or more of the needles may have one or more holes (e.g., at one or both ends or along the shaft of the needle). The needles may be made of metal or plastic and/or may be sharpened at one end. In some embodiments, the needles may be of any gauge between 19 and 26 (e.g., 19, 20, 21, 22, 23, 24, 25, and 26 gauge). In some embodiments, the needles may be 22 or 24 gauge needles.

The apparatus, system, or kit may be used to produce one or more tissue portions. For example, penetration into tissue by the ablation members (e.g., needles, drill bits, abrading elements, punches, and/or blades) of the apparatus may produce one or more tissue portions that are separated from the surrounding tissue. Retraction of the ablation members from tissue may facilitate the separation of the tissue portions from the surrounding tissue, and/or may allow treatment of another area of tissue. The number of tissue portions produced may correspond to the number of ablation members used. For instance, penetration into and retraction from tissue by a single ablation member (e.g., a hollow coring needle) may produce a single tissue portion, while penetration into and retraction from tissue by ten ablation members may produce ten tissue portions. Similarly, a single ablation member used ten times may produce ten tissue portions. A tissue portion produced by the apparatus may have specific dimensions. For example, the depth of penetration by the ablation members (e.g., hollow coring needles) may correspond to the depth or length of a tissue portion produced. In some embodiments, a tissue portion has at least one dimension in a range of about 10 µm to about 2 mm (e.g., about 10 µm to 500 µm, about 10 µm to 100 µm, 10 µm to 250 µm, 10 µm to 500 µm, 10 µm to 750 µm, 10 µm to 1 mm, 10 µm to 1.5 mm, 10 µm to 2 mm, about 50 µm to 100 µm, 50 µm to 250 µm, 50 µm to 500 µm, 50 µm to 750 µm, 50 µm to 1 mm, 50 µm to 1.5 mm, 50 µm to 2 mm, 100 µm to 250 µm, 100 µm to 500 µm, 100 µm to 750 µm, 100 µm to 1 mm, 100 µm to 1.5 mm, 100 µm to 2 mm, 250 µm to 500 µm, 250 µm to 750 µm, 250 µm to 1 mm, 250 µm to 1.5 mm, 250 µm to 2 mm, 500 µm to 750 µm, 500 µm to 1 mm, 500 µm to 1.5 mm, 500 µm to 2 mm, 750 µm to 1 mm, 750 µm to 1.5 mm, and 750 µm to 2 mm); between about 0.1 mm to about 0.8 mm (e.g., 0.1 mm to 0.8 mm, 0.1 mm to 0.6 mm, 0.1 mm to 0.4 mm, 0.1 mm to 0.2 mm, 0.2 mm to 0.8 mm, 0.2 mm to 0.6 mm, 0.2 mm to 0.4 mm, 0.2 mm to 0.3 mm, 0.3 mm to 0.8 mm, 0.3 mm to 0.6 mm, 0.3 mm to 0.4 mm, 0.4 mm to 0.8 mm, 0.4 mm to 0.6 mm, 0.4 mm to 0.5 mm, 0.5 mm to 0.8 mm, 0.5 mm to 0.6 mm, 0.6 mm to 0.8 mm, 0.6 mm to 0.7 mm, and 0.7 mm to 0.8 mm); between about 0.9 mm to about 20 mm (e.g., 0.9 mm to 20 mm, 0.9 mm to 17 mm, 0.9 mm to 14 mm, 0.9 mm to 11 mm, 0.9 mm to 8 mm, 0.9 mm to 5 mm, 0.9 mm to 3 mm, 3 mm to 20 mm, 3 mm to 17 mm, 3 mm to 14 mm, 3 mm to 11 mm, 3 mm to 8 mm, 3 mm to 5 mm, 5 mm to 20 mm, 5 mm to 17 mm, 5 mm to 14 mm, 5 mm toll mm, 5 mm to 8 mm, 8 mm to 20 mm, 8 mm to 17 mm, 8 mm to 14 mm, 8 mm to 11 mm, 11 mm to 20 mm, 11 mm to 17 mm, 11 mm to 14 mm, 14 mm to 20 mm, 14 mm to 17 mm, and 17 mm to 20 mm); between about 0.01 mm to 0.25 mm (e.g., 0.01 mm to 0.25 mm, 0.02 mm to 0.25 mm, 0.03 mm to 0.25 mm, 0.05 mm to 0.25 mm, 0.075 mm to 0.25 mm, 0.1 mm to 0.25 mm, 0.15 mm to 0.25 mm, 0.2 mm to 0.25 mm, 0.01 mm to 0.2 mm, 0.02 mm to 0.2 mm, 0.03 mm to 0.2 mm, 0.05 mm to 0.2 mm, 0.075 mm to 0.2 mm, 0.1 mm to 0.2 mm, 0.15 mm to 0.2 mm, 0.01 mm to 0.15 mm, 0.02 mm to 0.15 mm, 0.03 mm to 0.15 mm, 0.05 mm to 0.15 mm, 0.075 mm to 0.15 mm, 0.1 mm to 0.15 mm, 0.01 mm to 0.1 mm, 0.02 mm to 0.1 mm, 0.03 mm to 0.1 mm, 0.05 mm to 0.1 mm, 0.075 mm to 0.1 mm, 0.01 mm to 0.075 mm, 0.02 mm to 0.075 mm, 0.03 mm to 0.075 mm, 0.05 mm to 0.075 mm, 0.01 mm to 0.05 mm, 0.02 mm to 0.05 mm, 0.03 mm to 0.05 mm, 0.01 mm to 0.03 mm, 0.02 mm to 0.03 mm, 0.03 mm to 0.03 mm, 0.01 mm to 0.03 mm, 0.02 mm to 0.03 mm, and 0.01 mm to 0.02 mm); between about 0.01 mm to about 20 mm (e.g., 0.01 mm to 1 mm, 0.01 mm to 2 mm, 0.01 mm to 5 mm, 0.01 mm to 10 mm, 0.01 mm to 15 mm, 0.05 mm to 1 mm, 0.05 mm to 2 mm, 0.05 mm to 5 mm, 0.05 mm to 10 mm, 0.05 mm to 15 mm, 0.05 mm to 20 mm, 0.1 mm to 1 mm, 0.1 mm to 2 mm, 0.1 mm to 5 mm, 0.1 mm to 10 mm, 0.1 mm to 15 mm, 0.1 mm to 20 mm, 0.5 mm to 1 mm, 0.5 mm to 2 mm, 0.5 mm to 5 mm, 0.5 mm to 10 mm, 0.5 mm to 15 mm, 0.5 mm to 20 mm, 1 mm to 2 mm, 1 mm to 5 mm, 1 mm to 10 mm, 1 mm to 15 mm, 1 mm to 20 mm, 2 mm to 5 mm, 2 mm to 10 mm, 2 mm to 15 mm, 2 mm to 20 mm, 5 mm to 10 mm, 5 mm to 15 mm, and 5 mm to 20 mm); or between about 0.01 mm to about 2 mm (e.g., 0.01 mm to 0.1 mm, 0.01 mm to 0.5 mm, 0.01 mm to 1 mm, 0.01 mm to 1.5 mm, 0.01 mm to 1.75 mm, 0.05 mm to 0.1 mm, 0.05 mm to 0.5 mm, 0.05 mm to 1 mm, 0.05 mm to 1.5 mm, 0.05 mm to 1.75 mm, 0.05 mm to 2 mm, 0.1 mm to 0.5 mm, 0.1 mm to 1 mm, 0.1 mm to 1.5 mm, 0.1 mm to 1.75 mm, 0.1 mm to 2 mm, 0.3 mm to 0.5 mm, 0.3 mm to 1 mm, 0.3 mm to 1.5 mm, 0.3 mm to 1.75 mm, 0.3 mm to 2 mm, 0.5 mm to 1 mm, 0.5 mm to 1.5 mm, 0.5 mm to 1.75 mm, 0.5 mm to 2 mm, 0.7 mm to 1 mm, 0.7 mm to 1.5 mm, 0.7 mm to 1.75 mm, 0.7 mm to 2 mm, 1 mm to 1.5 mm, 1 mm to 1.75 mm, 1 mm to 2 mm, 1.5 mm to 1.75 mm, 1.5 mm to 2 mm, and 1.75 mm to 2 mm).

In some embodiments, a tissue portion produced by an ablation member (e.g., needle, drill bit, abrading element, punch, and blade) of the apparatus has an area dimension less than about 2 mm$^2$ and/or a volumetric dimension that is less than about 6 mm$^3$. A tissue portion may have an area dimension in a range of about 0.001 mm$^2$ to about 2 mm$^2$ (e.g., 0.001 mm$^2$ to 0.005 mm$^2$, 0.001 mm$^2$ to 0.01 mm$^2$, 0.001 mm$^2$ to 0.05 mm$^2$, 0.001 mm$^2$ to 0.1 mm$^2$, 0.001 mm$^2$ to 0.5 mm$^2$, 0.001 mm$^2$ to 1 mm$^2$, 0.001 mm$^2$ to 1.5 mm$^2$, 0.001 mm$^2$ to 2 mm$^2$, 0.005 mm$^2$ to 0.01 mm$^2$, 0.005 mm$^2$ to 0.05 mm$^2$, 0.005 mm$^2$ to 0.1 mm$^2$, 0.005 mm$^2$ to 0.5 mm$^2$, 0.005 mm² to 1 mm², 0.005 mm² to 1.5 mm², 0.005 mm² to 2 mm², 0.01 mm² to 0.02 mm², 0.01 mm² to 0.05 mm², 0.01 mm² to 0.1 mm², 0.01 mm² to 0.5 mm², 0.01 mm² to 1 mm², 0.01 mm² to 1.5 mm², 0.01 mm² to 2 mm², 0.05 mm² to 0.1 mm², 0.05 mm² to 0.5 mm², 0.05 mm² to 1 mm², 0.05 mm² to 1.5 mm², 0.05 mm² to 2 mm², 0.1 mm² to 0.2 mm², 0.1 mm² to 0.5 mm², 0.1 mm² to 1 mm², 0.1 mm² to 1.5 mm², 0.1 mm² to 2 mm², 0.5 mm² to 1 mm², 0.5 mm² to 1.5 mm², 0.5 mm² to 2 mm², 1 mm² to 1.5 mm², 1 mm² to 2 mm², and 1.5 mm² to 2 mm²).

In some embodiments, the volume of a tissue portion formed by use of the apparatus is between about 0.001 mm³ and about 6 mm³ (e.g., 0.001 mm³ to 0.01 mm³, 0.001 mm³ to 0.1 mm³, 0.001 mm³ to 0.5 mm³, 0.001 mm³ to 1 mm³, 0.001 mm³ to 2 mm³, 0.001 mm³ to 3 mm³, 0.001 mm³ to 4 mm³, 0.001 mm³ to 5 mm³, 0.001 mm³ to 6 mm³, 0.005 mm³ to 0.01 mm³, 0.005 mm³ to 0.1 mm³, 0.005 mm³ to 0.5 mm³, 0.005 mm³ to 1 mm³, 0.005 mm³ to 2 mm³, 0.005 mm³ to 3 mm³, 0.005 mm³ to 4 mm³, 0.005 mm³ to 5 mm³, 0.005 mm³ to 6 mm³, 0.01 mm³ to 0.1 mm³, 0.01 mm³ to 0.5 mm³, 0.01 mm³ to 1 mm³, 0.01 mm³ to 2 mm³, 0.01 mm³ to 3 mm³, 0.01 mm³ to 4 mm³, 0.01 mm³ to 5 mm³, 0.01 mm³ to 6 mm³, 0.1 mm³ to 0.5 mm³, 0.1 mm³ to 1 mm³, 0.1 mm³ to 2 mm³, 0.1 mm³ to 3 mm³, 0.1 mm³ to 4 mm³, 0.1 mm³ to 5 mm³, 0.1 mm³ to 6 mm³, 0.5 mm³ to 1 mm³, 0.5 mm³ to 2 mm³, 0.5 mm³ to 3 mm³, 0.5 mm³ to 4 mm³, 0.5 mm³ to 5 mm³, 0.5 mm³ to 6 mm³, 1 mm³ to 2 mm³, 1 mm³ to 3 mm³, 1 mm³ to 4 mm³, 1 mm³ to 5 mm³, 1 mm³ to 6 mm³, 2 mm³ to 3 mm³, 2 mm³ to 4 mm³, 2 mm³ to 5 mm³, 2 mm³ to 6 mm³, 3 mm³ to 4 mm³, 3 mm³ to 5 mm³, 3 mm³ to 6 mm³, 4 mm³ to 5 mm³, 4 mm³ to 6 mm³, and 5 mm³ to 6 mm³).

In some embodiments, the dimensions, geometry, number, and other characteristics of a tissue portion may correspond to the dimensions, geometry, number, and other characteristics of an ablation member (e.g., needle, drill bit, abrading element, punch, and blade) of the skin penetrating component of the apparatus of the invention. For example, the use of an apparatus of the invention may form one or more holes in a region of skin and/or proximal tissue layers (e.g., a treatment area) by producing one or more tissue portions with the dimensions, geometry, and other characteristics of the holes. The diameter and/or width of a tissue portion may be between about 0.01 mm to about 2 mm (e.g., as described herein). The diameter and/or width of a tissue portion generally correspond to the diameter and/or width of an ablation member of the invention used to produce the tissue portion. The diameter and/or width of an ablation member of an apparatus of the invention at its widest points may be about 0.01 mm to about 2 mm (e.g., as described herein). For example, an apparatus including hollow coring needles with inner (lumen) diameters in the range of about 0.01 mm to about 2.0 mm can be used to provide tissue portions having a corresponding diameter in the range of about 0.01 mm to about 2.0 mm, respectively.

An apparatus of the invention may be configured to provide one or more tissue portions having a change in width as a function of depth (e.g., length). For example, the outer structure and/or inner structure (e.g., for a hollow ablation member) of one or more ablation members (e.g., needles, such as hollow coring needles) of the apparatus may be tapered, having a narrower width at either end, and/or may vary regularly or irregularly along their lengths and so may produce one or more tissue portions having a narrower width at one end and/or regularly or irregularly varying widths along their lengths. The change in width of a tissue portion may be between about 100 μm to about 500 μm as a function of depth (e.g., 100 μm to 200 μm, 100 μm to 300 μm, 100 μm to 400 μm, 100 μm to 500 μm, 200 μm to 300 μm, 200 μm to 400 μm, 200 μm to 500 μm, 300 μm to 400 μm, 300 μm to 500 μm, and 400 μm to 500 μm). The width to depth ratio of a tissue portion may be between about 1:0.3 to about 1:75. For example, the width to depth radio of a tissue portion may be between about 1:0.3 to about 1:1 (e.g., 1:0.3 to 1:1, 1:0.35 to 1:1, 1:0.4 to 1:1, 1:0.45 to 1:1, 1:0.5 to 1:1, 1:0.55 to 1:1, 1:0.6 to 1:1, 1:0.65 to 1:1, 1:0.7 to 1:1, 1:0.75 to 1:1, 1:0.8 to 1:1, 1:0.85 to 1:1, 1:0.9 to 1:1, 1:0.95 to 1:1, 1:0.3 to 1:0.95, 1:0.35 to 1:0.95, 1:0.4 to 1:0.95, 1:0.45 to 1:0.95, 1:0.5 to 1:0.95, 1:0.55 to 1:0.95, 1:0.6 to 1:0.95, 1:0.65 to 1:0.95, 1:0.7 to 1:0.95, 1:0.75 to 1:0.95, 1:0.8 to 1:0.95, 1:0.85 to 1:0.95, 1:0.9 to 1:0.95, 1:0.3 to 1:0.9, 1:0.35 to 1:0.9, 1:0.4 to 1:0.9, 1:0.45 to 1:0.9, 1:0.5 to 1:0.9, 1:0.55 to 1:0.9, 1:0.6 to 1:0.9, 1:0.65 to 1:0.9, 1:0.7 to 1:0.9, 1:0.75 to 1:0.9, 1:0.8 to 1:0.9, 1:0.85 to 1:0.9, 1:0.3 to 1:0.85, 1:0.35 to 1:0.85, 1:0.4 to 1:0.85, 1:0.45 to 1:0.85, 1:0.5 to 1:0.85, 1:0.55 to 1:0.85, 1:0.6 to 1:0.85, 1:0.65 to 1:0.85, 1:0.7 to 1:0.85, 1:0.75 to 1:0.85, 1:0.8 to 1:0.85, 1:0.3 to 1:0.8, 1:0.35 to 1:0.8, 1:0.4 to 1:0.8, 1:0.45 to 1:0.8, 1:0.5 to 1:0.8, 1:0.55 to 1:0.8, 1:0.6 to 1:0.8, 1:0.65 to 1:0.8, 1:0.7 to 1:0.8, 1:0.75 to 1:0.8, 1:0.3 to 1:0.75, 1:0.35 to 1:0.75, 1:0.4 to 1:0.75, 1:0.45 to 1:0.75, 1:0.5 to 1:0.75, 1:0.55 to 1:0.75, 1:0.6 to 1:0.75, 1:0.65 to 1:0.75, 1:0.7 to 1:0.75, 1:0.3 to 1:0.65, 1:0.35 to 1:0.65, 1:0.4 to 1:0.65, 1:0.45 to 1:0.65, 1:0.5 to 1:0.65, 1:0.55 to 1:0.65, 1:0.6 to 1:0.65, 1:0.3 to 1:0.65, 1:0.35 to 1:0.65, 1:0.4 to 1:0.65, 1:0.45 to 1:0.65, 1:0.5 to 1:0.65, 1:0.55 to 1:0.65, 1:0.6 to 1:0.65, 1:0.3 to 1:0.6, 1:0.35 to 1:0.6, 1:0.4 to 1:0.6, 1:0.45 to 1:0.6, 1:0.5 to 1:0.6, 1:0.55 to 1:0.6, 1:0.3 to 1:0.55, 1:0.35 to 1:0.55, 1:0.4 to 1:0.55, 1:0.45 to 1:0.55, 1:0.5 to 1:0.55, 1:0.3 to 1:0.5, 1:0.35 to 1:0.5, 1:0.4 to 1:0.5, 1:0.45 to 1:0.5, 1:0.5 to 1:0.5, 1:0.3 to 1:0.45, 1:0.35 to 1:0.45, 1:0.4 to 1:0.45, 1:0.3 to 1:0.4, 1:0.35 to 1:0.4, and 1:0.3 to 1:0.35); between about 1:1 to about 1:20 (e.g., 1:1 to 1:2, 1:1 to 1:3, 1:1 to 1:4, 1:1 to 1:5, 1:1 to 1:6, 1:1 to 1:7, 1:1 to 1:8, 1:1 to 1:9, 1:1 to 1:10, 1:1 to 1:11, 1:1 to 1:12, 1:1 to 1:13, 1:1 to 1:14, 1:1 to 1:15, 1:1 to 1:16, 1:1 to 1:17, 1:1 to 1:18, 1:1 to 1:19, 1:1 to 1:20, 1:2 to 1:3, 1:2 to 1:4, 1:2 to 1:5, 1:2 to 1:6, 1:2 to 1:7, 1:2 to 1:8, 1:2 to 1:9, 1:2 to 1:10, 1:2 to 1:11, 1:2 to 1:12, 1:2 to 1:13, 1:2 to 1:14, 1:2 to 1:15, 1:2 to 1:16, 1:2 to 1:17, 1:2 to 1:18, 1:2 to 1:19, 1:2 to 1:20, 1:3 to 1:4, 1:3 to 1:5, 1:3 to 1:6, 1:3 to 1:7, 1:3 to 1:8, 1:3 to 1:9, 1:3 to 1:10, 1:3 to 1:11, 1:3 to 1:12, 1:3 to 1:13, 1:3 to 1:14, 1:3 to 1:15, 1:3 to 1:16, 1:3 to 1:17, 1:3 to 1:18, 1:3 to 1:19, 1:3 to 1:20, 1:4 to 1:5, 1:4 to 1:6, 1:4 to 1:7, 1:4 to 1:8, 1:4 to 1:9, 1:4 to 1:10, 1:4 to 1:11, 1:4 to 1:12, 1:4 to 1:13, 1:4 to 1:14, 1:4 to 1:15, 1:4 to 1:16, 1:4 to 1:17, 1:4 to 1:18, 1:4 to 1:19, 1:4 to 1:20, 1:5 to 1:6, 1:5 to 1:7, 1:5 to 1:8, 1:5 to 1:9, 1:5 to 1:10, 1:5 to 1:11, 1:5 to 1:12, 1:5 to 1:13, 1:5 to 1:14, 1:5 to 1:15, 1:5 to 1:16, 1:5 to 1:17, 1:5 to 1:18, 1:5 to 1:19, 1:5 to 1:20, 1:6 to 1:7, 1:6 to 1:8, 1:6 to 1:9, 1:6 to 1:10, 1:6 to 1:11, 1:6 to 1:12, 1:6 to 1:13, 1:6 to 1:14, 1:6 to 1:15, 1:6 to 1:16, 1:6 to 1:17, 1:6 to 1:18, 1:6 to 1:19, 1:6 to 1:20, 1:7 to 1:8, 1:7 to 1:9, 1:7 to 1:10, 1:7 to 1:11, 1:7 to 1:12, 1:7 to 1:13, 1:7 to 1:14, 1:7 to 1:15, 1:7 to 1:16, 1:7 to 1:17, 1:7 to 1:18, 1:7 to 1:19, 1:7 to 1:20, 1:8 to 1:9, 1:8 to 1:10, 1:8 to 1:11, 1:8 to 1:12, 1:8 to 1:13, 1:8 to 1:14, 1:8 to 1:15, 1:8 to 1:16, 1:8 to 1:17, 1:8 to 1:18, 1:8 to 1:19, 1:8 to 1:20, 1:9 to 1:10, 1:9 to 1:11, 1:9 to 1:12, 1:9 to 1:13, 1:9 to 1:14, 1:9 to 1:15, 1:9 to 1:16, 1:9 to 1:17, 1:9 to 1:18, 1:9 to 1:19, 1:9 to 1:20, 1:10 to 1:11, 1:10 to 1:12, 1:10 to 1:13, 1:10 to 1:14, 1:10 to 1:15, 1:10 to 1:16, 1:10 to 1:17, 1:10 to 1:18, 1:10 to 1:19, 1:10 to 1:20, 1:11 to 1:12, 1:11 to 1:13, 1:11 to 1:14, 1:11 to 1:15, 1:11 to 1:16, 1:11 to 1:17, 1:11 to 1:18, 1:11 to 1:19, 1:11 to 1:20, 1:12 to 1:13, 1:12 to 1:14, 1:12 to 1:15, 1:12 to 1:16, 1:12 to 1:17, 1:12 to 1:18, 1:12 to 1:19, 1:12 to 1:20, 1:13 to 1:14, 1:13 to 1:15, 1:13 to 1:16, 1:13 to 1:17, 1:13 to 1:18, 1:13 to 1:19, 1:13 to 1:20, 1:14 to 1:15, 1:14 to 1:16, 1:14 to 1:17, 1:14 to 1:18, 1:14 to 1:19, 1:14 to 1:20, 1:15 to 1:16, 1:15 to 1:17, 1:15 to 1:18, 1:15 to 1:19, 1:15 to 1:20, 1:17 to 1:18, 1:17 to 1:19, and 1:17 to 1:20); between about 1:1 to about 1:75 (e.g., 1:1 to 1:2, 1:1 to 1:5, 1:1 to 1:10, 1:1 to 1:20, 1:1 to 1:30, 1:1 to 1:40, 1:1 to 1:50, 1:1 to 1:60, 1:1 to 1:75, 1:2 to 1:5, 1:2 to 1:10, 1:2 to 1:20, 1:2 to 1:30, 1:2 to 1:40, 1:2 to 1:50, 1:2 to 1:60, 1:2 to 1:75, 1:5 to 1:10, 1:5 to 1:20, 1:5 to 1:30, 1:5 to 1:40, 1:5 to 1:50, 1:5 to 1:60, 1:5 to 1:75, 1:10 to 1:20, 1:10 to 1:30, 1:10 to 1:40, 1:10 to 1:50, 1:10 to 1:60, 1:10 to 1:75, 1:20 to 1:30, 1:20 to 1:40, 1:20 to 1:50, 1:20 to 1:60, 1:20 to 1:75, 1:30 to 1:40, 1:30 to 1:50, 1:30 to 1:60, 1:30 to 1:75, 1:40 to 1:50, 1:40 to 1:60, 1:40 to 1:75, 1:50 to 1:60, 1:50 to 1:75, and 1:60 to 1:75); between about 1:25 to about 1:75 (e.g., 1:25 to 1:75, 1:30 to 1:75, 1:35 to 1:75, 1:40 to 1:75, 1:45 to 1:75, 1:50 to 1:75, 1:55 to 1:75, 1:60 to 1:75, 1:65 to 1:75, 1:70 to 1:75, 1:25 to 1:70, 1:30 to 1:70, 1:35 to 1:70, 1:40 to 1:70, 1:45 to 1:70, 1:50 to 1:70, 1:55 to 1:70, 1:60 to 1:70, 1:65 to 1:70, 1:25 to 1:65, 1:30 to 1:65, 1:35 to 1:65, 1:40 to 1:65, 1:45 to 1:65, 1:50 to 1:65, 1:55 to 1:65, 1:60 to 1:65, 1:25 to 1:60, 1:30 to 1:60, 1:35 to 1:60, 1:40 to 1:60, 1:45 to 1:60, 1:50 to 1:60, 1:55 to 1:60, 1:25 to 1:55, 1:30 to 1:55, 1:35 to 1:55, 1:40 to 1:55, 1:45 to 1:55, 1:50 to 1:55, 1:25 to 1:50, 1:30 to 1:50, 1:35 to 1:50, 1:40 to 1:50, 1:45 to 1:50, 1:25 to 1:45, 1:30 to 1:45, 1:35 to 1:45, 1:40 to 1:45, 1:25 to 1:40, 1:30 to 1:40, 1:35 to 1:40, 1:25 to 1:35, 1:30 to 1:35, and 1:25 to 1:30); or between about 1:03 to about 1:75 (e.g., 1:0.3 to 1:0.5, 1:0.3 to 1:1, 1:0.3 to 1:2, 1:0.3 to 1:5, 1:0.3 to 1:10, 1:0.3 to 1:20, 1:0.3 to 1:30, 1:0.3 to 1:40, 1:0.3 to 1:50, 1:0.3 to 1:60, 1:0.3 to 1:75, 1:0.5 to 1:1, 1:0.5 to 1:2, 1:0.5 to 1:5, 1:0.5 to 1:10, 1:0.5 to 1:20, 1:0.5 to 1:30, 1:0.5 to 1:40, 1:0.5 to 1:50, 1:0.5 to 1:60, and 1:0.5 to 1:75).

In all aspects of the invention, the apparatus may be configured to provide from about 10 to about 10000 tissue portions per $cm^2$ area (e.g., 10 to 50, 10 to 100, 10 to 200, 10 to 300, 10 to 400, 10 to 500, 10 to 600, 10 to 700, 10 to 800, 10 to 900, 10 to 1000, 10 to 2000, 10 to 4000, 10 to 6000, 10 to 8000, 10 to 10000, 50 to 100, 50 to 200, 50 to 300, 50 to 400, 50 to 500, 50 to 600, 50 to 700, 50 to 800, 50 to 900, 50 to 1000, 50 to 2000, 50 to 4000, 510 to 6000, 50 to 8000, 50 to 10000, 100 to 200, 100 to 300, 100 to 400, 100 to 500, 100 to 600, 100 to 700, 100 to 800, 100 to 900, 100 to 1000, 100 to 2000, 100 to 4000, 100 to 6000, 100 to 8000, 100 to 10000, 200 to 300, 200 to 400, 200 to 500, 200 to 600, 200 to 700, 200 to 800, 200 to 900, 200 to 1000, 200 to 2000, 200 to 4000, 200 to 6000, 200 to 8000, 200 to 10000, 300 to 400, 300 to 500, 300 to 600, 300 to 700, 300 to 800, 300 to 900, 300 to 1000, 300 to 2000, 300 to 4000, 300 to 6000, 300 to 8000, 300 to 10000, 400 to 500, 400 to 600, 400 to 700, 400 to 800, 400 to 900, 400 to 1000, 400 to 2000, 400 to 4000, 400 to 6000, 400 to 8000, 400 to 10000, 500 to 600, 500 to 700, 500 to 800, 500 to 900, 500 to 1000, 500 to 2000, 500 to 4000, 500 to 6000, 500 to 8000, 500 to 10000, 600 to 700, 600 to 800, 600 to 900, 600 to 1000, 600 to 2000, 600 to 4000, 600 to 6000, 600 to 8000, 600 to 10000, 700 to 800, 700 to 900, 700 to 1000, 700 to 2000, 700 to 4000, 700 to 6000, 700 to 8000, 700 to 10000, 800 to 900, 800 to 1000, 800 to 2000, 800 to 4000, 800 to 6000, 800 to 8000, 800 to 10000, 900 to 1000, 900 to 2000, 900 to 4000, 900 to 6000, 900 to 8000, 900 to 10000, 1000 to 2000, 1000 to 4000, 1000 to 6000, 1000 to 8000, 1000 to 10000, 2000 to 4000, 2000 to 6000, 2000 to 8000, 2000 to 10000, 4000 to 6000, 4000 to 8000, 4000 to 10000, 6000 to 8000, 6000 to 10000, and 8000 to 10000 tissue portions per $cm^2$ area) of a skin region to which the apparatus is applied (e.g., a treatment area). The invention features an apparatus configured to remove about 5%-70% (e.g., 5%, 10%, 15%, 20%, 25%, 30%, 35%, 40%, 45%, 50%, 55%, 60%, 65%, and 70%) of tissue within a treatment area. In some embodiments, about 10% of tissue within a treatment area is removed by the apparatus. In an embodiment, the apparatus may be configured to remove about 10% of the tissue within a treatment area using 24 gauge needles. For example, penetration into and retraction from tissue within a treatment area by an array of 24 gauge hollow coring needles may result in the removal of about 10% of the tissue within the treatment area.

Any of the apparatuses, systems, and kits of the invention may further include an actuation mechanism for driving penetration into the skin by the ablation members (e.g., needles (e.g., hollow coring needles), drill bits, abrading elements, punches, and blades) of the skin-penetrating component. The actuation mechanism may be mechanically or electrically coupled to the ablation members. In some embodiments, the actuation mechanism is configured to allow penetration into the skin by the ablation members to a depth of about 0.1 mm to about 15 mm (e.g., 0.1 mm to 0.2 mm, 0.1 mm to 0.5 mm, 0.1 mm to 1 mm, 0.1 mm to 2 mm, 0.1 mm to 5 mm, 0.1 mm to 10 mm, 0.1 mm to 15 mm, 0.2 mm to 0.5 mm, 0.2 mm to 1 mm, 0.2 mm to 2 mm, 0.2 mm to 5 mm, 0.2 mm to 10 mm, 0.2 mm to 15 mm, 0.5 mm to 1 mm, 0.5 mm to 2 mm, 0.5 mm to 5 mm, 0.5 mm to 10 mm, 0.5 mm to 15 mm, 1 mm to 2 mm, 1 mm to 5 mm, 1 mm to 10 mm, 1 mm to 15 mm, 2 mm to 5 mm, 2 mm to 10 mm, 2 mm to 15 mm, 5 mm to 10 mm, 5 mm to 15 mm, and 10 mm to 15 mm). In some embodiments, the actuation mechanism is configured to allow penetration into the skin by the ablation members to a depth of about 10 mm to about 15 mm. In other embodiments, the actuation mechanism is configured to allow penetration into the skin by the ablation members to a depth of about 2 mm to about 5 mm. The actuation mechanism may be selected from the group consisting of a pneumatic actuator, an electromagnetic actuator, a motor with a cam, a piezoelectric actuator, and a motor with a lead screw (e.g., a stepper motor). The actuation mechanism may drive penetration of the needles into the skin with a force of about 0.5 N to about 20 N per needle (e.g., 0.5 N to 0.75 N, 0.5 N to 1 N, 0.5 N to 1.25 N, 0.5 N to 1.5 N, 0.5 N to 2 N, 0.5 N to 5 N, 0.5 N to 10 N, 0.5 N to 12 N, 0.5 N to 15 N, 0.5 N to 20 N, 0.75 N to 1 N, 0.75 N to 1.25 N, 0.75 N to 1.5 N, 0.75 N to 2 N, 0.75 N to 5 N, 0.75 N to 10 N, 0.75 N to 12 N, 0.75 N to 15 N, 0.75 N to 20 N, 1 N to 1.25 N, 1 N to 1.5 N, 1 N to 2 N, 1 N to 5 N, 1 N to 10 N, 1 N to 12 N, 1 N to 15 N, 1 N to 20 N, 1.25 N to 1.5 N, 1.25 N to 2 N, 1.25 N to 5 N, 1.25 N to 10 N, 1.25 N to 12 N, 1.25 N to 15 N, 1.25 N to 20 N, 1.5 N to 2 N, 1.5 N to 5 N, 1.5 N to 10 N, 1.5 N to 12 N, 1.5 N to 15 N, 1.5 N to 20 N, 2 N to 5 N, 2 N to 10 N, 2 N to 12 N, 2 N to 15 N, 2 N to 20 N, 5 N to 10 N, 5 N to 12 N, 5 N to 15 N, 5 N to 20 N, 10 N to 12 N, 10 N to 15 N, 10 N to 20 N, 12 N to 15 N, 12 N to 20 N, and 15 N to 20 N). The actuation mechanism may also drive retraction of the needles from the skin.

Any of the apparatuses, systems, and kits of the invention may further have an actuation or translation mechanism for driving the ablation members (e.g., needles (e.g., hollow coring needles), drill bits, abrading elements, punches, and blades) across the skin. A translation mechanism may include wheels (e.g., coupled to the main body and/or tip of the apparatus to permit wheels to translate across a skin surface). An actuation mechanism may be mechanically or electrically coupled to one or more ablation members. The actuation mechanism may be selected from the group consisting of a pneumatic actuator, an electromagnetic actuator, a motor with a cam, a piezoelectric actuator, and a motor with a lead screw (e.g., a stepper motor).

In some embodiments, the apparatuses, systems, and kits of the invention may further include a position detection mechanism (e.g., an optical tracking mechanism to guide manual translation of the apparatus across a skin surface). In apparatuses, systems, and kits having one or more actuation, translation, and/or position detection mechanisms, one or more activation mechanisms may activate the components. These activation mechanisms may include toggles, spinwheels, buttons, screws, switches, cursors, dials, and/or keys. Actuation, translation, position detection, and/or activation mechanisms may be disposed on or within the main body (e.g., on the user interface) or the tip of the apparatus or on or within a base unit (e.g., on the user interface), if present.

In some embodiments, the apparatus has a release mechanism for detaching the tip. In another embodiment, the tip is designed for a single use. Tips may have varying numbers of ablation members (e.g., needles, drill bits, abrading elements, punches, and blades) and ablation member configurations, and tips of varying ablation members and ablation member configurations may be detachably attachable to the main body of the apparatus.

In some embodiments, the apparatus is battery powered or is powered by a cord that can be plugged into an outlet (e.g., an outlet providing a standard mains power). When battery powered, the main body of the apparatus may have a release mechanism for gaining access to the battery (e.g., to replace a depleted battery and/or remove a battery for charging). Alternatively, the apparatus may have a battery that is built into the main body that is not designed to be replaceable.

The invention also features methods of treating a skin condition, which include a) forming a plurality of tissue portions by contacting the ablation members (e.g., needles (e.g., hollow coring needles), drill bits, abrading elements, punches, and blades) of any of the apparatuses or systems of the first-fourth aspects to the skin of a subject, and b) removing the resultant plurality of tissue portions from the skin. In an embodiment of the invention, penetration into the skin by the ablation members forms the plurality of tissue portions. The tissue portions may be removed from the ablation members and/or skin by the use of a pressure source (e.g., a vacuum applied, e.g., through the ablation members).

In some embodiments, the method of the invention may involve treatment of the dermis and/or epidermis. The method may involve treatment of the skin and/or proximal tissue layers. In some embodiments, the method of the invention may be used to treat one or more diseases, disorders, or conditions in underlying skin layers, such as fat, muscle, and facial SMAS (superficial muscular aponeurotic system). In such embodiments, the apparatus of the invention may include a skin-penetrating component configured to provide a tissue portion having an appropriate depth (e.g., 0.1-15 mm) to reach the targeted underlying skin layers (e.g., fat, muscle, and facial SMAS).

In any embodiment described herein, the apparatuses, systems, kits, and methods may be used to eliminate tissue volume or area of the skin and/or proximal tissue layers, promoting one or more of the following effects: tissue growth, skin tightening, skin rejuvenation, improved skin texture or appearance, decreased skin laxity, lifting of skin, skin repositioning, tattoo removal, and/or an expansion of tissue volume or area. In some embodiments, the devices, apparatuses, and methods are useful for treating one or more diseases, disorders, or conditions of the skin to improve skin appearance, to rejuvenate skin, and/or to tighten skin. Diseases, disorders, or conditions may include removal of pigment, veins (e.g., spider veins or reticular veins), glands (e.g., sebaceous glands or sweat glands), hair follicles, and/or vessels in the skin, as well as treatment of acne, allodynia, blemishes, ectopic dermatitis, hyperpigmentation, hyperplasia (e.g., lentigo or keratosis), loss of translucency, loss of elasticity, melasma (e.g., epidermal, dermal, or mixed subtypes), photodamage, rashes (e.g., erythematous, macular, papular, and/or bullous conditions), psoriasis, rhytides (or wrinkles, e.g., lateral canthal lines ("crow's feet"), age-related rhytides, sun-related rhytides, or heredity-related rhytides), sallow color, scar contracture (e.g., relaxation of scar tissue), scarring (e.g., due to acne, surgery, or other trauma), skin aging, skin contraction (e.g., excessive tension in the skin), skin irritation/sensitivity, skin laxity (e.g., loose or sagging skin or other skin irregularities), striae (or stretch marks), vascular lesions (e.g., angioma, erythema, hemangioma, papule, port wine stain, rosacea, reticular vein, or telangiectasia), or any other unwanted skin irregularities (e.g., areas of fibrosis and/or necrosis).

In other embodiments, the apparatuses, systems, kits, and methods described herein allow for treatment of uneven surfaces (e.g., the face). In particular, large area ablation techniques can be difficult to apply in a conformal or uniform manner to uneven skin surfaces. Thus, the apparatus is configured such that it can conform to the skin surface, even if the surface is uneven.

In some embodiments, a compressive force may be applied to the treatment area prior to treatment. The compressive force may be applied with the hands or with a positioning apparatus, which can be integrated into the main body of the apparatus or used as a standalone device.

In other embodiments, the apparatuses, systems, kits, and methods described herein allow for immediate assessment of the expected or approximate outcome of the treatment. In contrast to energy-based methods, the expected or approximate outcome of the treatment performed with the apparatus of the present invention can be immediately visible. For instance, treatment with conventional energy-based devices activates remodeling of the tissue and the end-result is only visible weeks to months after treatment. The outcome of treatment with the apparatus of the present invention may be assessed within minutes to hours to days after treatment as the treatment involves surgical removal of a portion of the skin.

In other embodiments, the apparatuses, systems, kits, and methods described herein allow for rapid healing. For instance, compared to surgery, the treatment can be much less invasive and the healing can be, therefore, much faster. In some embodiments, a non-compressive bandage may be applied to the skin after the removal of tissue portions to promote healing. In other embodiments, a bandage may be applied to promote healing in a preferred direction.

In some embodiments, the treatment results in a reduction of skin surface area. In particular, the reduction in skin surface area may occur in a direction orthogonal to Langer lines.

In some embodiments, the treatment may not leave lasting changes in the architecture of the skin such that the same skin region may be treated multiple times. Treatment of the same area multiple times may permit sequential tissue area and/or volume reduction without any adverse changes in skin architecture, function, or appearance. In contrast, treatment with energy-based methods results in changes at the ultrastructural level which are likely to be additive with each subsequent treatment, potentially limiting the number of times in which such a treatment can be applied.

Definitions

By "tissue portion" is meant that portion of skin and/or proximal tissue layers (e.g., fat, muscle, and/or facial superficial muscular aponeurotic system) that is ablated, cut, abraded, damaged, and/or removed (e.g., as a plug) by an ablation member (e.g., needle) of the apparatus. A tissue portion may have particular dimensions, geometry, and other characteristics that correspond to the particular dimensions, geometry, and other characteristics of an ablation member of the skin penetrating component of the invention.

By "about" is meant +/−10% of the recited value.

By "non-thermal tissue ablation" is meant a tissue ablation (e.g., destruction or removal) technique that does not transfer substantial thermal energy to the surrounding non-ablated tissue (e.g., as opposed to thermal and photo-thermal tissue ablation techniques, such as laser ablation techniques). For example, non-thermal tissue ablation does not produce a coagulation zone in tissue, or produces a substantially reduced (e.g., >90% reduction, as compared to thermal ablation techniques) coagulation zone in tissue, which can prevent and/or slow closure and/or healing of an ablated zone (e.g., a hole).

By "non-thermal ablation apparatus" is meant a device capable of performing non-thermal tissue ablation.

By "skin-penetrating component" is meant an element that includes one or more ablation members (e.g., needles, drill bits, abrading elements, punches, blades, fluid jets, and/or probes) that are capable of puncturing the skin. The skin-penetrating component may alone be capable of creating a tissue portion or, when combined with a pressure generating source, may be capable of producing a tissue portion.

By "subject" is meant a mammal (e.g., a human or non-human mammal).

By "treating" a disease, disorder, or condition in a subject is meant reducing at least one symptom of the disease, disorder, or condition, e.g., a skin condition, such as treatment of acne, allodynia, blemishes, ectopic dermatitis, hyperpigmentation, hyperplasia (e.g., lentigo or keratosis), loss of translucency, loss of elasticity, melasma (e.g., epidermal, dermal, or mixed subtypes), photodamage, rashes (e.g., erythematous, macular, papular, and/or bullous conditions), psoriasis, rhytides (or wrinkles, e.g., lateral canthal lines ("crow's feet"), age-related rhytides, sun-related rhytides, or heredity-related rhytides), sallow color, scar contracture (e.g., relaxation of scar tissue), scarring (e.g., due to acne, surgery, or other trauma), skin aging, skin contraction (e.g., excessive tension in the skin), skin irritation/sensitivity, skin laxity (e.g., loose or sagging skin or other skin irregularities), striae (or stretch marks), vascular lesions (e.g., angioma, erythema, hemangioma, papule, port wine stain, rosacea, reticular vein, or telangiectasia), irregular veins (e.g., spider veins or reticular veins), or any other unwanted skin irregularities (e.g., areas of fibrosis and/or necrosis, undesirable pigmentation, undesirable glands (e.g., sebaceous glands or sweat glands), hair follicles, and undesirable vessels).

Other features and advantages of the invention will be apparent from the following Detailed Description and the claims.

DETAILED DESCRIPTION

Figure 1A:
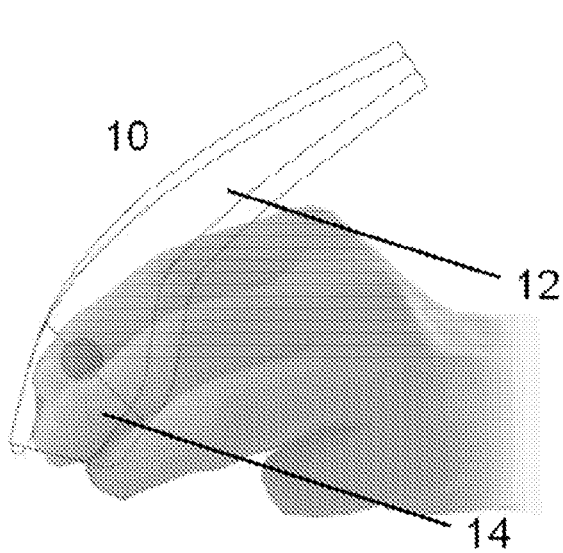
FIGS. 1A and 1B show schematic views of two handheld apparatuses 10 of the invention.

This invention relates to apparatuses, systems, kits, and methods for treating skin (e.g., eliminating tissue volume, tightening skin, lifting skin, and/or reducing skin laxity) by ablating tissue without substantial thermal energy being imparted to the surrounding (e.g., non-ablated) tissue. In particular, the invention relates to apparatuses, systems, kits, and methods that include skin-penetrating components with ablation members (e.g., needles, drill bits, abrading elements, punches, blades, fluid jets, and/or probes) capable of mechanical fractional ablation of the epidermal, dermal, and proximal tissue layers (e.g., fat, muscle, and SMAS (superficial muscular aponeurotic system)).

In particular embodiments, the present invention provides one or more of the following advantages. First, the non-thermal fractional ablation apparatuses, systems, kits, and methods herein allow for skin tightening, skin lifting, and/or reduction of skin laxity without inducing coagulation in the surrounding tissue. In contrast, thermal ablation techniques prevent and/or inhibit skin tightening by allowing coagulation of the tissue and formation of rigid tissue cores that cannot be compressed. Second, the handheld, compact, modular, and versatile apparatuses and systems herein facilitate ease of use and sterilization and permit treatment of varied skin regions and conditions with a single instrument. For example, a tip of an apparatus having an array with a particular number and configuration of ablation members (e.g., needles) can be used to treat a particular skin region and/or condition and, if desired, the tip may be exchanged during the treatment for a different tip having a different number and configuration of ablation members (e.g., needles) for treatment of a different skin region and/or condition. This adaptability may allow for treatment of multiple skin regions and/or conditions within a single treatment session. Third, the apparatuses, systems, and kits include micro-sized features, which can be beneficial for controlling the extent of skin treatment and for ease of handling the apparatus. Fourth, the apparatuses, systems, kits, and methods described herein may require less skill than that of a surgeon to operate and/or perform. For example, treatment of patients can occur in an outpatient setting, rather than in an inpatient, surgical setting. Fifth, the apparatuses, systems, kits, and methods herein constitute minimally invasive techniques that can provide more predictable results and/or minimize risk factors to a greater degree than that for more invasive techniques (e.g., plastic surgery) or non-invasive energy-based techniques (e.g., laser, radiofrequency, and ultrasound). Sixth, the apparatuses, systems, kits, and methods herein can allow for rapid closing of holes or slits after treating the skin (e.g., within a few seconds or minutes after treating skin, such as within about ten to about sixty seconds), thereby minimizing the extent of bleeding and/or clotting within the holes or slits and/or scar formation. Seventh, the apparatuses, systems, kits, and methods herein can be useful for maximizing the tightening effect while minimizing healing time by optimizing tightening (e.g., by controlling the extent of skin pleating, such as by increasing the extent of skin pleating for some applications or skin regions and by decreasing the extent of skin pleating for other applications or skin regions, as described herein). Eighth, the apparatuses, systems, kits, and methods for tissue removal described herein provide efficient clearance of partially ablated tissue and debris from ablated tissue portions, thus reducing the time for healing and improving the skin tightening treatment. Ninth, the apparatuses, systems, kits, and methods herein allow visualization of results in real time during the course of the treatment. For example, the operator can ask the patient for feedback in real time during the treatment and can adjust the treatment course according to the patient's preference. These and other advantages are facilitated by the handheld, compact, versatile, easy to use, and easy to sterilize apparatuses of the invention.

In some embodiments, apparatuses, systems, kits, and methods of the invention allow for the treatment of skin with varied thickness. Skin regions vary in thickness depending on the location on the body. For example, Kakasheva-Mazenkovska et al., (Contributions, Soc. Biol. Med. Sci., MASA, XXXII, 2, p. 119-128 (2011), incorporated by reference herein in its entirety) describes thin skin regions for 23-53 year old adults as including the anterior lower leg (average skin thickness of 1.7 mm) and the cheeks (average skin thickness of 2.1 mm) and thick skin regions as the anterior leg (average skin thickness of 4.9 mm, e.g., in the anterior upper leg) and the gluteus (average skin thickness of 5.2 mm).

In addition to variations in skin thickness, different regions of the body present issues of accessibility with known treatments. The versatility of the apparatuses of the present invention, which can be configured to treat skin of varying thicknesses at various locations on a subject, is therefore desirable.

Ablation Apparatus

The invention features an apparatus including a main body for handheld operation and a tip (e.g., configured as a detachable cartridge) that can be attached and detached (e.g., by a quick release mechanism) to the main body. The tip includes a skin-penetrating component with one or more ablation members (e.g., needles (e.g., hollow coring needles), drill bits, abrading elements, punches, and/or blades) configured for penetration into and retraction from skin that may also be configured to be in fluid communication with a pressure generating source (e.g., a vacuum pump, suction source, or fluid injection component (e.g., a high pressure fluid jet)). Such an apparatus provides many benefits including ease of use, ease of clean up and sterilization, disposability of components (e.g., the tip), rapid treatment of the skin, lower skill level required for use, and the potential for outpatient treatment with rapid healing times.

Main Body

Figure 1B:
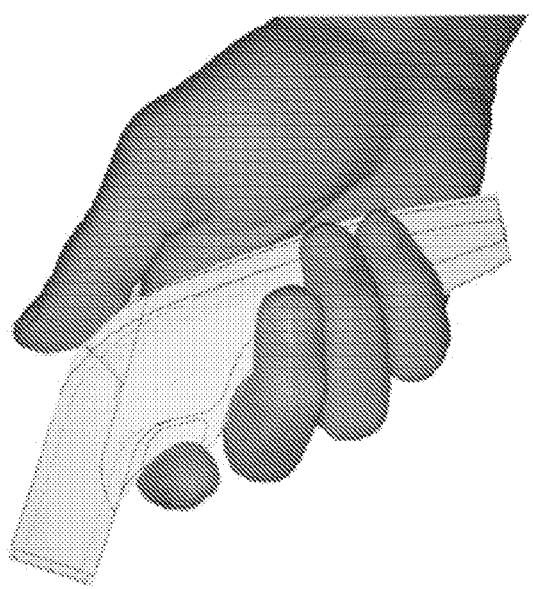
Figure 2:
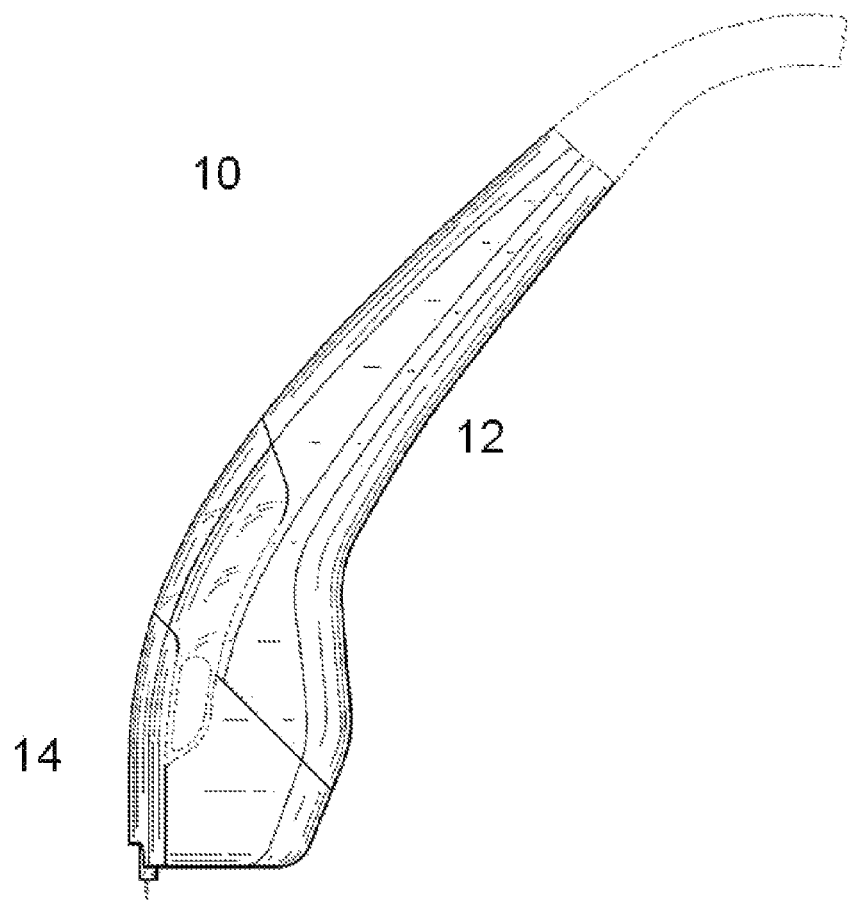
FIG. 2 is an illustration showing an apparatus 10 of the invention including main body 12 and tip 14.

FIGS. 1A, 1B, and 2 show schematics of apparatuses 10 of the invention each including main body 12 and tip 14. Main body 12 is configured for handheld operation, which facilitates ease of use. Main body 12 may feature a contoured design to permit comfortable, ergonomic operation. Such a design may also permit treatment of multiple areas of a subject without forcing the subject to move, in contrast to other, larger medical treatment systems. Main body 12 may be readily cleaned and sterilized (e.g., by steam sterilization).

Main body 12 of apparatus 10 may include additional components, such as a reservoir for collecting waste materials (e.g., tissue, blood, and/or interstitial fluids), a pressure generating source (e.g., a vacuum pump, suction source, or high pressure fluid jet), tubing and/or cables to couple various components, device control electronics and actuation mechanisms, activation mechanisms, a power supply (e.g., an alternator and/or battery component), and/or a user interface. The components of the apparatus may be provided to an operator (e.g., a doctor or surgeon) in sterile condition prior to use on a patient and many, if not all, of the components can be re-sterilized or replaced with sterile components prior to a subsequent use. For example, tubing components may be readily removable from the device for sterilization or replacement after use of the apparatus.

Figures 3A, 3B, 3C:
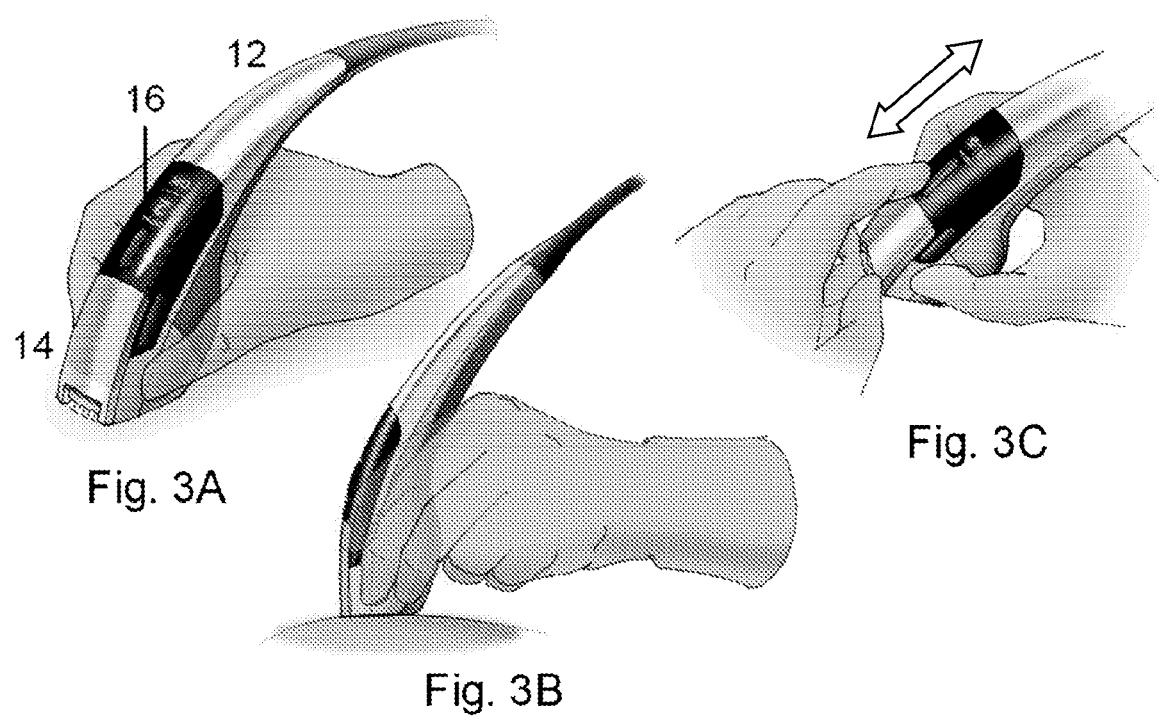
FIGS. 3A and 3B are illustrations showing perspective and side views, respectively, of an apparatus of the invention including user interface 16.
FIG. 3C is an illustration showing user interaction with user interface 16.

FIGS. 3A and 3B are illustrations of different views of an apparatus of the invention with user interface 16, while FIG. 3C demonstrates user interaction with user interface 16. User interface 16 of main body 12 may include indicators that the tip is properly coupled to main body 12, that the device is charged or otherwise powered (e.g., the amount of battery life remaining), that the ablation members (e.g., needles) are in an extended or retracted position, that a pressure generating source is coupled to the device, the fill level of a reservoir for collecting waste materials, and/or other useful information. User interface 16 may include information about the apparatus, such as the number of ablation members of the apparatus, the arrangement of the ablation members, the potential depth of tissue penetration by the ablation members, the mechanism or mode of operation, and/or other useful information. User interface 16 may include buttons, keys, switches, toggles, spin-wheels, LED displays, and/or touch screens that allow the user to observe and change various parameters or configurations during operation of the apparatus, to activate the high or low pressure generating source, and/or to initiate penetration into the skin by the ablation members. User interface 16 may be configured and disposed to allow a user to access buttons, keys, switches, toggles, spin-wheels, LED displays, and/or touch screens with the hand holding the apparatus or with the free hand (FIG. 3C). For example, a button for activating the high or low pressure generating source may be disposed on the one side of the main body such that it is can be depressed by one or more fingers of the user during operation. User interface 16 may also be configured to transmit and/or receive information from another unit, such as a computer or base unit (see FIGS. 8 and 9).

Main body 12 may feature additional buttons, keys, switches, toggles, spin-wheels, and/or touch screens to initiate penetration into the skin by the needles and/or translation of the device across the skin. These features may be components of user interface 16.

Figure 4:
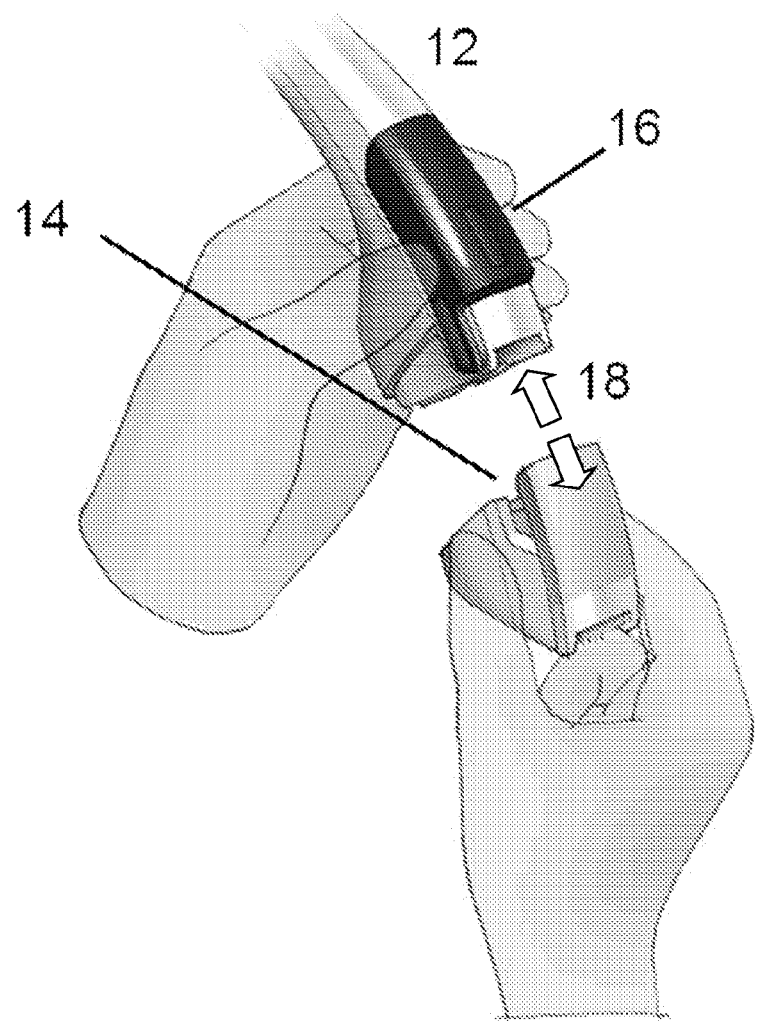
FIG. 4 shows an apparatus of the invention in which tip 14 is detachable from main body 12 by quick-release mechanism 18. The main body also includes user interface 16.
Figures 5A, 5B:
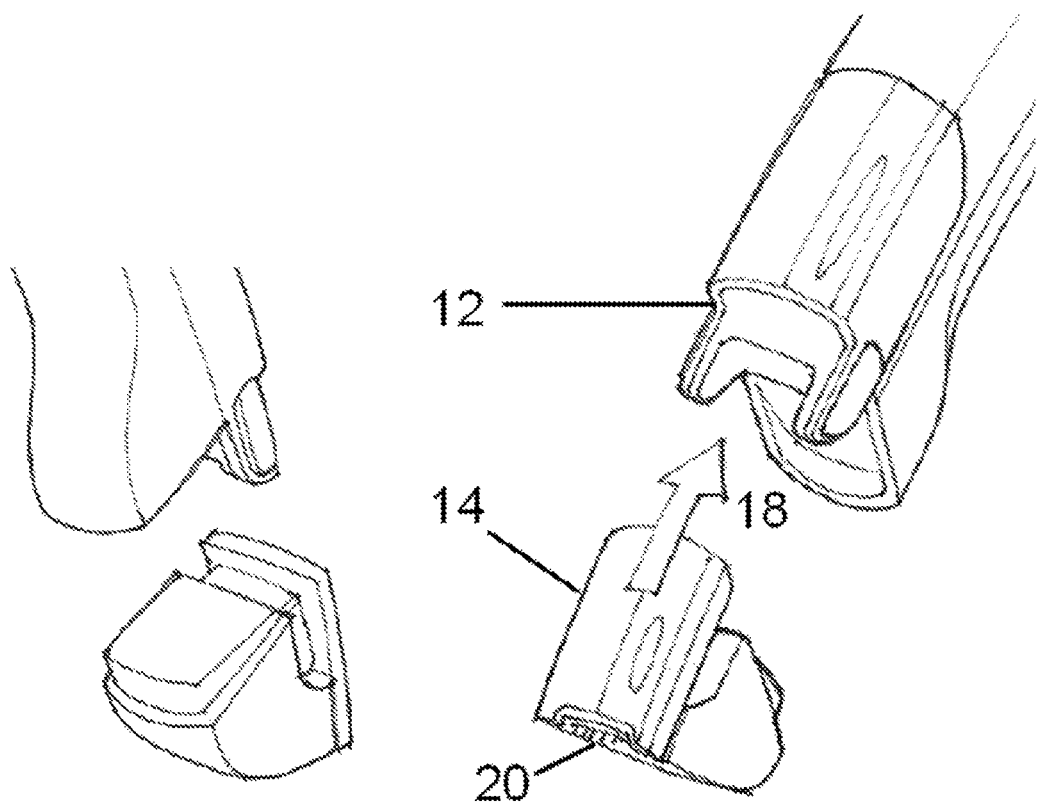
FIGS. 5A and 5B are illustrations showing two perspective views of an apparatus of the invention in which tip 14 is detachable from main body 12 by quick-release mechanism 18. The arrow in FIG. 5B is for illustration purposes only.

Main body 12 is configured to couple with a tip including a skin-penetrating component with ablation members (e.g., needles). Main body 12 may have a locking mechanism to secure the tip in place during operation. The locking mechanism may allow mechanical and/or electrical connection of additional components (e.g., one or more actuators that can be used to operate the components of the tip). In some embodiments, locking main body 12 and tip 14 may be used to establish fluidic connection between, e.g., the ablation members, a reservoir, and/or a pressure generating source. The main body-tip locking mechanism may be engaged and disengaged repeatably. The main body-tip locking mechanism may include one or more of adhesive, magnetic, electrical, and/or mechanical components (e.g., one or more gaskets, o-rings, septa, springs, clasps, and other engagement members). In some embodiments, the main body may include a groove or depression for placement of an o-ring (e.g., a viton o-ring, a nitrile rubber o-ring, and a thermoplastic polyurethane o-ring) that will allow for a seal to form between main body 12 and tip 14. The portion of tip 14 engineered to engage with main body 12 may include a corresponding groove or depression. In other embodiments, a locking mechanism may involve mated pieces made of molded plastic. FIGS. 5A and 5B show two views of main body 12 and mated tip 14. As an example, the body of tip 14 may be formed to fit as a sheath over a rim of main body 12, or vice versa, such that one component may form a seal by sliding partway into the other component. In the instance that tip 14 fits over the edge of main body 12, the inner surface of the housing of tip 14 may include a ridge formed as a stop to facilitate the seal. Main body 12 and tip 14 may also include interlocking ridges (e.g., made of plastic, rubber, or other material) to enhance or form a seal between the components. Main body 12 may also feature a mechanism to activate detachment of the tip from the main body. This mechanism may include one or more of a button, key, switch, toggle, spin-wheel, touch screen, and/or sliding lock. The detachment mechanism may be a quick-release mechanism. FIG. 4 shows an apparatus of the invention with quick-release mechanism 18 to separate tip 14 from main body 12. In some embodiments, one component (e.g., main body 12) includes a depressible portion that engages a seal when the other component (e.g., tip 14) is slid around the rim of the other. Depression of the portion may be disengaged by activation of a sliding lock, eliminating the seal between the components to allow their separation and, e.g., removal and replacement of tip 14.

Main body 12 may also include a power supply. For example, main body 12 may have a housing for batteries that power operation of the device or may be configured to receive an element including batteries (see FIG. 14). The housing may be configured to charge the batteries (e.g., when depleted) with a paired charging station, without requiring removal of the batteries, or the batteries may be removed from the device for replacement or charging. In another embodiment, main body 12 may include electronics and components (e.g., a power cord) that allow it to be powered from an external power supply, such as a direct or alternating current supply or a generator.

Tip

Tip 14 (e.g., configured as a detachable cartridge; see e.g., FIGS. 1-5) of apparatus 10 of the invention includes a skin-penetrating component (e.g., one or more needles, such as one or more hollow coring needles) and may be detachably attached to main body 12. The detachability of tip 14 provides an advantage in that the component that interacts with the skin can be easily removed from apparatus 10, thereby minimizing the cleaning and sterilization of apparatus 10. In some embodiments, tip 14 is designed for a single use. For example, tip 14 may be disposable. Alternatively, tip 14 may be cleaned and sterilized for reuse.

Figure 6:
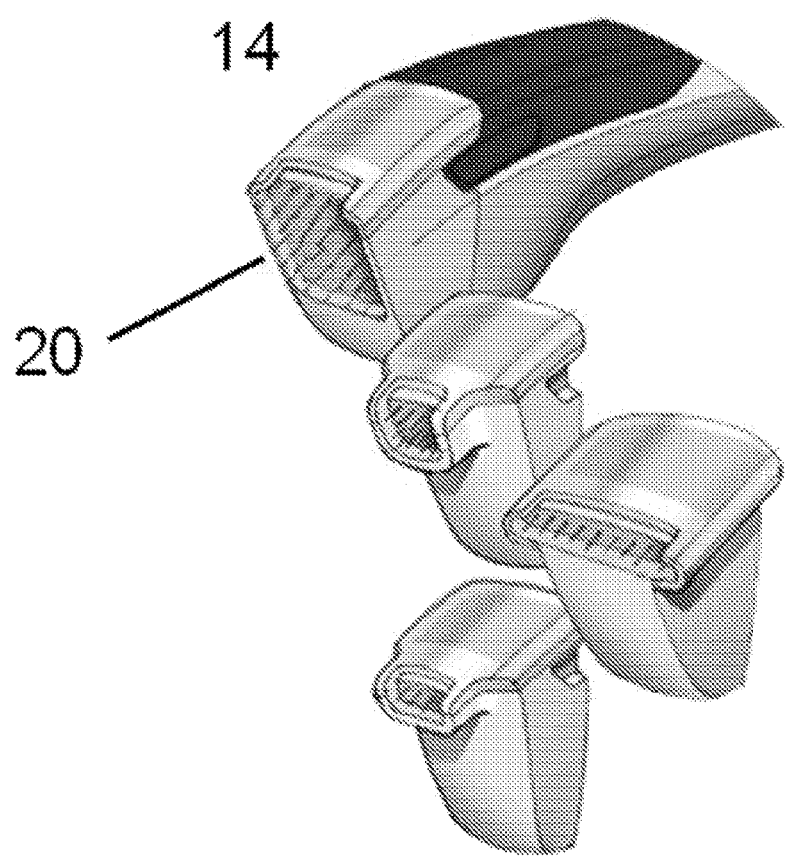
FIG. 6 shows tip 14 of an apparatus of the invention with skin penetrating components 20. Also shown are tips having a variable number and configuration of ablation members.

The detachability of tip 14 also facilitates the design and use of tips having varying numbers and configurations of ablation members (e.g., coring needles) and provides for quick interchangeability of apparatus architectures and applications. Different tip geometries may be useful for treatment of different regions of the skin. For example, a small tip may be useful for treatment of a limited surface area (e.g., the peri-oral area) while a large tip may be useful for treatment of a large surface area (e.g., the abdomen). A small tip may have a small number of ablation members (e.g., as few as 1) that may be arranged in a 1-dimensional array (e.g., a linear array), while a large tip may have many ablation members (e.g., up to or more than 100) that may be arranged in a 2-dimensional array (e.g., a rectangular array). FIG. 6 shows several different tips 14 with skin-penetrating components 20 of different geometries.

Tip 14 may further include elements for coupling the ablation members therewith. Such an element may have magnetic, adhesive, electrical, and/or mechanical components. For example, the coupling element may include one or more plastic connectors configured to couple to one or more ablation members. The ablation members may be joined to a coupling element by a molded plastic connection. Tip 14 may further feature an element coupling the ablation members fluidly to other components of the system such as a reservoir for collecting waste materials and/or a pressure generating source. This element may be a tube or series of tubes. In one embodiment, a seal formed by mechanically mating main body 12 and tip 14 may also be the seal establishing fluid connectivity with other components. In other embodiments, one or more tubes coupled to skin-penetrating component 20 of tip 14 must be mated (e.g., via one or more o-ring, gasket, KF, LF, QF, quick coupling, Swagelok, and other sealing mechanisms) to establish fluid connection between components of tip 14 and other components of the system.

Tip 14 may further couple with a detachable cover piece to cover the ablation members when the device is not in use in order to keep the components clean and/or sterile.

In some embodiments, tip 14 may include a reservoir for collecting waste materials (e.g., tissue, blood, and/or interstitial fluids) that is in fluid communication with the ablation members. The reservoir may further be in fluid communication with a pressure generating source (e.g., a vacuum pump). Tip 14 may have a filter, membrane, or other physical element that maintains separation between materials that enter the tip, such as collected waste materials, and other components of the system.

Reservoir

The apparatus may include or be otherwise coupled to a reservoir for collecting tissue, fluids (e.g., blood and/or interstitial fluids), and other waste. The collection of tissue and fluid allows skin tightening, minimizes the risk of infection, and maintains a clear treatment field for the operator of the apparatus.

The reservoir may be in fluid communication with the ablation members of the tip. The reservoir may be disposed within the tip or the main body of the apparatus, or it may be external to these components. Alternatively, a separate module of the apparatus may contain the reservoir. This module may be disposed between the tip and the main body, such that the module containing the reservoir is coupled to both components. The coupling elements may include mechanical and other components as described above. The module and/or its components may be designed for a single use; for example, the reservoir may be disposable. Alternatively, the reservoir may be easily removed from the system for cleaning (e.g., sterilization) and reuse.

The reservoir may be detachably attached to the tip and/or main body of the apparatus. The reservoir may be readily removable from the system (e.g., for ease of sterilization or disposability). The reservoir may be made of materials that are chemically and/or thermally resistant, and may feature chemically and/or thermally resistant coatings.

Sterilizing chemicals may be stored within the reservoir during, prior to, or after use of the apparatus. Sterilizing chemicals may include ethylene oxide, chlorine bleach, formaldehyde, hydrogen peroxide, peracetic acid, or other chemicals.

The reservoir may further be in fluid communication with a pressure generating source. For example, the reservoir may be in fluid communication with a vacuum pump. Transfer of ablated tissue and other materials may be achieved by applying a differential pressure across the circuit including the needles and reservoir. A filter, membrane, or other physical element may prevent suction of materials out of the reservoir toward the vacuum pump. Such a filter, membrane, or physical element may be disposed within the reservoir. A filter, membrane, or physical element may also be detachable from the reservoir, pressure generating source, and/or their coupling elements for sterilization and/or disposal.

Pressure Generating Source

The apparatus may further include or be otherwise coupled to a pressure generating source. In some embodiments, a separate tissue removal apparatus may include the pressure generating source. The tissue removal apparatus could additionally include a reservoir for collecting waste materials and a component to prevent material from the reservoir from contaminating the pressure generating source. In other embodiments, the pressure generating source may be configured to be in fluid communication with the ablation members of the tip and/or with a reservoir for collecting waste materials. Materials may be separated from the pressure generating source with one or more filters, membranes, and/or other physical elements known in the art.

The pressure generating source may be a low pressure generating source. For example, the pressure generating source may be capable of providing vacuum and/or suction. Vacuum sources may include one or more rotary pumps, momentum transfer pumps, diffusion pumps, scroll pumps, and/or diaphragm pumps. In some embodiments, a low pressure generating source may include a house or central vacuum system. In other embodiments, a suction source may include a wall or portable suction device. In some embodiments, a vacuum source provides an absolute pressure less than about 6.3 kPa (e.g., from about 0.1 kPa to about 6 kPa, such as from 0.1 kPa to 6 kPa, 0.1 kPa to 5 kPa, 0.1 kPa to 4 kPa, 0.1 kPa to 3 kPa, 0.1 kPa to 2 kPa, 0.1 kPa to 1 kPa, 0.5 kPa to 6 kPa, 0.5 kPa to 5 kPa, 0.5 kPa to 4 kPa, 0.5 kPa to 3 kPa, 0.5 kPa to 2 kPa, 0.5 kPa to 1 kPa, 1 kPa to 6 kPa, 1 kPa to 5 kPa, 1 kPa to 4 kPa, 1 kPa to 3 kPa, 1 kPa to 2 kPa, 1.5 kPa to 6 kPa, 1.5 kPa to 5 kPa, 1.5 kPa to 4 kPa, 1.5 kPa to 3 kPa, and 1.5 kPa to 2 kPa).

A low pressure generating source may be configured to remove tissue portions and other waste materials formed by penetration into tissue by ablation members. For example, suction and/or vacuum may be applied to remove waste materials from the ablation members (e.g., from the cores of coring needles) to prevent clogging during operation, to facilitate the separation of ablated tissue portions from surrounding tissue in a treatment area, and/or to remove waste materials from the treatment area. Suction and/or vacuum may be applied via the ablation members (e.g., needles) of the apparatus. The ablation members and low pressure generating source may be configured to remove tissue portions and other waste materials by providing suction and/or vacuum after penetration into the skin by but before removal of the needles. For example, a pressure generating source, such as a vacuum pump, may be coupled to needles that include holes as well as a reservoir for waste collection. Following penetration into the tissue by the ablation members, vacuum may be applied to draw waste materials from a treated skin area through holes in the ablation members and though tubing coupling the ablation members to the reservoir. A filter may prevent waste materials from leaving the reservoir and possibly aspirating within the pressure generating source (e.g., vacuum pump). In other embodiments, the pressure generating source (e.g., vacuum pump) may be activated after the ablation members (e.g., hollow coring needles) have been removed from the skin to clear any waste materials from the hollows of the ablation members and prevent clogging to allow for effective continued treatment. Alternatively, the pressure generating source (e.g., vacuum pump) may be integrated with a separate tissue removal apparatus. Such an apparatus may be configured with an array of small access ports along the bottom of a chamber which may be applied to a skin region. The access ports that contact a treated skin area may be configured to form a seal with the tissue such that, upon separation of the tissue removal apparatus from the skin region, ablated tissue portions and other waste materials may also be removed.

In an alternative configuration, the pressure generating source (e.g., vacuum pump) may be configured to directly ablate and/or facilitate ablation of the skin. For example, the ablation members (e.g., hollow needles) may be configured to apply a high level of vacuum (e.g., a vacuum with an absolute pressure less than about 6.3 kPa) to the skin, thereby directing tissue removal via either a suctioning mechanism or through conveyance of damage to the tissue that is targeted for removal or destruction. The size of an ablated tissue portion may be controlled by the level of vacuum, the duration of exposure, and the dimensional size (e.g., area or volume) over which the vacuum is applied. In one embodiment, vacuum may be used to ablate tissue by causing local boiling off or vaporization of tissue at ambient temperatures. In another embodiment, vacuum may ablate tissue by causing desiccation or freeze-drying of tissue.

The pressure generating source may alternatively facilitate exposure of a treatment area to fluid or gas and/or injection of fluid or gas into a treatment area. For example, the pressure generating source may be a fluid injection component (e.g., a high pressure fluid jet or an array of high pressure fluid jets). In some embodiments, a fluid jet or an array of fluid jets may be configured to ablate tissue non-thermally. For example, a jet with fluid pressure greater than about 200 psi may be positioned external to the skin surface, such that interaction between the fluid jet and the skin produces a hole in the skin. The size of the hole may be determined by the fluid jet size and length of exposure. For example, to provide an ablated skin portion with a shallower depth, the fluid jet may be applied for a shorter time. Alternatively, to provide an ablated skin portion with a greater depth or diameter, the fluid jet may be applied to the skin region for a longer time. A high pressure fluid jet for tissue ablation is a non-thermal ablative mechanism and does not generate a thermal injury to the surrounding tissue. In other embodiments, fluid jets may be used to clear clogs in ablation members. Alternatively, fluid jets may be configured to facilitate the removal of waste materials from a treatment area (e.g., by rinsing and/or otherwise dislodging waste materials). In other embodiments, one or more fluid jets may be used to expose the treatment area to one or more chemicals (e.g., medicaments, botulinum toxin, and fillers, such as hyaluronic acid- and collagen-based fillers). For example, fluid jets may be used to flush a treatment area with a collagen-based filler following ablation of the skin by the ablation members (e.g., needles) of the apparatus.

Non-limiting possible pressures for a fluid injection component (e.g., a fluid jet) include from about 200 psi to about 100000 psi (e.g., from 200 psi to 1000 psi, 200 psi to 5000 psi, 200 psi to 10000 psi, 200 psi to 50000 psi, 200 psi to 100000 psi, 500 psi to 1000 psi, 500 psi to 5000 psi, 500 psi to 10000 psi, 500 psi to 50000 psi, 500 psi to 100000 psi, 750 psi to 1000 psi, 750 psi to 5000 psi, 750 psi to 10000 psi, 750 psi to 50000 psi, 750 psi to 100000 psi, 1000 psi to 5000 psi, 1000 psi to 10000 psi, 1000 psi to 50000 psi, 1000 psi to 100000 psi, 1500 psi to 5000 psi, 1500 psi to 10000 psi, 1500 psi to 50000 psi, 1500 psi to 100000 psi, 2000 psi to 5000 psi, 2000 psi to 10000 psi, 2000 psi to 50000 psi, 2000 psi to 100000 psi, 2500 psi to 5000 psi, 2500 psi to 10000 psi, 2500 psi to 50000 psi, 2500 psi to 100000 psi, 4000 psi to 5000 psi, 4000 psi to 10000 psi, 4000 psi to 50000 psi, 4000 psi to 100000 psi, 5000 psi to 10000 psi, 5000 psi to 50000 psi, 5000 psi to 100000 psi, 7500 psi to 10000 psi, 7500 psi to 50000 psi, 7500 psi to 100000 psi, 10000 psi to 50000 psi, 10000 psi to 100000 psi, 50000 psi to 100000 psi, and 75000 psi to 100000 psi) and from about 15 psi to about 200 psi (e.g., 15 psi to 20 psi, 15 psi to 50 psi, 15 psi to 75 psi, 15 psi to 100 psi, 15 psi to 125 psi, 15 psi to 150 psi, 15 psi to 175 psi, 15 psi to 200 psi, 20 psi to 50 psi, 20 psi to 75 psi, 20 psi to 100 psi, 20 psi to 125 psi, 20 psi to 150 psi, 20 psi to 175 psi, 20 psi to 200 psi, 50 psi to 75 psi, 50 psi to 100 psi, 50 psi to 125 psi, 50 psi to 150 psi, 50 psi to 175 psi, 50 psi to 200 psi, 75 psi to 100 psi, 75 psi to 125 psi, 75 psi to 150 psi, 75 psi to 175 psi, 75 psi to 200 psi, 100 psi to 125 psi, 100 psi to 150 psi, 100 psi to 175 psi, 100 psi to 200 psi, 125 psi to 150 psi, 125 psi to 175 psi, 125 psi to 200 psi, 150 psi to 175 psi, 150 psi to 200 psi, and 175 psi to 200 psi).

In one embodiment, an apparatus containing one or more fluid jets may be configured for insertion into the fatty layer or under the dermis or epidermis. The array of fluid jets may be configured to emit fluid at very high pressure to ablate the tissue above. A low pressure out-flow tube may be positioned on the surface of the skin for removal of fluid and debris. In another embodiment, a fluid jet or an array of fluid jets may be configured for discontinuous fluid flow to allow removal of fluid and debris before reactivating the jet. In another embodiment, a fluid jet or an array of fluid jets may be configured to move (e.g., in a circular fashion) in relation to the skin, e.g., to produce an array of cylindrical ablations.

Fluid jets of the invention may be continuous or discontinuous fluid streams, and may feature turbulent and/or laminar flow. One or more nozzles may be configured to form a fluid jet. For example, a convergent nozzle may be used which reduces the diameter of the outlet, thus increasing the velocity of the fluid jet. In some embodiments, the ablation members of the tip (e.g., hollow needles) may be conduits for fluid streams.

Fluid jets may include one or more fluids. Non-limiting examples of fluids for use in a fluid jet or fluid jet array include aqueous and non aqueous solutions, such as isotonic and non isotonic buffers, and saline solutions. Fluid jets may include additional ingredients that have a desirable medical or aesthetic activity or utility (e.g., therapeutic agents, such as heparin, fibrin, antibiotics, lidocaine, and other analgesics, and/or botulinum toxin, and fillers, such as hyaluronic acid- and collagen-based fillers).

Alternatively, a fluid jet may be a gas jet such as an air jet. In some embodiments, a fluid jet or an array of fluid jets may be configured to remove tissue, fluids, and/or other debris generated during ablation of the skin. For example, a pressurized air stream may be applied to the skin following ablation via the ablation members (e.g., needles).

A pressure generating source may include a venturi-effect element at an end of an ablation member (e.g., a hollow needle). The venturi-effect element may convert a high pressure air stream into a vacuum. This conversion would push ablated tissue and other waste materials into a collection reservoir after exiting the end of the ablation member.

Actuation, Translation, and Position Detection Mechanisms

The apparatus may further include actuation mechanisms to drive ablation members (e.g., needles, such as hollow coring needles) into or across skin. A "z" actuator may drive penetration into the skin by the ablation members and/or retraction of the ablation members after insertion. The apparatus may include a feature or setting that has the ability to control or change the depth of penetration of the ablation members into the skin. For example, a scroll wheel on a user interface of a main body may adjust the allowed depth of penetration by the ablation members by physically retracting the ablation members and/or providing an electrical signal to a z-actuator. Alternatively, digital controls on the user interface of the base unit may control the depth and/or timing of penetration into and retraction out of the skin by the ablation members (e.g., needles). For example, an operator may program a computer component of the base unit to require a certain displacement of the ablation members (e.g., needles) into the skin based upon the area being treated. The z-actuator may be programmed or otherwise set to displace the ablation members (e.g., needles) up to about 15 mm into thick skin (e.g., on a patient's back) or about 2 mm into thin skin (e.g., on a patient's cheeks), for instance. The z-actuator may also be capable of operating at a high speed to minimize treatment time and deflection of the skin during the penetration of the ablation members and penetration force. The z-actuator may further be capable of operating with relatively high force. Preferably, a force of about 0.5 N to about 20 N (e.g., 0.5 N to 0.75 N, 0.5 N to 1 N, 0.5 N to 1.25 N, 0.5 N to 1.5 N, 0.5 N to 2 N, 0.5 N to 5 N, 0.5 N to 10 N, 0.5 N to 12 N, 0.5 N to 15 N, 0.5 N to 20 N, 0.75 N to 1 N, 0.75 N to 1.25 N, 0.75 N to 1.5 N, 0.75 N to 2 N, 0.75 N to 5 N, 0.75 N to 10 N, 0.75 N to 12 N, 0.75 N to 15 N, 0.75 N to 20 N, 1 N to 1.25 N, 1 N to 1.5 N, 1 N to 2 N, 1 N to 5 N, 1 N to 10 N, 1 N to 12 N, 1 N to 15 N, 1 N to 20 N, 1.25 N to 1.5 N, 1.25 N to 2 N, 1.25 N to 5 N, 1.25 N to 10 N, 1.25 N to 12 N, 1.25 N to 15 N, 1.25 N to 20 N, 1.5 N to 2 N, 1.5 N to 5 N, 1.5 N to 10 N, 1.5 N to 12 N, 1.5 N to 15 N, 1.5 N to 20 N, 2 N to 5 N, 2 N to 10 N, 2 N to 12 N, 2 N to 15 N, 2 N to 20 N, 5N to 10 N, 5N to 12 N, 5N to 15 N, 5N to 20 N, 10 N to 12 N, 10 N to 15 N, 10 N to 20 N, 12 N to 15 N, 12 N to 20 N, and 15 N to 20 N) per ablation member (e.g., needle) can be applied to ensure insertion of the ablation member into the skin. Actuator types having these characteristics include pneumatic actuators, electromagnetic actuators, motors with cams, motors with lead screws (e.g., stepper motors), and piezoelectric actuators. The insertion force may be inversely correlated with needle gauge. For example, a 24 gauge needle may be operated with an insertion force of 12 N, while a 20 gauge needle may be operated with a higher insertion force.

The apparatus may include an "x" and/or "y" actuator for driving the ablation members (e.g., needles) across the skin. The x/y-actuator may be used to establish the treatment coverage by defining the distance between two applications of an array of ablation members. The x/y-actuator may be characterized by a relatively large displacement range (e.g., up to about 30 mm). The x/y-actuator may also operate at a relatively high speed to minimize treatment time. Actuator types having these characteristics include pneumatic actuators, electromagnetic actuators, motors with cams, piezoelectric actuators, and motors with lead screws (e.g., stepper motors).

Figure 7:
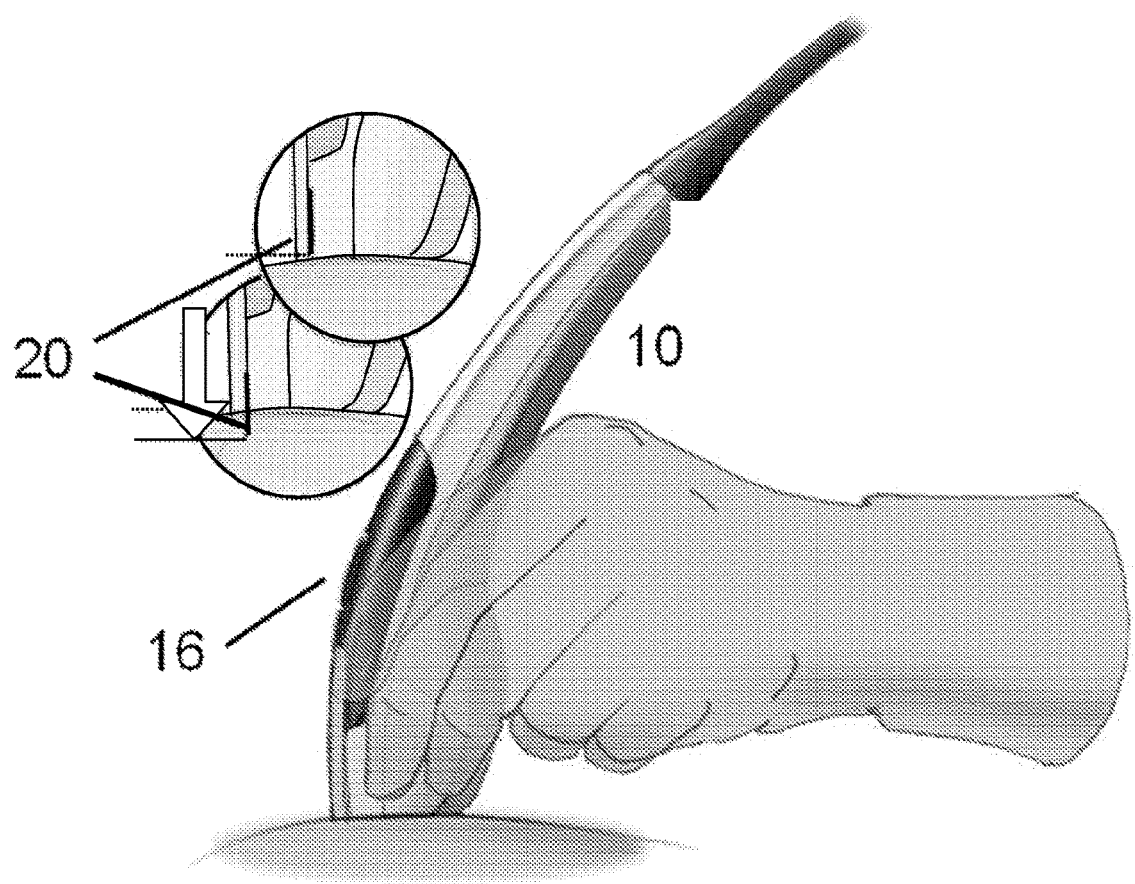
FIG. 7 is an illustration showing apparatus 10 of the invention featuring user interface 16 to activate penetration into the tissue with skin penetrating component 20. The inset shows the ablation members of skin penetrating component 20 in extended and retracted configurations.

Actuation components may be disposed in the main body of the apparatus or external to the main body. The z-, x-, and y-actuators may be activated independently or together by one or more buttons, keys, toggles, switches, screws, dials, cursors, spin-wheels, or other components. In an embodiment, each of the z-, x-, and y-actuators can be separately controlled (e.g., using separate activation components, such as a button, or by using separate controls in a user interface). FIG. 7 is an illustration of an apparatus of the invention with the ablation members (e.g., needles) of the skin-penetrating component 20 in both retracted and extended positions. Z-actuation may be activated by a trigger button element disposed on the main body of the apparatus that is accessible to the index finger of the operator. Alternatively, digital controls on user interface 32 of base unit 30 or user interface 16 of main body 12 may control the depth and/or timing of penetration into and retraction out of the skin by the ablation members (e.g., needles) and/or translation of the apparatus across the skin surface.

The apparatus may further include a translation mechanism to drive ablation members across the skin (e.g., x- and y-translation). A translation mechanism may include, e.g., driving wheels or rods. A translation mechanism may permit automatic or manual translation of the apparatus across the skin. Translating components (e.g., wheels) may be disposed in or on the main body, be detachably attachable to the tip, or be disposed external to the main body. The translating mechanism may be activated by an activator, such as a button, key, toggle, switch, screw, cursor, dial, spin-wheel, or other component, and/or may be digitally controlled at user interface 32 of base unit 30 or user interface 16 of main body 12.

The apparatus may also include a position detection mechanism, such as an optical tracking mechanism. A position detection mechanism (e.g., a camera, infrared sensor, photodiode, and LED and detector) may assist in tracking movement of the apparatus in relation to a patient or a treatment area. The optical tracking mechanism may also facilitate placement of the skin-penetrating component on the skin surface in the instance of manual translation of the device across the skin. Control electronics for a position detection mechanism may be disposed in the main body of the apparatus or external to the main body (e.g., in a base unit or separate computer). For example, the position detection mechanism may monitor the distance between the previous needle insertion and the current device position and send a signal to the control electronics to actuate the skin penetration mechanism when the device has reached the desired position (e.g., a position a defined distance from the position where the needles were last inserted). Desired distances and/or positions may be controlled at user interface 32 or user interface 16.

Materials

The apparatuses, systems, kits, and methods of the invention can include any useful materials.

For example, the main body, tip, and other components may include and/or be formed from any useful polymer or plastic. Such materials may include alginate, benzyl hyaluronate, carboxymethylcellulose, cellulose acetate, chitosan, collagen, dextran, epoxy, gelatin, hyaluronic acid, hydrocolloids, nylon (e.g., nylon 6 or PA6), pectin, poly (3-hydroxyl butyrate-co-poly (3-hydroxyl valerate), polyalkanes, polyalkene, polyalkynes, polyacrylate (PA), polyacrylonitrile (PAN), polybenzimidazole (PBI), polycarbonate (PC), polycaprolactone (PCL), polyester (PE), polyethylene glycol (PEG), polyethylene oxide (PEO), PEO/polycarbonate/polyurethane (PEO/PC/PU), poly(ethylene-co-vinyl acetate) (PEVA), PEVA/polylactic acid (PEVA/PLA), polyethylene, polypropylene, poly (ethylene terephthalate) (PET), PET/poly (ethylene naphthalene) (PET/PEN) polyglactin, polyglycolic acid (PGA), polyglycolic acid/polylactic acid (PGA/PLA), polyimide (PI), polylactic acid (PLA), poly-L-lactide (PLLA), PLLA/PC/polyvinylcarbazole (PLLA/PC/PVCB), poly (β-malic acid)-copolymers (PMLA), polymethacrylate (PMA), poly (methyl methacrylate) (PMMA), polystyrene (PS), polyurethane (PU), poly (vinyl alcohol) (PVA), polyvinylcarbazole (PVCB), polyvinyl chloride (PVC), polyvinylidenedifluoride (PVDF), polyvinylpyrrolidone (PVP), silicone, rayon, polytetrafluoroethylene (PTFE), polyether ether ketone (PEEK), or combinations thereof. Polymers and/or plastics of the invention may be composite materials in which additives to the polymers and/or plastics, such as ceramics or particles, alter the mechanical properties.

Elements of the invention (e.g., all or a portion of the apparatus, such as all or a portion of the main body, tip, or other components) may also include and/or be formed from any useful metal or metal alloy. For example, in some embodiments, the ablation members may be metallic needles. Metals and alloys featured in the invention include stainless steel; titanium; a nickel-titanium (NiTi) alloy; a nickel-titanium-niobium (NiTiNb) alloy; a nickel-iron-gallium (NiFeGa) alloy; a nickel-manganese-gallium (NiMnGa) alloy; a copper-aluminum-nickel (CuAlNi) allow; a copper-zinc (CuZn) alloy; a copper-tin (CuSn) alloy; a copper-zinc-aluminum (CuZnAl) alloy; a copper-zinc-silicon (CuZnSi) alloy; a copper-zinc-tin (CuZnSn) alloy; a copper-manganese alloy; a gold-cadmium (AuCd) alloy; a silver-cadmium (AgCd) alloy; an iron-platinum (FePt) alloy; an iron-manganese-silicon (FeMnSi) alloy; a cobalt-nickel-aluminum (CoNiAl) alloy; a cobalt-nickel-gallium (CoNiGa) alloy; or a titanium-palladium (TiPd) alloy. Elements of the invention may also include and/or be formed from glass. For example, an apparatus of the invention may include glass needles.

Apparatuses, systems, kits, and methods of the invention may use one or more adhesives. An adhesive may be located on a surface, between elements, or otherwise adhered to an element of the invention. Useful adhesives include a biocompatible matrix (e.g., those including at least one of collagen (e.g., a collagen sponge), low melting agarose (LMA), polylactic acid (PLA), and/or hyaluronic acid (e.g., hyaluranon); a photosensitizer (e.g., Rose Bengal, riboflavin-5-phosphate (R-5-P), methylene blue (MB), N-hydroxypyridine-2-(1H)-thione (N-HTP), a porphyrin, or a chlorin, as well as precursors thereof); a photochemical agent (e.g., 1,8 naphthalimide); a synthetic glue (e.g., a cyanoacrylate adhesive, a polyethylene glycol adhesive, or a gelatin-resorcinol-formaldehyde adhesive); a biologic sealant (e.g., a mixture of riboflavin-5-phosphate and fibrinogen, a fibrin-based sealant, an albumin-based sealant, or a starch-based sealant); or a hook or loop and eye system (e.g., as used for Velcro®). In particular embodiments, adhesives are biodegradable.

Adhesives may be pressure-sensitive adhesives (PSAs). The properties of pressure sensitive adhesives are governed by three parameters: tack (initial adhesion), peel strength (adhesion), and shear strength (cohesion). Pressure-sensitive adhesives can be synthesized in several ways, including solvent-borne, water-borne, and hot-melt methods. Tack is the initial adhesion under slight pressure and short dwell time and depends on the adhesive's ability to wet the contact surface. Peel strength is the force required to remove the PSA from the contact surface. The peel adhesion depends on many factors, including the tack, bonding history (e.g. force, dwell time), and adhesive composition. Shear strength is a measure of the adhesive's resistance to continuous stress. The shear strength is influenced by several parameters, including internal adhesion, cross-linking, and viscoelastic properties of the adhesive. Permanent adhesives are generally resistant to debonding and possess very high peel and shear strength. Pressure-sensitive adhesives may include natural rubber, synthetic rubber (e.g., styrene-butadiene and styrene-ethylene copolymers), polyvinyl ether, polyurethane, acrylic, silicones, and ethylene-vinyl acetate copolymers. A copolymer's adhesive properties can be altered by varying the composition (via monomer components) changing the glass transition temperature (Tg) or degree of cross-linking. In general, a copolymer with a lower Tg is less rigid and a copolymer with a higher Tg is more rigid. The tack of PSAs can be altered by the addition of components to alter the viscosity or mechanical properties. Pressure sensitive adhesives are further described in Czech et al., "Pressure-Sensitive Adhesives for Medical Applications," in Wide Spectra of Quality Control, Dr. Isin Akyar (Ed., published by InTech), Chapter 17 (2011), which is hereby incorporated by reference in its entirety.

The apparatuses, systems, kits, and methods of the invention may include one or more useful therapeutic agents. For example, the ablation members (e.g., needles) of the apparatus of the invention may be configured to administer one or more therapeutic agents to the skin. Examples of such agents include one or more growth factors (e.g., vascular endothelial growth factor (VEGF), platelet-derived growth factor (PDGF), transforming growth factor beta (TGF-β), fibroblast growth factor (FGF), epidermal growth factor (EGF), and keratinocyte growth factor); one or more stem cells (e.g., adipose tissue-derived stem cells and/or bone marrow-derived mesenchymal stem cells); one or more skin whitening agents (e.g., hydroquinone); one or more vitamin A derivatives (e.g., tretinoin), one or more analgesics (e.g., paracetamol/acetaminophen, aspirin, a non-steroidal antiinflammatory drug, as described herein, a cyclooxygenase-2-specific inhibitor, as described herein, dextropropoxyphene, co-codamol, an opioid (e.g., morphine, codeine, oxycodone, hydrocodone, dihydromorphine, pethidine, buprenorphine, tramadol, or methadone), fentanyl, procaine, lidocaine, tetracaine, dibucaine, benzocaine, p-butylaminobenzoic acid 2-(diethylamino) ethyl ester HCl, mepivacaine, piperocaine, dyclonine, or venlafaxine); one or more antibiotics (e.g., cephalosporin, bactitracin, polymyxin B sulfate, neomycin, bismuth tribromophenate, or polysporin); one or more antifungals (e.g., nystatin); one or more antiinflammatory agents (e.g., a non-steroidal antiinflammatory drug (NSAID, e.g., ibuprofen, ketoprofen, flurbiprofen, piroxicam, indomethacin, diclofenac, sulindac, naproxen, aspirin, ketorolac, or tacrolimus), a cyclooxygenase-2-specific inhibitor (COX-2 inhibitor, e.g., rofecoxib (Vioxx®), etoricoxib, and celecoxib (Celebrex®)), a glucocorticoid agent, a specific cytokine directed at T lymphocyte function), a steroid (e.g., a corticosteroid, such as a glucocorticoid (e.g., aldosterone, beclometasone, betamethasone, cortisone, deoxycorticosterone acetate, dexamethasone, fludrocortisone acetate, hydrocortisone, methylprednisolone, prednisone, prednisolone, or triamcinolone) or a mineralocorticoid agent (e.g., aldosterone, corticosterone, or deoxycorticosterone)), or an immune selective antiinflammatory derivative (e.g., phenylalanine-glutamine-glycine (FEG) and its D-isomeric form (feG))); one or more antimicrobials (e.g., chlorhexidine gluconate, iodine (e.g., tincture of iodine, povidone-iodine, or Lugol's iodine), or silver, such as silver nitrate (e.g., as a 0.5% solution), silver sulfadiazine (e.g., as a cream), or Ag⁺ in one or more useful carriers (e.g., an alginate, such as Acticoat® including nanocrystalline silver coating in high density polyethylene, available from Smith & Nephew, London, U.K., or Silvercel® including a mixture of alginate, carboxymethylcellulose, and silver coated nylon fibers, available from Systagenix, Gatwick, U.K.; a foam (e.g., Contreet® Foam including a soft hydrophilic polyurethane foam and silver, available from Coloplast A/S, Humlebæk, Denmark); a hydrocolloid (e.g., Aquacel® Ag including ionic silver and a hydrocolloid, available from Conva Tec Inc., Skillman, N.J.); or a hydrogel (e.g., Silvasorb® including ionic silver, available from Medline Industries Inc., Mansfield, Mass.)); one or more antiseptics (e.g., an alcohol, such as ethanol (e.g., 60-90%), 1-propanol (e.g., 60-70%), as well as mixtures of 2-propanol/isopropanol; boric acid; calcium hypochlorite; hydrogen peroxide; manuka honey and/or methylglyoxal; a phenol (carbolic acid) compound, e.g., sodium 3,5-dibromo-4-hydroxybenzene sulfonate, trichlorophenylmethyl iodosalicyl, or triclosan; a polyhexanide compound, e.g., polyhexamethylene biguanide (PHMB); a quaternary ammonium compound, such as benzalkonium chloride (BAC), benzethonium chloride (BZT), cetyl trimethylammonium bromide (CTMB), cetylpyridinium chloride (CPC), chlorhexidine (e.g., chlorhexidine gluconate), or octenidine (e.g., octenidine dihydrochloride); sodium bicarbonate; sodium chloride; sodium hypochlorite (e.g., optionally in combination with boric acid in Dakin's solution); or a triarylmethane dye (e.g., Brilliant Green)); one or more antiproliferative agents (e.g., sirolimus, tacrolimus, zotarolimus, biolimus, or paclitaxel); one or more emollients; one or more hemostatic agents (e.g., collagen, such as microfibrillar collagen, chitosan, calcium-loaded zeolite, cellulose, anhydrous aluminum sulfate, silver nitrate, potassium alum, titanium oxide, fibrinogen, epinephrine, calcium alginate, poly-N-acetyl glucosamine, thrombin, coagulation factor(s) (e.g., II, V, VII, VIII, IX, X, XI, XIII, or Von Willebrand factor, as well as activated forms thereof), a procoagulant (e.g., propyl gallate), an anti-fibrinolytic agent (e.g., epsilon aminocaproic acid or tranexamic acid), and the like); one or more procoagulative agents (e.g., any hemostatic agent described herein, desmopressin, coagulation factor(s) (e.g., II, V, VII, VIII, IX, X, XI, XIII, or Von Willebrand factor, as well as activated forms thereof), procoagulants (e.g., propyl gallate), antifibrinolytics (e.g., epsilon aminocaproic acid), and the like); one or more anticoagulative agents (e.g., heparin or derivatives thereof, such as low molecular weight heparin, fondaparinux, or idraparinux; an anti-platelet agent, such as aspirin, dipyridamole, ticlopidine, clopidogrel, or prasugrel; a factor Xa inhibitor, such as a direct factor Xa inhibitor, e.g., apixaban or rivaroxaban; a thrombin inhibitor, such as a direct thrombin inhibitor, e.g., argatroban, bivalirudin, dabigatran, hirudin, lepirudin, or ximelagatran; or a coumarin derivative or vitamin K antagonist, such as warfarin (coumadin), acenocoumarol, atromentin, phenindione, or phenprocoumon); one or more immune modulators, including corticosteroids and non-steroidal immune modulators (e.g., NSAIDS, such as any described herein); one or more proteins; and/or one or more vitamins (e.g., vitamin A, C, and/or E). One or more of botulinum toxin, fat (e.g. autologous), hyaluronic acid, a collagen-based filler, or other filler may also be administered to the skin.

A therapeutic agent may include anticoagulative and/or procoagulative agents. For instance, by controlling the extent of bleeding and/or clotting in treated skin regions, a skin tightening effect may be more effectively controlled. Thus, in some embodiments, the methods and devices herein include or can be used to administer one or more anticoagulative agents, one or more procoagulative agents, one or more hemostatic agents, one or more fillers, or combinations thereof. In particular embodiments, the therapeutic agent controls the extent of bleeding and/or clotting in the treated skin region, including the use one or more anticoagulative agents (e.g., to inhibit clot formation prior to skin healing or slit/hole closure) and/or one or more hemostatic or procoagulative agents.

Ablation System

Any of the apparatuses of the invention described herein may be components of a system for non-thermal tissue ablation. In addition to the main body and tip of the apparatus, a system for non-thermal tissue ablation may include additional elements, such as a reservoir for collecting waste materials (e.g., tissue, blood, and/or interstitial fluids), a pressure generating source (e.g., a vacuum pump), mechanisms for actuation (e.g., pneumatic and/or electromagnetic actuators), translation (e.g., driving wheels), and position detection (e.g., a camera), a base unit, and a skin positioning apparatus. Any or all of the components may be readily sterilized prior to and/or after treatment of a patient or, if desired, replaced with sterile components.

Base Unit

A system for non-thermal tissue ablation may have a base unit that may include, e.g., a user interface, a power supply, control electronics, mechanisms to drive operation of the apparatus, and other components. The base unit may feature a computer, which may be programmed to operate and/or control any or all aspects of an apparatus of the invention.

A user interface of a base unit may include buttons, keys, switches, toggles, spin-wheels, screens, touch screens, keyboards, cursors, dials, indicators, displays, and/or other components. The user interface may be configured to indicate proper coupling of the tip and/or reservoir module to the main body, charged and/or powered status of the apparatus, the mode and/or position of ablation members (e.g., needles), coupling of a pressure generating source (e.g., a vacuum pump) to the apparatus, the application of low or high pressure, the fill level of a waste-collecting reservoir, actuation of system components, and/or other useful indicia. The user interface may be configured to provide information about the number and kind of ablation members of the apparatus, the treatment area, the treatment coverage (e.g., percentage of skin surface area ablated) the arrangement of the ablation members, the potential depth of penetration by the ablation members (if relevant), the mechanism or mode of operation, use count of the tip and/or reservoir, and other useful information. The user interface may allow adjustment of parameters and/or operation mode, application of high or low pressure, and/or activation of penetration into the skin by the ablation members. The user interface may also be configured to transmit and/or receive information from another unit. For example, user actions at a user interface on the main body of the apparatus may be reflected by a user interface of the base unit, or vice versa.

The base unit may include buttons, keys, switches, toggles, spin-wheels, and/or other activation mechanisms to allow adjustment of parameters and/or operation mode, application of high or low pressure, penetration into the skin by the ablation members, and/or powering on or off of the base unit, pressure generating source, apparatus, and/or other system components. These components may be integrated into the user interface.

The base unit may further include electronics to control operation of the apparatus, pressure generating source, and/ or other components of the system. For example, the base unit may include one or more microcontrollers, programmable logic, discrete elements, and/or other components. The base unit may further have one or more power supplies. Power supplies may include batteries, alternators, generators, and/or other components. The base unit may be configured to allow conversion of main power to DC for system operation, for example. In some embodiments, the base unit has a battery charging station for use with a battery-powered apparatus.

The base unit may include a reservoir for collecting waste materials, a pressure generating source, mechanisms to drive ablation members into or across the skin, a position detection mechanism, and other components, as provided above.

Figure 8:
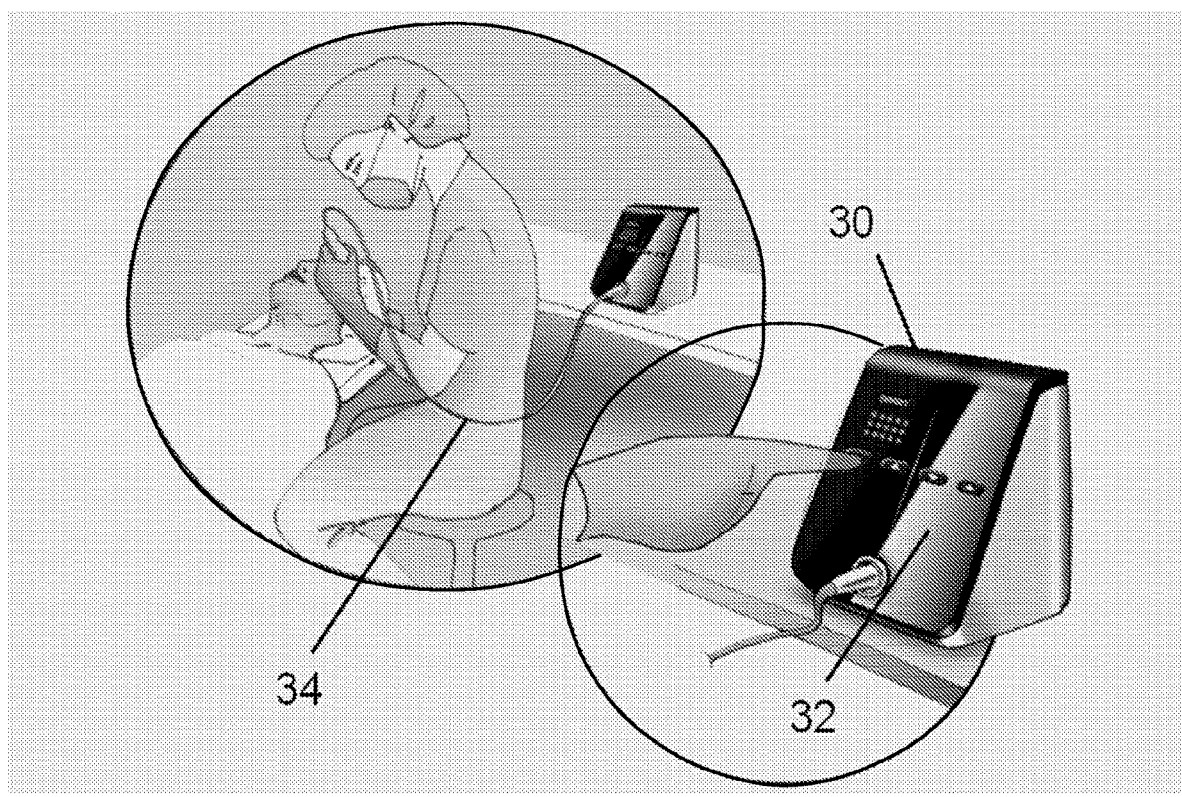
FIG. 8 is an illustration showing a system of the invention that includes base unit 30 with user interface 32 coupled to a handheld apparatus by cable 34. The cable carries one or more of power, information, and suction to and/or from the handheld apparatus.
Figure 9A:
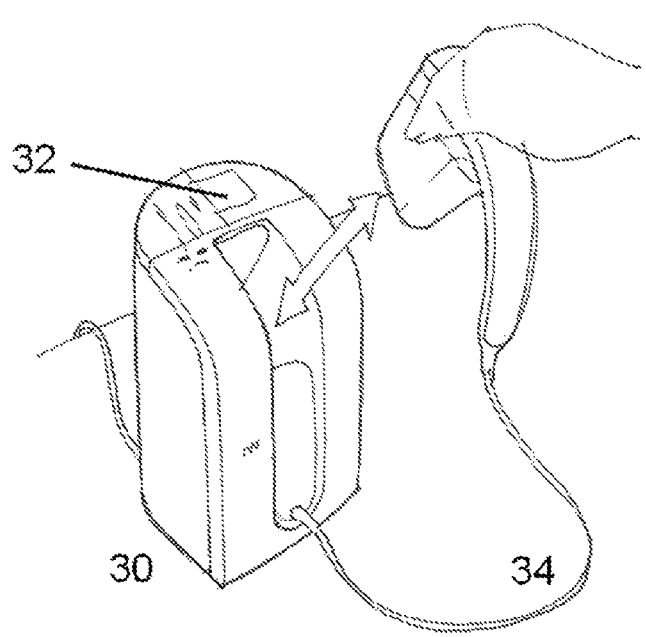
FIGS. 9A and 9B are illustrations of two base units 30 of the invention including user interfaces 32 and cables 34.
Figure 9B:
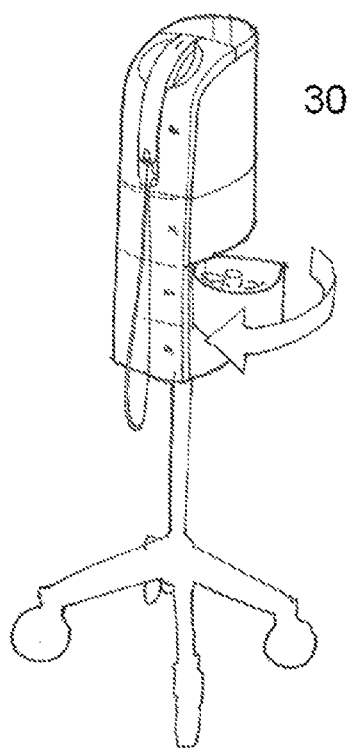

One or more cables may couple the base unit to the main body. The cable or cables may carry power and/or electrical signals to permit operation of the apparatus and its components. The cable or cables may be capable of carrying high pressure, vacuum, and/or suction. Multiple cables may be joined together. For example, tubing or wrapping material may be placed around multiple cables to effectively create a single cable linking the base unit and the apparatus. FIG. 8 shows a system of the invention that includes a main body coupled to base unit 30 by cable 34 capable of carrying one or more of power, information, and suction. The base unit shown also includes user interface 32. In addition to or in place of coupling via a cable, the base unit and the main body may be wirelessly coupled. The base unit may also have a power cord that can be plugged into a wall, floor, or ceiling power source and/or a tube for connection to an external pressure generating source (e.g., a house or medical suction system). FIGS. 9A and 9B illustrate examples of base unit configurations. For example, the base unit of FIG. 9A is a small docking station, while the base unit of FIG. 9B is a larger, portable station.

Skin Positioning Apparatus

A non-thermal tissue ablation system may further include a skin positioning apparatus. A skin positioning apparatus should be configured to allow for efficient and effective positioning of skin prior to, during, and after ablation and/or tissue removal. Positioning the skin provides control to the direction of skin-tightening subsequent to treatment and ensures that ablation occurs in the desired location and with the desired dimensions.

Figure 10:
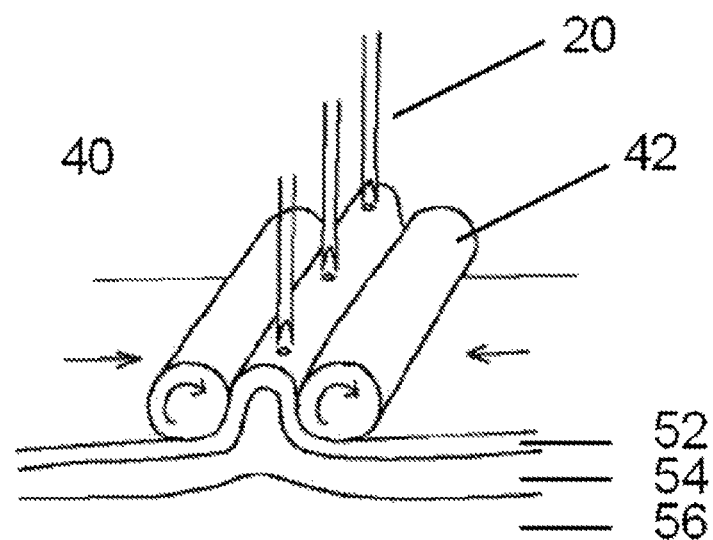
FIG. 10 shows a skin positioning apparatus 40 of the invention that includes skin tensioning rods 42. The skin positioning apparatus may position skin for treatment of tissue layers such as dermis 52, subcutaneous fat 54, and muscle 56, e.g., using an apparatus of the invention.

An apparatus capable of gripping and/or lifting the skin provides numerous advantages: it holds the skin in place during the introduction of the ablation members (e.g., needles), minimizes deflection of the skin when embedding more than one needle at a time ("needle-bed effect"); reduces the risk of the user moving the apparatus during treatment, which could result in unpredictable treatment coverage; allows lifting of the skin (reducing the risk of ablation members damaging underlying structures, such as blood vessels, nerves, muscle, and bone); and allows tensioning of the skin to permit generation of non-circular ablations. A skin gripping and/or lifting apparatus should have high gripping force to sustain the insertion force of the ablation members, permit gripping of wet skin that may be covered with blood and/or interstitial fluids, minimize damage to the skin, and permit fast gripping and release to minimize treatment duration. Skin positioning mechanisms include, e.g., penetrating needle grippers, rollers pinching the skin, adhesives, freezing grippers, and vacuum grippers (including Coanda and Bernouilli grippers). FIG. 10 shows skin positioning apparatus 40 of the invention that includes tensioning rods 42. Tensioning rods 42 are used to apply force to the skin surface by moving the rods toward each other, thus pinching the skin to elevate the dermis 52 and subcutaneous fat 54 away from the underlying structures (e.g., sub-dermal muscle layer 56, blood vessels, and nerve fibers). Additional examples and details of skin positioning apparatuses are provided in PCT/US14/50426, "Methods and Apparatuses for Skin Treatment Using Non-Thermal Tissue Ablation," which is herein incorporated by reference in its entirety.

Tissue Removal

A system or kit of the invention may further include components to aid in the removal of tissue and/or fluids, such as blood and interstitial fluids. Tissue removal components may include a low or high pressure generating source as described above. In addition to or instead of these components, tissue removal components may include adhesive materials, temperature controllers, and/or other elements. For example, a heating element coupled to the needles of the skin-penetrating component may be actuated which causes the needles to heat up to facilitate separation of ablated tissue portions from the skin. A vacuum source may then be applied to remove the heated ablated tissue portions and fluids. Additional examples and details of tissue removal components and apparatuses are provided in PCT/US14/50426.

Additional Components

A system of the invention may include additional components, such as a camera and/or viewing station. A camera may be used to image a treatment area before, during, or after treatment. In some embodiments, a camera may be disposed in or on the apparatus. The camera may transmit signal to a viewing station, such as a computer, that may be disposed in the line of sight of the device operator. The image or images transmitted by the camera may assist the operator in treating the skin.

A system may further include a fluid system coupled to the ablation members to facilitate removal of tissue portions or to irrigate the skin portion, e.g., with saline or a phosphate buffered solution; a heat source (e.g., a resistive heater or current) in communication with one or more ablation members to promote cauterization of ablation of tissue portions; and/or an optical element (e.g., a lens, a prism, a reflector, etc.) to facilitate viewing of the skin.

Configurations

Systems of the invention may include a variety of components in different configurations. For example, systems may include a reservoir for collecting waste materials (e.g., tissue, blood, and/or interstitial fluids) as well as a base unit. The reservoir may be disposed in the base unit, in the main body, in the tip, or in a separate module disposed between the tip and the main body or external to the apparatus and base unit components. Similarly, a pressure generating source (e.g., a vacuum pump) may be disposed external to other components or may be integrated into the main body or the base unit. Mechanisms for actuation, translation, and/or position detection; control electronics; and/or user interface(s) may be included in the main body and/or the base unit. These configurations facilitate the sterilization of the apparatus and/or system components as needed for patient treatment.

Figure 11:
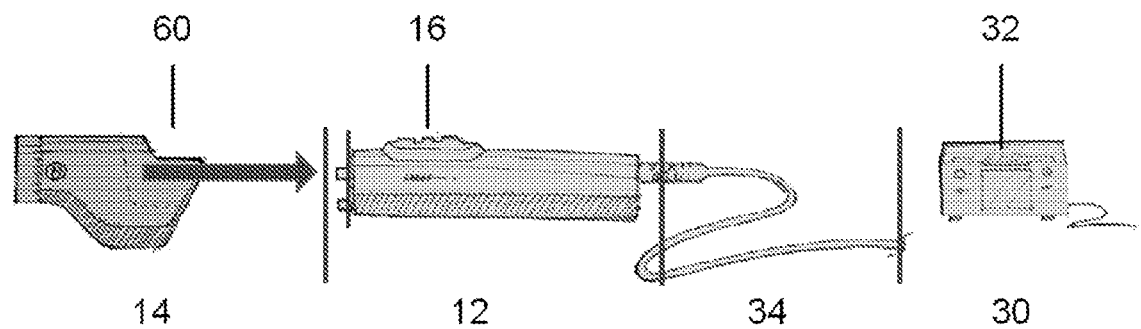
FIG. 11 shows a system of the invention that includes a tip 14 with an integrated reservoir for waste collection 60, a handheld main body 12 with a user interface 16, a cable 34 for carrying one or more of power, information, and suction, and a base unit 30 that includes a user interface 32.

FIG. 11 is a schematic illustrating a possible configuration of a system including reservoir 60, main body 12 with user interface 16, base unit 30 with user interface 32, and cable 34. In this system, the reservoir is integrated into detachably attachable tip 14, which is designed for a single use. The needles included in tip 14 are hollow and include one or more holes that are in fluid communication with reservoir 60. Reservoir 60 is further in fluid communication with a vacuum pump, such as an oil-free scroll pump, disposed in the base unit via tubing (e.g., nylon or Teflon tubing). A filter, such as a stainless steel sterilizing grade filter membrane (Mott Corporation), can be used to prevent materials from exiting the reservoir and aspirating in the vacuum pump. The base unit may include control electronics, a power supply, and a user interface that permit powering of the base unit and apparatus; activation of actuators disposed in the main body that cause translation of the skin-penetrating component across the skin and/or penetration into the skin by the needles; control of the displacement and speed of translation across the skin and the depth of penetration into the skin by the needles; the application of vacuum; and other parameters. The cable coupling the base unit and the apparatus is capable of carrying power, information, and vacuum, and facilitates interaction between the user interfaces of the main body and the base unit. Activators, such as buttons and scroll wheels on the handheld main body, can be used to activate the device by the operator with his or her hand(s) to allow easy and controlled operation. The actuators may also be digitally controlled (e.g., at a user interface). As such, operation of the system may be entirely or almost entirely controllable by features of the apparatus.

Treatment of a region of skin of a patient may proceed by supplying power to the vacuum pump, if present, and other components of the system, preparing the skin region for treatment (e.g., sterilizing and/or positioning the skin), placing the skin-penetrating component of the apparatus upon the skin in the treatment region, and activating the mechanism that drives penetration of the ablation members (e.g., needles, such as hollow coring needles) of the skin-penetrating component into the skin. The operator may activate the vacuum source, if present, to remove waste materials (e.g., tissue, blood, and/or interstitial fluids) from the treatment area and/or ablation members with an activator, such as a button, e.g., disposed on the main body. Alternatively, the activation of the vacuum source, if present, may be automatically trigged by the apparatus when the ablation members are inserted into or retracted from the skin. Removal of waste materials may proceed by suctioning the waste materials into the reservoir via holes in the ablation members (e.g., through the hollow lumen of a coring needle). Application of vacuum may be ceased prior to translation of the skin-penetrating component to an adjacent skin region for further treatment. The process may be repeated until the entire skin region of interest has been treated, at which point the tip can be detached from the main body via a quick-release mechanism, the tip disposed of, and the other components of the system sterilized as needed. Such treatment may provide a plurality of tissue portions with dimensions, geometries, and other characteristics corresponding to the dimensions, geometries, and other characteristics of the ablation members. For example, hollow coring needles inserted about 2 mm into the skin may provide tissue portions having a depth or length of about 2 mm.

A system of the invention with a similar configuration might, alternatively, integrate a miniature vacuum pump into the main body of the apparatus. In this instance, a cable coupling the main body and the base unit might be used to carry power and information but not suction. A miniature vacuum pump may have lower power requirements than a larger vacuum pump. In another related embodiment, actuation and/or translation mechanisms may be disposed in or on the main body instead of in or on the base unit.

Figure 12:
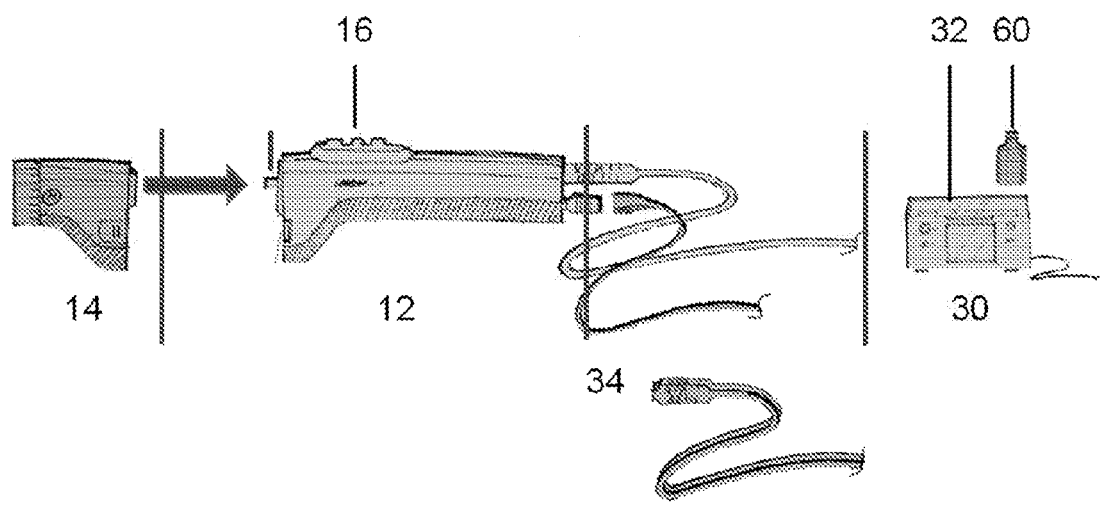
FIG. 12 shows a system of the invention that includes a tip 14, a handheld main body 12 with a user interface 16; one or more cables 34 for carrying one or more of power, information, and suction, and a base unit 30 that includes a user interface 32 and a reservoir for waste collection 60.

In another embodiment, the reservoir may be a component of the base unit. This configuration of the system permits collection of a larger volume of waste. FIG. 12 is a schematic of such a system that includes main body 12 with user interface 16 that couples to base unit 30 with user interface 32 and reservoir 60 via one or more cables 34 (note that here, as in all other figures, components may not be drawn to scale). Main body 12 further couples to detachably attachable tip 14.

In this system, one or more cables capable of providing power, information, and/or suction or vacuum act as conduits for waste between the handheld apparatus and the base unit. The cable or tubing for waste extends through the main body and is configured to be in fluid communication with the ablation members of the skin-penetrating component of the tip, which may be hollow needles having one or more holes (e.g., a central, longitudinal hole along the axis of the needle). The vacuum source may be disposed in the base unit or external to the system; for example, the vacuum source may be a medical or house vacuum source. Alternatively, the vacuum source may be a pump, such as a scroll, momentum transfer, rotary, diffusion, or diaphragm pump disposed within the base unit. The base unit of a system, such as that shown in FIG. 12, may further include a power supply, control electronics, and/or actuation, translation, and/or position detection mechanisms. Actuation, translation, and/or position detection mechanisms may, alternatively, be disposed within main body 12. User interfaces 16 and 32 may interact and/or reflect changes made at the other user interface. User action at user interface 16, including depression or activation of buttons, key switches, toggles, touch screens, scroll wheels, and/or other components may be performed with the hands.

Figure 13:
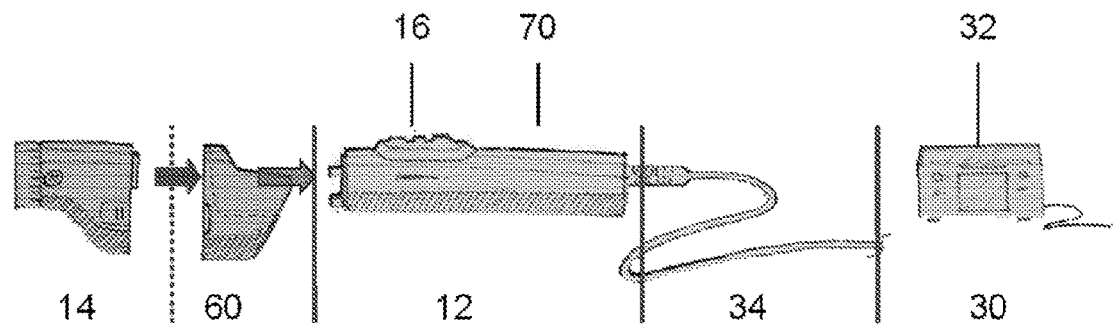
FIG. 13 shows a system of the invention that includes a tip 14, a module including a reservoir for waste collection 60, a handheld main body 12 with a user interface 16 and a miniature vacuum source 70, a cable 34 for carrying one or more of power, information, and suction, and a base unit 30 that includes a user interface 32.
Figure 14:
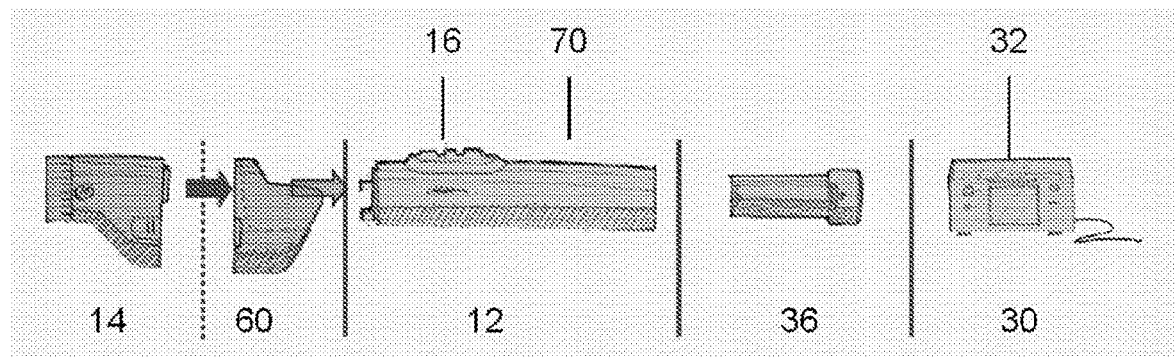
FIG. 14 shows a system of the invention includes a tip 14, a module including a reservoir for waste collection 60, a handheld main body 12 with a user interface 16 and a miniature vacuum source 70, a battery unit 36, and a base unit 30 that includes a user interface 32.

In an alternative embodiment, a module coupling to the tip and/or handheld device may include the reservoir. This module may be an element of the tip. A system of the invention having reservoir 60 disposed in such a module is schematically depicted in FIG. 13. In the system shown, the module is detachably attached to both tip 14 and main body 12 via, e.g., a quick-release mechanism to allow for easy sterilization and/or disposal of both the tip and the reservoir. The reservoir may be an element or the entirety of the module. A miniature vacuum source 70 may be disposed in the main body of the apparatus. The ablation members of the skin-penetrating component, the reservoir, and the vacuum source are all in fluid communication; a filter may be disposed in the reservoir, module, and/or main body to block waste materials, such as tissue, from aspirating into the vacuum source. The base unit may include a user interface as well as control electronics and actuation, translation, and/or position detection mechanisms. Cable 34 couples main body 12 and base unit 30 and carries power and information therebetween. In some embodiments, cable 34 is not present and the apparatus is powered by batteries that may be disposed in main body 12. FIG. 14 schematically depicts a system of the invention that includes battery pack 36 that may insert into main body 12. The apparatus may be charged by either removing the batteries from their housing, e.g., to be charged in a battery charging unit, or by placing the device in a battery charging station of the system. The apparatus and/or base unit 30 may also include components that allow for wireless communication therebetween.

Ablation Members

The invention features a tip and/or cartridge having one or more ablation members (e.g., needles (e.g., hollow coring needles), drill bits, abrading elements, punches, blades, and/or fluid jets) configured for penetration into and retraction from skin. These ablation members may be of varying number and characteristics and may be arranged in various configurations.

Needles

Ablation members of the invention are preferably needles. Needles of the invention may include and/or be formed of a variety of materials (e.g., any described herein). For example, the needles may be made of molded plastic, metal, or glass. The needles may also have coatings including chemical coatings. Such coatings may include therapeutic agents as described above.

Needles may be of varying sizes and geometries. For example, needles may be hollow coring needles. Needles may be of any gauge, including gauges between 19 and 26 (e.g., 19, 20, 21, 22, 23, 24, 25, and 26 gauge). In a preferred embodiment, the needles are 24 gauge needles. In another preferred embodiment, the needles are 22 gauge needles. The outer and/or inner diameter of the needles may vary across their lengths, such that the diameter of one region of a needle may be different from the outer and/or inner diameter of another region of said same needle. The change in a diameter across the needles may or may not be continuous. The outer and/or inner diameter of the needles at their widest point may be between about 0.01 mm to about 2 mm (e.g., 0.01 mm to 0.1 mm, 0.01 mm to 0.5 mm, 0.01 mm to 1 mm, 0.01 mm to 1.5 mm, 0.01 mm to 1.75 mm, 0.05 mm to 0.1 mm, 0.05 mm to 0.5 mm, 0.05 mm to 1 mm, 0.05 mm to 1.5 mm, 0.05 mm to 1.75 mm, 0.05 mm to 2 mm, 0.1 mm to 0.5 mm, 0.1 mm to 1 mm, 0.1 mm to 1.5 mm, 0.1 mm to 1.75 mm, 0.1 mm to 2 mm, 0.3 mm to 0.5 mm, 0.3 mm to 1 mm, 0.3 mm to 1.5 mm, 0.3 mm to 1.75 mm, 0.3 mm to 2 mm, 0.5 mm to 1 mm, 0.5 mm to 1.5 mm, 0.5 mm to 1.75 mm, 0.5 mm to 2 mm, 0.7 mm to 1 mm, 0.7 mm to 1.5 mm, 0.7 mm to 1.75 mm, 0.7 mm to 2 mm, 1 mm to 1.5 mm, 1 mm to 1.75 mm, 1 mm to 2 mm, 1.5 mm to 1.75 mm, 1.5 mm to 2 mm, and 1.75 mm to 2 mm). The needles may or may not be entirely partially cylindrical. For example, one or more needles may be rectangular, serrated, scalloped, and/or irregular in one or more dimension and along some or all of their lengths. In some embodiments, the inner lumen diameter may vary along the length of a needle. For example, the inner diameter may be wider at the distal end of the needle (e.g., away from the tip that penetrates the skin). This may facilitate the removal of tissue from the treatment area and/or the needles themselves and may limit the need for clearing of the ablation member using a pressure generating source (e.g., a vacuum source).

The needles may be configured to provide tissue portions. For example, penetration into and/or retraction from tissue by the needles may result in ablated tissue portions. The dimensions, geometry, number, and other characteristics of a tissue portion should correspond to the dimensions, geometry, number, and other characteristics of the skin penetrating component of the invention (e.g., the needle or array of needles). For example, a tissue portion created by penetration into the skin with a cylindrical, coring needle may have a cylindrical geometry, while a tissue portion created by penetration into the skin with a serrated ablation member may have a serrated or irregular geometry.

Needles of the invention may be configured to provide tissue portions having a change in width as a function of depth. For example, the part of an ablated tissue portion that originates from deeper tissue may be narrower than that part that originates from tissue closer to the skin surface. This change in width may be between about 100 μm to about 500 μm as a function of depth (e.g., 100 μm to 200 μm, 100 μm to 300 μm, 100 μm to 400 μm, 100 μm to 500 μm, 200 μm to 300 μm, 200 μm to 400 μm, 200 μm to 500 μm, 300 μm to 400 μm, 300 μm to 500 μm, and 400 μm to 500 μm). The needles may be configured to provide ablated tissue portions having a width to depth ratio between about 1:0.3 to about 1:75. For example, the width to depth radio of a tissue portion may be between about 1:0.3 to about 1:1 (e.g., 1:0.3 to 1:1, 1:0.35 to 1:1, 1:0.4 to 1:1, 1:0.45 to 1:1, 1:0.5 to 1:1, 1:0.55 to 1:1, 1:0.6 to 1:1, 1:0.65 to 1:1, 1:0.7 to 1:1, 1:0.75 to 1:1, 1:0.8 to 1:1, 1:0.85 to 1:1, 1:0.9 to 1:1, 1:0.95 to 1:1, 1:0.3 to 1:0.95, 1:0.35 to 1:0.95, 1:0.4 to 1:0.95, 1:0.45 to 1:0.95, 1:0.5 to 1:0.95, 1:0.55 to 1:0.95, 1:0.6 to 1:0.95, 1:0.65 to 1:0.95, 1:0.7 to 1:0.95, 1:0.75 to 1:0.95, 1:0.8 to 1:0.95, 1:0.85 to 1:0.95, 1:0.9 to 1:0.95, 1:0.3 to 1:0.9, 1:0.35 to 1:0.9, 1:0.4 to 1:0.9, 1:0.45 to 1:0.9, 1:0.5 to 1:0.9, 1:0.55 to 1:0.9, 1:0.6 to 1:0.9, 1:0.65 to 1:0.9, 1:0.7 to 1:0.9, 1:0.75 to 1:0.9, 1:0.8 to 1:0.9, 1:0.85 to 1:0.9, 1:0.3 to 1:0.85, 1:0.35 to 1:0.85, 1:0.4 to 1:0.85, 1:0.45 to 1:0.85, 1:0.5 to 1:0.85, 1:0.55 to 1:0.85, 1:0.6 to 1:0.85, 1:0.65 to 1:0.85, 1:0.7 to 1:0.85, 1:0.75 to 1:0.85, 1:0.8 to 1:0.85, 1:0.3 to 1:0.8, 1:0.35 to 1:0.8, 1:0.4 to 1:0.8, 1:0.45 to 1:0.8, 1:0.5 to 1:0.8, 1:0.55 to 1:0.8, 1:0.6 to 1:0.8, 1:0.65 to 1:0.8, 1:0.7 to 1:0.8, 1:0.75 to 1:0.8, 1:0.3 to 1:0.75, 1:0.35 to 1:0.75, 1:0.4 to 1:0.75, 1:0.45 to 1:0.75, 1:0.5 to 1:0.75, 1:0.55 to 1:0.75, 1:0.6 to 1:0.75, 1:0.65 to 1:0.75, 1:0.7 to 1:0.75, 1:0.3 to 1:0.65, 1:0.35 to 1:0.65, 1:0.4 to 1:0.65, 1:0.45 to 1:0.65, 1:0.5 to 1:0.65, 1:0.55 to 1:0.65, 1:0.6 to 1:0.65, 1:0.3 to 1:0.65, 1:0.35 to 1:0.65, 1:0.4 to 1:0.65, 1:0.45 to 1:0.65, 1:0.5 to 1:0.65, 1:0.55 to 1:0.65, 1:0.6 to 1:0.65, 1:0.3 to 1:0.6, 1:0.35 to 1:0.6, 1:0.4 to 1:0.6, 1:0.45 to 1:0.6, 1:0.5 to 1:0.6, 1:0.55 to 1:0.6, 1:0.3 to 1:0.55, 1:0.35 to 1:0.55, 1:0.4 to 1:0.55, 1:0.45 to 1:0.55, 1:0.5 to 1:0.55, 1:0.3 to 1:0.5, 1:0.35 to 1:0.5, 1:0.4 to 1:0.5, 1:0.45 to 1:0.5, 1:0.5 to 1:0.5, 1:0.3 to 1:0.45, 1:0.35 to 1:0.45, 1:0.4 to 1:0.45, 1:0.3 to 1:0.4, 1:0.35 to 1:0.4, and 1:0.3 to 1:0.35); between about 1:1 to about 1:20 (e.g., 1:1 to 1:2, 1:1 to 1:3, 1:1 to 1:4, 1:1 to 1:5, 1:1 to 1:6, 1:1 to 1:7, 1:1 to 1:8, 1:1 to 1:9, 1:1 to 1:10, 1:1 to 1:11, 1:1 to 1:12, 1:1 to 1:13, 1:1 to 1:14, 1:1 to 1:15, 1:1 to 1:16, 1:1 to 1:17, 1:1 to 1:18, 1:1 to 1:19, 1:1 to 1:20, 1:2 to 1:3, 1:2 to 1:4, 1:2 to 1:5, 1:2 to 1:6, 1:2 to 1:7, 1:2 to 1:8, 1:2 to 1:9, 1:2 to 1:10, 1:2 to 1:11, 1:2 to 1:12, 1:2 to 1:13, 1:2 to 1:14, 1:2 to 1:15, 1:2 to 1:16, 1:2 to 1:17, 1:2 to 1:18, 1:2 to 1:19, 1:2 to 1:20, 1:3 to 1:4, 1:3 to 1:5, 1:3 to 1:6, 1:3 to 1:7, 1:3 to 1:8, 1:3 to 1:9, 1:3 to 1:10, 1:3 to 1:11, 1:3 to 1:12, 1:3 to 1:13, 1:3 to 1:14, 1:3 to 1:15, 1:3 to 1:16, 1:3 to 1:17, 1:3 to 1:18, 1:3 to 1:19, 1:3 to 1:20, 1:4 to 1:5, 1:4 to 1:6, 1:4 to 1:7, 1:4 to 1:8, 1:4 to 1:9, 1:4 to 1:10, 1:4 to 1:11, 1:4 to 1:12, 1:4 to 1:13, 1:4 to 1:14, 1:4 to 1:15, 1:4 to 1:16, 1:4 to 1:17, 1:4 to 1:18, 1:4 to 1:19, 1:4 to 1:20, 1:5 to 1:6, 1:5 to 1:7, 1:5 to 1:8, 1:5 to 1:9, 1:5 to 1:10, 1:5 to 1:11, 1:5 to 1:12, 1:5 to 1:13, 1:5 to 1:14, 1:5 to 1:15, 1:5 to 1:16, 1:5 to 1:17, 1:5 to 1:18, 1:5 to 1:19, 1:5 to 1:20, 1:6 to 1:7, 1:6 to 1:8, 1:6 to 1:9, 1:6 to 1:10, 1:6 to 1:11, 1:6 to 1:12, 1:6 to 1:13, 1:6 to 1:14, 1:6 to 1:15, 1:6 to 1:16, 1:6 to 1:17, 1:6 to 1:18, 1:6 to 1:19, 1:6 to 1:20, 1:7 to 1:8, 1:7 to 1:9, 1:7 to 1:10, 1:7 to 1:11, 1:7 to 1:12, 1:7 to 1:13, 1:7 to 1:14, 1:7 to 1:15, 1:7 to 1:16, 1:7 to 1:17, 1:7 to 1:18, 1:7 to 1:19, 1:7 to 1:20, 1:8 to 1:9, 1:8 to 1:10, 1:8 to 1:11, 1:8 to 1:12, 1:8 to 1:13, 1:8 to 1:14, 1:8 to 1:15, 1:8 to 1:16, 1:8 to 1:17, 1:8 to 1:18, 1:8 to 1:19, 1:8 to 1:20, 1:9 to 1:10, 1:9 to 1:11, 1:9 to 1:12, 1:9 to 1:13, 1:9 to 1:14, 1:9 to 1:15, 1:9 to 1:16, 1:9 to 1:17, 1:9 to 1:18, 1:9 to 1:19, 1:9 to 1:20, 1:10 to 1:11, 1:10 to 1:12, 1:10 to 1:13, 1:10 to 1:14, 1:10 to 1:15, 1:10 to 1:16, 1:10 to 1:17, 1:10 to 1:18, 1:10 to 1:19, 1:10 to 1:20, 1:11 to 1:12, 1:11 to 1:13, 1:11 to 1:14, 1:11 to 1:15, 1:11 to 1:16, 1:11 to 1:17, 1:11 to 1:18, 1:11 to 1:19, 1:11 to 1:20, 1:12 to 1:13, 1:12 to 1:14, 1:12 to 1:15, 1:12 to 1:16, 1:12 to 1:17, 1:12 to 1:18, 1:12 to 1:19, 1:12 to 1:20, 1:13 to 1:14, 1:13 to 1:15, 1:13 to 1:16, 1:13 to 1:17, 1:13 to 1:18, 1:13 to 1:19, 1:13 to 1:20, 1:14 to 1:15, 1:14 to 1:16, 1:14 to 1:17, 1:14 to 1:18, 1:14 to 1:19, 1:14 to 1:20, 1:15 to 1:16, 1:15 to 1:17, 1:15 to 1:18, 1:15 to 1:19, 1:15 to 1:20, 1:17 to 1:18, 1:17 to 1:19, and 1:17 to 1:20); between about 1:1 to about 1:75 (e.g., 1:1 to 1:2, 1:1 to 1:5, 1:1 to 1:10, 1:1 to 1:20, 1:1 to 1:30, 1:1 to 1:40, 1:1 to 1:50, 1:1 to 1:60, 1:1 to 1:75, 1:2 to 1:5, 1:2 to 1:10, 1:2 to 1:20, 1:2 to 1:30, 1:2 to 1:40, 1:2 to 1:50, 1:2 to 1:60, 1:2 to 1:75, 1:5 to 1:10, 1:5 to 1:20, 1:5 to 1:30, 1:5 to 1:40, 1:5 to 1:50, 1:5 to 1:60, 1:5 to 1:75, 1:10 to 1:20, 1:10 to 1:30, 1:10 to 1:40, 1:10 to 1:50, 1:10 to 1:60, 1:10 to 1:75, 1:20 to 1:30, 1:20 to 1:40, 1:20 to 1:50, 1:20 to 1:60, 1:20 to 1:75, 1:30 to 1:40, 1:30 to 1:50, 1:30 to 1:60, 1:30 to 1:75, 1:40 to 1:50, 1:40 to 1:60, 1:40 to 1:75, 1:50 to 1:60, 1:50 to 1:75, and 1:60 to 1:75); between about 1:25 to about 1:75 (e.g., 1:25 to 1:75, 1:30 to 1:75, 1:35 to 1:75, 1:40 to 1:75, 1:45 to 1:75, 1:50 to 1:75, 1:55 to 1:75, 1:60 to 1:75, 1:65 to 1:75, 1:70 to 1:75, 1:25 to 1:70, 1:30 to 1:70, 1:35 to 1:70, 1:40 to 1:70, 1:45 to 1:70, 1:50 to 1:70, 1:55 to 1:70, 1:60 to 1:70, 1:65 to 1:70, 1:25 to 1:65, 1:30 to 1:65, 1:35 to 1:65, 1:40 to 1:65, 1:45 to 1:65, 1:50 to 1:65, 1:55 to 1:65, 1:60 to 1:65, 1:25 to 1:60, 1:30 to 1:60, 1:35 to 1:60, 1:40 to 1:60, 1:45 to 1:60, 1:50 to 1:60, 1:55 to 1:60, 1:25 to 1:55, 1:30 to 1:55, 1:35 to 1:55, 1:40 to 1:55, 1:45 to 1:55, 1:50 to 1:55, 1:25 to 1:50, 1:30 to 1:50, 1:35 to 1:50, 1:40 to 1:50, 1:45 to 1:50, 1:25 to 1:45, 1:30 to 1:45, 1:35 to 1:45, 1:40 to 1:45, 1:25 to 1:40, 1:30 to 1:40, 1:35 to 1:40, 1:25 to 1:35, 1:30 to 1:35, and 1:25 to 1:30); or between about 1:03 to about 1:75 (e.g., 1:0.3 to 1:0.5, 1:0.3 to 1:1, 1:0.3 to 1:2, 1:0.3 to 1:5, 1:0.3 to 1:10, 1:0.3 to 1:20, 1:0.3 to 1:30, 1:0.3 to 1:40, 1:0.3 to 1:50, 1:0.3 to 1:60, 1:0.3 to 1:75, 1:0.5 to 1:1, 1:0.5 to 1:2, 1:0.5 to 1:5, 1:0.5 to 1:10, 1:0.5 to 1:20, 1:0.5 to 1:30, 1:0.5 to 1:40, 1:0.5 to 1:50, 1:0.5 to 1:60, and 1:0.5 to 1:75).

Needles may be of varying lengths and may have varying active lengths (i.e., the length of needle configured to penetrate the skin). Active lengths may vary between about 0.1 mm to about 15 mm (e.g., 0.1 mm to 0.2 mm, 0.1 mm to 0.5 mm, 0.1 mm to 1 mm, 0.1 mm to 2 mm, 0.1 mm to 5 mm, 0.1 mm to 10 mm, 0.1 mm to 15 mm, 0.2 mm to 0.5 mm, 0.2 mm to 1 mm, 0.2 mm to 2 mm, 0.2 mm to 5 mm, 0.2 mm to 10 mm, 0.2 mm to 15 mm, 0.5 mm to 1 mm, 0.5 mm to 2 mm, 0.5 mm to 5 mm, 0.5 mm to 10 mm, 0.5 mm to 15 mm, 1 mm to 2 mm, 1 mm to 5 mm, 1 mm to 10 mm, 1 mm to 15 mm, 2 mm to 5 mm, 2 mm to 10 mm, 2 mm to 15 mm, 5 mm to 10 mm, 5 mm to 15 mm, and 10 mm to 15 mm) and may be selectable with manual or automatic controls (e.g., a scroll wheel or an actuation mechanism such as an electromagnetic actuator). Needle parameters may be selected based on the area of skin and the condition to be treated. For example, treatment of thin, lax skin on the cheeks may benefit from coring needles having active lengths of about 2 mm and medium gauge (e.g., 22 gauge), while treatment of thick skin on the back may benefit from coring needles having lengths closer to 15 mm and thicker gauges (e.g., 26 gauge).

The needles of the invention may or may not be hollow. Hollow needles may have a plurality of holes. For example, needles may have holes at either end and/or along their lengths. The needles may include and/or be coated with chemical or biological materials to treat skin. In some embodiments, holes in the needles may facilitate the injection of chemical or bioactive agents into tissue. Such agents may be injected at multiple depths or at specific areas along the needles or in specific patterns. The size of the needle holes may control the amount of chemical or bioactive agents delivered to particular locations. In some embodiments, chemical or bioactive agents may be used to destroy or ablate skin tissue. Typical chemical or bioactive agents used include trichloroacetic acid, alpha hydroxy acids, beta hydroxy acids, liquid nitrogen, hypoosmotic fluids, hyperosmotic fluids, and bioactive proteins (e.g., one or more hormones, antibodies, and/or enzymes, such as enzymes that liquefy tissue, such as one or more proteases, DNases, hyaluronidase, and collagenases, or combinations thereof). Chemicals or bioactive agents may be used to create an injury, ablated tissue portion, and/or stimulate new tissue formation. Chemicals or bioactive agents may also include fillers, such as collagen-based fillers.

Figure 15:
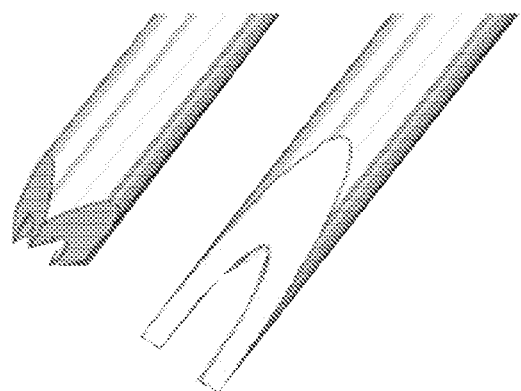
FIG. 15 shows possible needle tip configurations for the ablation members of the tip of the apparatus of the invention.

Needles may include one or more barbs on either their outer or inner surfaces. The ends (tips) of the needles configured to penetrate the skin may be sharpened to a fine point or otherwise configured. Two possible needle tip configurations are shown in FIG. 15.

The needles may be coupled to other components of an apparatus, system, or kit such as a reservoir for collecting waste materials and/or a pressure generating source. Coring needles may be in fluid communication with such components to facilitate the removal of ablated tissue, for example. The needles may also be coupled to a substrate disposed in the tip. The substrate may enforce the needle array configuration and sufficiently bind the needles to prevent the needles from becoming stuck or left behind in the skin upon penetration. A substrate may include adhesive and/or mechanical coupling components and materials such as glues or plastic overmoldings. The needles may further be electrically and/or mechanically coupled to actuation mechanisms to drive the needles across and into the skin surface. A coupling mechanism may include an array gripper.

Arrays

When a tip has more than one ablation member (e.g., needle), the ablation members may be configured to form a one- or two-dimensional array (including linear, radial, rectangular, and irregular arrays). The size and geometry of an array may be selected based on the area of skin and condition being treated. For example, a small array may be selected for treatment of the peri-oral area, while a large array may be suitable for treatment of the abdomen. Arrays of the same size may feature different numbers and/or arrangements of ablation members (e.g., needles). For example, one linear array may include five needles spaced about 2 mm apart while another linear array may include ten needles spaced about 1 mm apart. The main body may be configured for detachable attachment to a variety of tips having different numbers and configurations of ablation members. Also, the tip housing and/or structure may be configured for inclusion of arrays of varying sizes and geometries.

The tip may have as few as 1 or as many as hundreds of ablation members (e.g., needles). In some embodiments, 1-100 ablation members may be present (e.g., 1-10, 1-20, 1-30, 1-40, 1-50, 1-60, 1-70, 1-80, 1-90, 1-100, 3-10, 3-20, 3-30, 3-40, 3-50, 3-60, 3-70, 3-80, 3-90, 3-100, 5-10, 5-20, 5-30, 5-40, 5-50, 5-60, 5-70, 5-80, 5-90, 5-100, 10-20, 10-40, 10-60, 10-80, 10-100, 20-40, 20-60, 20-80, 20-100, 40-60, 40-80, 40-100, 60-80, 60-100, or 80-100 ablation members). In preferred embodiments, the tip may have 3-50 ablation members (e.g., needles). The use of an array of multiple ablation members may facilitate skin treatment over larger areas and in less time.

The minimum distance between two ablation members (e.g., needles) in an array may be between about 0.1 mm to about 50 mm (e.g., from 0.1 mm to 0.2 mm, 0.1 mm to 0.5 mm, 0.1 mm to 1 mm, 0.1 mm to 2 mm, 0.1 mm to 5 mm, 0.1 mm to 10 mm, 0.1 mm to 15 mm, 0.1 mm to 20 mm, 0.1 mm to 30 mm, 0.1 mm to 40 mm, 0.1 mm to 50 mm, 0.2 mm to 0.5 mm, 0.2 mm to 1 mm, 0.2 mm to 2 mm, 0.2 mm to 5 mm, 0.2 mm to 10 mm, 0.2 mm to 15 mm, 0.2 mm to 20 mm, 0.2 mm to 30 mm, 0.2 mm to 40 mm, 0.2 mm to 50 mm, 0.5 mm to 1 mm, 0.5 mm to 2 mm, 0.5 mm to 5 mm, 0.5 mm to 10 mm, 0.5 mm to 15 mm, 0.5 mm to 20 mm, 0.5 mm to 30 mm, 0.5 mm to 40 mm, 0.5 mm to 50 mm, 1 mm to 2 mm, 1 mm to 5 mm, 1 mm to 10 mm, 1 mm to 15 mm, 1 mm to 20 mm, 1 mm to 30 mm, 1 mm to 40 mm, 1 mm to 50 mm, 2 mm to 5 mm, 2 mm to 10 mm, 2 mm to 15 mm, 2 mm to 20 mm, 2 mm to 30 mm, 2 mm to 40 mm, 2 mm to 50 mm, 5 mm to 10 mm, 5 mm to 15 mm, 5 mm to 20 mm, 5 mm to 30 mm, 5 mm to 40 mm, 5 mm to 50 mm, 10 mm to 15 mm, 10 mm to 20 mm, 10 mm to 30 mm, 10 mm to 40 mm, 10 mm to 50 mm, 15 mm to 20 mm, 15 mm to 30 mm, 15 mm to 40 mm, 15 mm to 50 mm, 20 mm to 30 mm, 20 mm to 40 mm, 20 mm to 50 mm, 30 mm to 40 mm, 30 mm to 50 mm, and 40 mm to 50 mm). The minimum distance may correspond to the minimal size of an array, while the maximum distance may correspond to the maximum size of an array.

Arrays of different sizes and geometries may be selected based on the area of treatment and the skin condition being treated. Arrays may also be selected for compatibility with actuation mechanisms and control electronics of a given apparatus, system, or kit. Alternatively, actuation mechanisms and control electronics of an apparatus, system, or kit may be selected for compatibility with a desired array size and/or geometry. For example, a long, linear array may be used in combination with a translating mechanism with driving wheels, while a large, rectangular array may be used in combination with an x-actuator to drive the ablation members (e.g., needles) across the skin.

In any of the apparatuses, systems, kits, and methods herein, the tip may be configured to provide from about 10 to about 10000 ablated tissue portions per $cm^2$ area (e.g., 10 to 50, 10 to 100, 10 to 200, 10 to 300, 10 to 400, 10 to 500, 10 to 600, 10 to 700, 10 to 800, 10 to 900, 10 to 1000, 10 to 2000, 10 to 4000, 10 to 6000, 10 to 8000, 10 to 10000, 50 to 100, 50 to 200, 50 to 300, 50 to 400, 50 to 500, 50 to 600, 50 to 700, 50 to 800, 50 to 900, 50 to 1000, 50 to 2000, 50 to 4000, 510 to 6000, 50 to 8000, 50 to 10000, 100 to 200, 100 to 300, 100 to 400, 100 to 500, 100 to 600, 100 to 700, 100 to 800, 100 to 900, 100 to 1000, 100 to 2000, 100 to 4000, 100 to 6000, 100 to 8000, 100 to 10000, 200 to 300, 200 to 400, 200 to 500, 200 to 600, 200 to 700, 200 to 800, 200 to 900, 200 to 1000, 200 to 2000, 200 to 4000, 200 to 6000, 200 to 8000, 200 to 10000, 300 to 400, 300 to 500, 300 to 600, 300 to 700, 300 to 800, 300 to 900, 300 to 1000, 300 to 2000, 300 to 4000, 300 to 6000, 300 to 8000, 300 to 10000, 400 to 500, 400 to 600, 400 to 700, 400 to 800, 400 to 900, 400 to 1000, 400 to 2000, 400 to 4000, 400 to 6000, 400 to 8000, 400 to 10000, 500 to 600, 500 to 700, 500 to 800, 500 to 900, 500 to 1000, 500 to 2000, 500 to 4000, 500 to 6000, 500 to 8000, 500 to 10000, 600 to 700, 600 to 800, 600 to 900, 600 to 1000, 600 to 2000, 600 to 4000, 600 to 6000, 600 to 8000, 600 to 10000, 700 to 800, 700 to 900, 700 to 1000, 700 to 2000, 700 to 4000, 700 to 6000, 700 to 8000, 700 to 10000, 800 to 900, 800 to 1000, 800 to 2000, 800 to 4000, 800 to 6000, 800 to 8000, 800 to 10000, 900 to 1000, 900 to 2000, 900 to 4000, 900 to 6000, 900 to 8000, 900 to 10000, 1000 to 2000, 1000 to 4000, 1000 to 6000, 1000 to 8000, 1000 to 10000, 2000 to 4000, 2000 to 6000, 2000 to 8000, 2000 to 10000, 4000 to 6000, 4000 to 8000, 4000 to 10000, 6000 to 8000, 6000 to 10000, and 8000 to 10000 tissue portions per $cm^2$ area) of the skin region to which the apparatus is applied (e.g., treatment area). The tip may be configured to remove about 5%-70% (e.g., 5%, 10%, 15%, 20%, 25%, 30%, 35%, 40%, 45%, 50%, 55%, 60%, 65%, and 70%) of tissue within a treatment area. In a preferred embodiment, about 10% of tissue within a treatment area is removed.

In any of the apparatuses, systems, kits, and methods herein, one or more components of the device may be selected or designed to secure the ablation member(s) (e.g., one or more needles) and/or prevent or minimize angular movement (e.g., wobbling) of the ablation member(s). The needle(s) may be secured to a substrate so as to minimize or reduce angular movement of the needle(s) during insertion to less than 5 degrees, e.g., less than 4, 3, or 2 degrees. An angular movement of the needle(s) during insertion of ~1-1.5 degrees is within nominal tolerances, whereas an angular movement of the needle(s) during insertion of ~4-5 degrees or more is to be avoided, if possible. For example, components that join ablation member(s) to other components (e.g., a substrate) may be designed with low mechanical tolerances to firmly secure the ablation member(s). This may reduce the prevalence of or lower the risk of destabilization and/or reduction in the structural integrity of ablation member(s) that may result from repeated use. For example, firmly securing the needle(s) may prevent and/or minimize needle dulling, bending, and curling of needle tip(s) that could reduce the effectiveness of the needle(s). Firmly securing the needle(s) may also reduce the risk of overstriking (e.g., striking a hole produced by a needle more than once).

Ablated Tissue Portions

The present invention features apparatuses, systems, kits, and methods for generating ablated tissue portions having various geometric dimensions. The apparatuses, systems, kits, and methods of the invention can be configured to produce tissue portions by producing holes in the skin (e.g., by penetration with ablation members, such as hollow needles). The apparatuses, systems, kits, and methods of the invention can further be configured to provide tissue portions with specific dimensions, geometries, and other characteristics. Characteristics (e.g., dimensions, geometries, and other characteristics) of tissue portions may reflect the characteristics of holes formed in the skin. For example, an apparatus may be configured to produce a hole having a change in width or diameter as a function of depth (e.g., by use of ablation members, such as needles, having changes in width or diameter along their lengths), such that a corresponding tissue portion may also have a change in width or diameter as a function of depth. Certain width or depth ratios of one or more ablation members may allow for improvement of skin tightening (e.g., forming a hole having a larger diameter at the skin surface than at the skin depth may facilitate hole closing via mechanical hole closure or, alternatively, forming a hole having a smaller diameter at the skin surface than at the skin depth may accelerate closure of the epidermal layer (e.g., reepithelialization) and therefore minimize the risk of adverse events, such as infections, and minimize healing time), skin rejuvenation (e.g., skin texture, color, and/or architecture), treatment of thin skin regions (e.g., lower anterior leg and cheeks), and/or treatment of thick skin (e.g., anterior leg and gluteus). Using apparatuses, systems, kits, and methods with certain width to depth ratios may further minimize the risk of scarring while maximizing skin tightening. Such benefits may minimize healing time, improve treatment to abnormal skin areas (e.g., irregularly shaped and/or small treatment areas), and/or increase the ability to tune hole depth and diameter to the treatment objective. A provided tissue portion may have a width to depth ratio of between about 1:0.3 to about 1:75 (e.g., as described herein) and/or have a change in width as a function of depth between about 100 μm to about 500 μm (e.g., as described herein).

In some embodiments, the ablated tissue portions provided by apparatuses, systems, kits, and methods of the invention may have at least one dimension between about 10 μm and about 2 mm (e.g., about 10 μm to 500 μm, about 10 μm to 100 μm, 10 μm to 250 μm, 10 μm to 500 μm, 10 μm to 750 μm, 10 μm to 1 mm, 10 μm to 1.5 mm, 10 μm to 2 mm, about 50 μm to 100 μm, 50 μm to 250 μm, 50 μm to 500 μm, 50 μm to 750 μm, 50 μm to 1 mm, 50 μm to 1.5 mm, 50 μm to 2 mm, 100 μm to 250 μm, 100 μm to 500 μm, 100 μm to 750 μm, 100 μm tot mm, 100 μm to 1.5 mm, 100 μm to 2 mm, 250 μm to 500 μm, 250 μm to 750 μm, 250 μm to 1 mm, 250 μm to 1.5 mm, 250 μm to 2 mm, 500 μm to 750 μm, 500 μm to 1 mm, 500 μm to 1.5 mm, 500 μm to 2 mm, 750 μm to 1 mm, 750 μm to 1.5 mm, and 750 μm to 2 mm); between about 0.1 mm to about 0.8 mm (e.g., 0.1 mm to 0.8 mm, 0.1 mm to 0.6 mm, 0.1 mm to 0.4 mm, 0.1 mm to 0.2 mm, 0.2 mm to 0.8 mm, 0.2 mm to 0.6 mm, 0.2 mm to 0.4 mm, 0.2 mm to 0.3 mm, 0.3 mm to 0.8 mm, 0.3 mm to 0.6 mm, 0.3 mm to 0.4 mm, 0.4 mm to 0.8 mm, 0.4 mm to 0.6 mm, 0.4 mm to 0.5 mm, 0.5 mm to 0.8 mm, 0.5 mm to 0.6 mm, 0.6 mm to 0.8 mm, 0.6 mm to 0.7 mm, and 0.7 mm to 0.8 mm); between about 0.9 mm to about 20 mm (e.g., 0.9 mm to 20 mm, 0.9 mm to 17 mm, 0.9 mm to 14 mm, 0.9 mm to 11 mm, 0.9 mm to 8 mm, 0.9 mm to 5 mm, 0.9 mm to 3 mm, 3 mm to 20 mm, 3 mm to 17 mm, 3 mm to 14 mm, 3 mm to 11 mm, 3 mm to 8 mm, 3 mm to 5 mm, 5 mm to 20 mm, 5 mm to 17 mm, 5 mm to 14 mm, 5 mm to 11 mm, 5 mm to 8 mm, 8 mm to 20 mm, 8 mm to 17 mm, 8 mm to 14 mm, 8 mm to 11 mm, 11 mm to 20 mm, 11 mm to 17 mm, 11 mm to 14 mm, 14 mm to 20 mm, 14 mm to 17 mm, and 17 mm to 20 mm); between about 0.01 mm to 0.25 mm (e.g., 0.01 mm to 0.25 mm, 0.02 mm to 0.25 mm, 0.03 mm to 0.25 mm, 0.05 mm to 0.25 mm, 0.075 mm to 0.25 mm, 0.1 mm to 0.25 mm, 0.15 mm to 0.25 mm, 0.2 mm to 0.25 mm, 0.01 mm to 0.2 mm, 0.02 mm to 0.2 mm, 0.03 mm to 0.2 mm, 0.05 mm to 0.2 mm, 0.075 mm to 0.2 mm, 0.1 mm to 0.2 mm, 0.15 mm to 0.2 mm, 0.01 mm to 0.15 mm, 0.02 mm to 0.15 mm, 0.03 mm to 0.15 mm, 0.05 mm to 0.15 mm, 0.075 mm to 0.15 mm, 0.1 mm to 0.15 mm, 0.01 mm to 0.1 mm, 0.02 mm to 0.1 mm, 0.03 mm to 0.1 mm, 0.05 mm to 0.1 mm, 0.075 mm to 0.1 mm, 0.01 mm to 0.075 mm, 0.02 mm to 0.075 mm, 0.03 mm to 0.075 mm, 0.05 mm to 0.075 mm, 0.01 mm to 0.05 mm, 0.02 mm to 0.05 mm, 0.03 mm to 0.05 mm, 0.01 mm to 0.03 mm, 0.02 mm to 0.03 mm, 0.03 mm to 0.03 mm, 0.01 mm to 0.03 mm, 0.02 mm to 0.03 mm, and 0.01 mm to 0.02 mm); between about 0.01 mm to about 20 mm (e.g., 0.01 mm to 1 mm, 0.01 mm to 2 mm, 0.01 mm to 5 mm, 0.01 mm to 10 mm, 0.01 mm to 15 mm, 0.05 mm to 1 mm, 0.05 mm to 2 mm, 0.05 mm to 5 mm, 0.05 mm to 10 mm, 0.05 mm to 15 mm, 0.05 mm to 20 mm, 0.1 mm to 1 mm, 0.1 mm to 2 mm, 0.1 mm to 5 mm, 0.1 mm to 10 mm, 0.1 mm to 15 mm, 0.1 mm to 20 mm, 0.5 mm to 1 mm, 0.5 mm to 2 mm, 0.5 mm to 5 mm, 0.5 mm to 10 mm, 0.5 mm to 15 mm, 0.5 mm to 20 mm, 1 mm to 2 mm, 1 mm to 5 mm, 1 mm to 10 mm, 1 mm to 15 mm, 1 mm to 20 mm, 2 mm to 5 mm, 2 mm to 10 mm, 2 mm to 15 mm, 2 mm to 20 mm, 5 mm to 10 mm, 5 mm to 15 mm, and 5 mm to 20 mm); or between about 0.01 mm to about 2 mm (e.g., 0.01 mm to 0.1 mm, 0.01 mm to 0.5 mm, 0.01 mm to 1 mm, 0.01 mm to 1.5 mm, 0.01 mm to 1.75 mm, 0.05 mm to 0.1 mm, 0.05 mm to 0.5 mm, 0.05 mm to 1 mm, 0.05 mm to 1.5 mm, 0.05 mm to 1.75 mm, 0.05 mm to 2 mm, 0.1 mm to 0.5 mm, 0.1 mm to 1 mm, 0.1 mm to 1.5 mm, 0.1 mm to 1.75 mm, 0.1 mm to 2 mm, 0.3 mm to 0.5 mm, 0.3 mm to 1 mm, 0.3 mm to 1.5 mm, 0.3 mm to 1.75 mm, 0.3 mm to 2 mm, 0.5 mm to 1 mm, 0.5 mm to 1.5 mm, 0.5 mm to 1.75 mm, 0.5 mm to 2 mm, 0.7 mm to 1 mm, 0.7 mm to 1.5 mm, 0.7 mm to 1.75 mm, 0.7 mm to 2 mm, 1 mm to 1.5 mm, 1 mm to 1.75 mm, 1 mm to 2 mm, 1.5 mm to 1.75 mm, 1.5 mm to 2 mm, and 1.75 mm to 2 mm). For instance, the diameter or width of a tissue portion may be between about 0.01 mm and about 2 mm at its widest point (e.g., as described herein). For example, penetration into tissue by about 1 mm with a needle having a diameter of about 2 mm may produce a tissue portion having a depth or length of about 1 mm and a diameter of about 2 mm.

A tissue portion may have an area dimension in a range of about 0.001 mm$^2$ to about 2 mm$^2$ (e.g., 0.001 mm$^2$ to 0.005 mm$^2$, 0.001 mm$^2$ to 0.01 mm$^2$, 0.001 mm$^2$ to 0.05 mm$^2$, 0.001 mm$^2$ to 0.1 mm$^2$, 0.001 mm$^2$ to 0.5 mm$^2$, 0.001 mm$^2$ to 1 mm$^2$, 0.001 mm$^2$ to 1.5 mm$^2$, 0.001 mm$^2$ to 2 mm$^2$, 0.005 mm$^2$ to 0.01 mm$^2$, 0.005 mm$^2$ to 0.05 mm$^2$, 0.005 mm$^2$ to 0.1 mm$^2$, 0.005 mm$^2$ to 0.5 mm$^2$, 0.005 mm$^2$ to 1 mm$^2$, 0.005 mm$^2$ to 1.5 mm$^2$, 0.005 mm$^2$ to 2 mm$^2$, 0.01 mm$^2$ to 0.02 mm$^2$, 0.01 mm$^2$ to 0.05 mm$^2$, 0.01 mm$^2$ to 0.1 mm$^2$, 0.01 mm$^2$ to 0.5 mm$^2$, 0.01 mm$^2$ to 1 mm$^2$, 0.01 mm$^2$ to 1.5 mm$^2$, 0.01 mm$^2$ to 2 mm$^2$, 0.05 mm$^2$ to 0.1 mm$^2$, 0.05 mm$^2$ to 0.5 mm$^2$, 0.05 mm$^2$ to 1 mm$^2$, 0.05 mm$^2$ to 1.5 mm$^2$, 0.05 mm$^2$ to 2 mm$^2$, 0.1 mm$^2$ to 0.2 mm$^2$, 0.1 mm$^2$ to 0.5 mm$^2$, 0.1 mm$^2$ to 1 mm$^2$, 0.1 mm$^2$ to 1.5 mm$^2$, 0.1 mm$^2$ to 2 mm$^2$, 0.5 mm$^2$ to 1 mm$^2$, 0.5 mm$^2$ to 1.5 mm$^2$, 0.5 mm$^2$ to 2 mm$^2$, 1 mm$^2$ to 1.5 mm$^2$, 1 mm$^2$ to 2 mm$^2$, and 1.5 mm$^2$ to 2 mm$^2$) and/or a volume between about 0.001 mm$^3$ and about 6 mm$^3$ (e.g., 0.001 mm$^3$ to 0.01 mm$^3$, 0.001 mm$^3$ to 0.1 mm$^3$, 0.001 mm$^3$ to 0.5 mm$^3$, 0.001 mm$^3$ to 1 mm$^3$, 0.001 mm$^3$ to 2 mm$^3$, 0.001 mm$^3$ to 3 mm$^3$, 0.001 mm$^3$ to 4 mm$^3$, 0.001 mm$^3$ to 5 mm$^3$, 0.001 mm$^3$ to 6 mm$^3$, 0.005 mm$^3$ to 0.01 mm$^3$, 0.005 mm$^3$ to 0.1 mm$^3$, 0.005 mm$^3$ to 0.5 mm$^3$, 0.005 mm$^3$ to 1 mm$^3$, 0.005 mm$^3$ to 2 mm$^3$, 0.005 mm$^3$ to 3 mm$^3$, 0.005 mm$^3$ to 4 mm$^3$, 0.005 mm$^3$ to 5 mm$^3$, 0.005 mm$^3$ to 6 mm$^3$, 0.01 mm$^3$ to 0.1 mm$^3$, 0.01 mm$^3$ to 0.5 mm$^3$, 0.01 mm$^3$ to 1 mm$^3$, 0.01 mm$^3$ to 2 mm$^3$, 0.01 mm$^3$ to 3 mm$^3$, 0.01 mm$^3$ to 4 mm$^3$, 0.01 mm$^3$ to 5 mm$^3$, 0.01 mm$^3$ to 6 mm$^3$, 0.1 mm$^3$ to 0.5 mm$^3$, 0.1 mm$^3$ to 1 mm$^3$, 0.1 mm$^3$ to 2 mm$^3$, 0.1 mm$^3$ to 3 mm$^3$, 0.1 mm$^3$ to 4 mm$^3$, 0.1 mm$^3$ to 5 mm$^3$, 0.1 mm$^3$ to 6 mm$^3$, 0.5 mm$^3$ to 1 mm$^3$, 0.5 mm$^3$ to 2 mm$^3$, 0.5 mm$^3$ to 3 mm$^3$, 0.5 mm$^3$ to 4 mm$^3$, 0.5 mm$^3$ to 5 mm$^3$, 0.5 mm$^3$ to 6 mm$^3$, 1 mm$^3$ to 2 mm$^3$, 1 mm$^3$ to 3 mm$^3$, 1 mm$^3$ to 4 mm$^3$, 1 mm$^3$ to 5 mm$^3$, 1 mm$^3$ to 6 mm$^3$, 2 mm$^3$ to 3 mm$^3$, 2 mm$^3$ to 4 mm$^3$, 2 mm$^3$ to 5 mm$^3$, 2 mm$^3$ to 6 mm$^3$, 3 mm$^3$ to 4 mm$^3$, 3 mm$^3$ to 5 mm$^3$, 3 mm$^3$ to 6 mm$^3$, 4 mm$^3$ to 5 mm$^3$, 4 mm$^3$ to 6 mm$^3$, and 5 mm$^3$ to 6 mm$^3$).

The ablated tissue portion can have any combination of the dimensions described herein. For instance, in some non-limiting embodiments, the ablated tissue portion has at least one dimension that is less than about 2 mm and an area dimension that is less than about 2 mm$^2$. In other embodiments, the ablated tissue portion has at least one dimension that is less than about 2 mm and a volumetric dimension that is less than about 6 mm$^3$. In yet other embodiments, the ablated tissue portion has at least one dimension that is less than about 2 mm and an area dimension that is less than about 2 mm$^2$ and a volumetric dimension that is less than about 6 mm$^3$. In some embodiments, the ablated tissue portion has an aerial dimension that is less than about 2 mm$^2$ and a volumetric dimension that is less than about 6 mm$^3$.

Ablation Kit

The invention also features kits for skin tightening and/or for treating diseases, disorders, and conditions that would benefit from skin restoration or tightening. Kits may include one or more tips and or cartridges including skin-penetrating components with one or more ablation members (e.g., coring needles) configured for penetration into and retraction from skin as well as a main body of the apparatus configured for handheld operation. As described above, tips in a kit may be configured to be detachably attached to the main body. The ablation members of a tip may be configured to be in fluid communication with a pressure generating source (e.g., a vacuum pump), such as when a tip is attached to a main body.

Kits of the invention may include additional components, such as a reservoir for collecting waste materials (e.g., tissue, blood, and/or interstitial fluids); a pressure generating source; mechanisms for actuation, translation, and position detection (e.g., one or more pneumatic, electromagnetic, and/or piezoelectric actuators; driving wheels; and/or a camera); a base unit; and a skin positioning apparatus (e.g., tensioning rods). In addition, kits of the invention may include any other useful components, such as instructions on how to use the device(s), an air blower, a heating element (e.g., a heat gun or heating pad), one or more therapeutic agents (e.g., any described herein, such as an anticoagulative and/or procoagulative agent, and optionally in combination with a useful dispenser for applying the therapeutic agent, such as a brush, spray, film, ointment, cream, lotion, or gel), one or more wound cleansers (e.g., including any antibiotic, antimicrobial, or antiseptic, such as those described herein, in any useful form, such as a brush, spray, film, ointment, cream, lotion, or gel), one or more compression dressings, one or more closures (e.g., bandage, hemostats, sutures, or adhesives), one or more debriding agents, one or more adhesives (e.g., any described herein), one or more cosmetics (e.g., as described herein), and/or other suitable or useful materials.

Kits of the invention may also feature one or more replacement tips (e.g., one or more tips of a single configuration or of different configurations). Kits may be packaged with the tip in sterile form and with instructions for applying the tip to the main body of an apparatus of the invention.

Kits of the invention may include any of the components provided herein (e.g., tips, reservoir containing modules, and cables) in any number. Kits may also have or be designed to have any of the configurations described herein.

Ablation Method and Treatment

Any of the apparatuses, systems, kits, and methods of the invention may be used for non-thermal tissue ablation. The apparatuses, systems, kits, and methods of the invention can be applied to treat one or more skin regions. In particular embodiments, these regions are treated with one or more procedures to improve skin appearance. Accordingly, the apparatuses, systems, kits, and methods herein can be useful for skin rejuvenation (e.g., removal of pigment, veins (e.g., spider veins or reticular veins), glands (e.g., sebaceous glands or sweat glands), hair follicles, and/or vessels in the skin) or for treating acne, allodynia, blemishes, ectopic dermatitis, hyperpigmentation, hyperplasia (e.g., lentigo or keratosis), loss of translucency, loss of elasticity, melasma (e.g., epidermal, dermal, or mixed subtypes), photodamage, rashes (e.g., erythematous, macular, papular, and/or bullous conditions), psoriasis, rhytides (or wrinkles, e.g., lateral canthal lines ("crow's feet"), age-related rhytides, sun-related rhytides, or heredity-related rhytides), sallow color, scar contracture (e.g., relaxation of scar tissue), scarring (e.g., due to acne, surgery, or other trauma), skin aging, skin contraction (e.g., excessive tension in the skin), skin irritation/sensitivity, skin laxity (e.g., loose or sagging skin or other skin irregularities), striae (or stretch marks), tattoo removal, vascular lesions (e.g., angioma, erythema, hemangioma, papule, port wine stain, rosacea, reticular vein, or telangiectasia), or any other unwanted skin irregularities.

Such treatments may be applied to any part or parts of the body, including the face (e.g., eyelid, cheeks, chin, forehead, lips, or nose), neck, chest (e.g., as in a breast lift), arms, hands, legs, abdomen, and/or back. Accordingly, the apparatuses, systems, kits, and methods of the invention can be configured to be useful for treatment of regions of the body with different sizes and geometries. For example, tips having ablation member arrays of different sizes, geometries, and arrangements may be included in a kit of the invention to allow for treatment of both facial (e.g., with tips having small arrays of regular or irregular geometries) and abdominal regions (e.g., with tips having large arrays of regular geometries). Such arrangements and configurations can include any useful shape (e.g., linear, curved, or stellate), size, geometry, depth, and/or other characteristics.

Treatment methods may involve forming a plurality of ablated tissue portions by contacting the ablation members (e.g., needles, such as hollow coring needles) of the tip to the skin of a subject and removing the ablated tissue portions from the skin. Penetration into the skin by the ablation members may create small wounds (e.g., microwounds) and/or holes and so effectively reduce tissue volume and/or improve tissue quality upon healing. For example, forming a series of ablated tissue portions (e.g., ablation of about 10% of the total skin area) and corresponding holes in a high laxity skin region and subsequent compression of the skin region to close the holes may promote the growth of new skin (e.g., improved tissue). Healing of the tissue under compression allows for the existing tissue to span the gap introduced by the removal of an ablated tissue portion, thereby reducing the skin volume and area (e.g., by tightening the skin).

Prior to contacting the skin with the ablation members, the skin may be gripped, lifted, and/or positioned to facilitate treatment. For example, tensioning rods may be used to apply a compressive force to the skin as provided in FIG. 10. Such a force may be applied throughout the treatment.

Any beneficial area or volumetric fraction of the skin region can be removed. For example, between about 5% to about 70% of tissue may be removed (e.g., as described herein). In some preferred embodiments, about 10% of the treatment area is removed.

Tissue can be removed from the treatment region with various hole density (i.e., the number of holes per unit area) corresponding to the number and geometry of ablation members included in the tip or tips used and the number of applications of the tip or tips to the treatment region. Different hole densities may be desirable for different regions of skin and for different conditions and may be achieved using different tips. For example, 15 holes corresponding to the size of a 19 gauge needle and their corresponding ablated tissue portions may be created in a given treatment area by actuation of a single 19 gauge needle 15 times, or by actuating an array having five 19 gauge needles three times. Spacing the same number of holes further apart will result in a lower hole density per unit area. For example, 15 holes may be created within a 0.5 mm by 0.3 mm region or within a 5 mm by 3 mm region. In particular embodiments, apparatuses, systems, kits, and methods of the invention (e.g., any described herein) are configured to provide from about 10 to about 10000 ablated tissue portions per $cm^2$ area of the skin region (e.g., as described herein). The array of holes created by ablation of the skin may be created in any beneficial pattern within the skin region. For example, a higher density and/or smaller spacing of tissue portions and corresponding holes can be ablated in the skin in the center of a pattern or in thicker portions of the skin. A pattern may be random or include one or more of staggered rows and/or blocks, parallel rows and/or blocks, a circular pattern, a spiral pattern, a square or rectangular pattern, a triangular pattern, a hexagonal pattern, a radial distribution, or a combination of one or more such patterns. The pattern may arise from the use of one or more tips with one or more configurations and numbers of ablation members applied in any ordered or disordered manner. Modifications to the average length, width, shapes, and/or other characteristics of one or more ablation members used to treat a skin region may also result in a specific pattern of holes in the skin. Such patterns may be optimized to promote unidirectional, non-directional, or multidirectional contraction or expansion of skin (e.g., in the x-direction, y-direction, x-direction, x-y plane, y-z plane, x-z plane, and/or xyz-plane), such as by modifying the average length, depth, width, density, orientation, and/or spacing between ablations.

Any useful portion of the skin and/or underlying structures (e.g., SMAS) can be ablated. Tissue portions created by penetration into the skin with the ablation members of a tip may include epidermal tissue, dermal tissue, and/or cells or tissue proximal to the dermal/fatty layer boundary (e.g., stem cells). In some embodiments, a tissue portion may have a length that corresponds to a typical total depth of the skin layer (e.g., epidermal and dermal layers). The total depth of the epidermal and dermal layers may vary based on the region and age of the body being treated. In some instances, the depth of the epidermal layer is between about 0.01 mm to 0.2 mm, and/or the depth of the dermal layer is between about 0.3 mm to 6.0 mm. The total depth of the skin layer (e.g., epidermal and dermal layers) may be between about 0.3 mm and 6.2 mm, corresponding to a possible tissue portion having a length between about 0.3 mm and 6.2 mm (e.g., between about 0.3 mm and 0.6 mm, 0.3 mm and 0.9 mm, 0.3 mm and 1.5 mm, 0.3 mm and 2.0 mm, 0.3 mm and 2.5 mm, 0.3 mm and 3.0 mm, 0.3 mm and 3.5 mm, 0.3 mm and 4.0 mm, 0.3 mm and 4.5 mm, 0.3 mm and 5.0 mm, 0.3 mm and 5.5 mm, 0.3 mm and 6.0 mm, 0.3 mm and 6.2 mm, 0.6 mm and 0.9 mm, 0.6 mm and 1.5 mm, 0.6 mm and 2.0 mm, 0.6 mm and 2.5 mm, 0.6 mm and 3.0 mm, 0.6 mm and 3.5 mm, 0.6 mm and 4.0 mm, 0.6 mm and 4.5 mm, 0.6 mm and 5.0 mm, 0.6 mm and 5.5 mm, 0.6 mm and 6.0 mm, 0.6 mm and 6.2 mm, 0.9 mm and 1.5 mm, 0.9 mm and 2.0 mm, 0.9 mm and 2.5 mm, 0.9 mm and 3.0 mm, 0.9 mm and 3.5 mm, 0.9 mm and 4.0 mm, 0.9 mm and 4.5 mm, 0.9 mm and 5.0 mm, 0.9 mm and 5.5 mm, 0.9 mm and 6.0 mm, 0.9 mm and 6.2 mm, 1.5 mm and 2.0 mm, 1.5 mm and 2.5 mm, 1.5 mm and 3.0 mm, 1.5 mm and 3.5 mm, 1.5 mm and 4.0 mm, 1.5 mm and 4.5 mm, 1.5 mm and 5.0 mm, 1.5 mm and 5.5 mm, 1.5 mm and 6.0 mm, 1.5 mm and 6.2 mm, 2.0 mm and 2.5 mm, 2.0 mm and 3.0 mm, 2.0 mm and 3.5 mm, 2.0 mm and 4.0 mm, 2.0 mm and 4.5 mm, 2.0 mm and 5.0 mm, 2.0 mm and 5.5 mm, 2.0 and 6.0 mm, 2.0 mm and 6.2 mm, 2.5 mm and 3.0 mm, 2.5 mm and 3.5 mm, 2.5 mm and 4.0 mm, 2.5 mm and 4.5 mm, 2.5 mm and 5.0 mm, 2.5 mm and 5.5 mm, 2.5 mm and 6.0 mm, 2.5 mm and 6.2 mm, 3.0 mm and 3.5 mm, 3.0 mm and 4.0 mm, 3.0 mm and 4.5 mm, 3.0 mm and 5.0 mm, 3.0 mm and 5.5 mm, 3.0 and 6.0 mm, 3.0 mm and 6.2 mm, 3.5 mm and 4.0 mm, 3.5 mm and 4.5 mm, 3.5 mm and 5.0 mm, 3.5 mm and 5.5 mm, 3.5 mm and 6.0 mm, 3.5 mm and 6.2 mm, 4.0 mm and 4.5 mm, 4.0 mm and 5.0 mm, 4.0 mm and 5.5 mm, 4.0 and 6.0 mm, 4.0 mm and 6.2 mm, 4.5 mm and 5.0 mm, 4.5 mm and 5.5 mm, 4.5 and 6.0 mm, 4.5 mm and 6.2 mm, 5.0 mm and 5.5 mm, 5.0 mm and 6.0 mm, 5.0 mm and 6.2 mm, 5.5 mm and 6.0 mm, 5.5 mm and 6.2 mm, or 6.0 mm and 6.2 mm). In some instances, the average total depth of the skin layer (e.g., epidermal and dermal layers) may be about 1.5 mm, about 3 mm, or about 6 mm.

In some instances, it may be desirable to configure apparatuses, systems, kits, and methods of the invention to provide one or more tissue portions that do not include significant amounts of subcutaneous tissue, or, in other instances, to provide tissue portions that do include significant amounts of subcutaneous tissue. Electronic and/or physical mechanisms may be used to control the depth of an ablation (i.e., the penetration into the skin by the ablation members) and the corresponding size of an ablated tissue portion and hole. For example, an apparatus may include one or more stop arrangements (e.g., one or more collars and/or sleeves); one or more scroll wheels, buttons, dials, toggles, or other components to physically retract the skin-penetrating component; a vibrating arrangement (e.g., a piezoelectric element, a solenoid, a pneumatic element, or a hydraulic element) that mechanically couples to at least one ablation member (e.g., to promote insertion of one or more ablation members into the skin region, such as by providing an amplitude of vibration in the range of about 50-500 μm or by providing a frequency of the induced vibrations to be between about 10 Hz and about 10 kHz); a z-actuation mechanism (e.g., a pneumatic, electromagnetic, or piezo-electric actuator or a motor with a cam); and/or one or more sensors (e.g., force sensors, optical sensors, laser fibers, photodetectors, and/or position sensors) in communication with one or more needles, pins, actuators, valves, pressure generating sources, and/or user interfaces to detect the position of ablation members and/or the position of the apparatus relative to the treated skin portion.

Healing of Skin Regions after Removal of Ablated Tissue Portions

Figure 16:
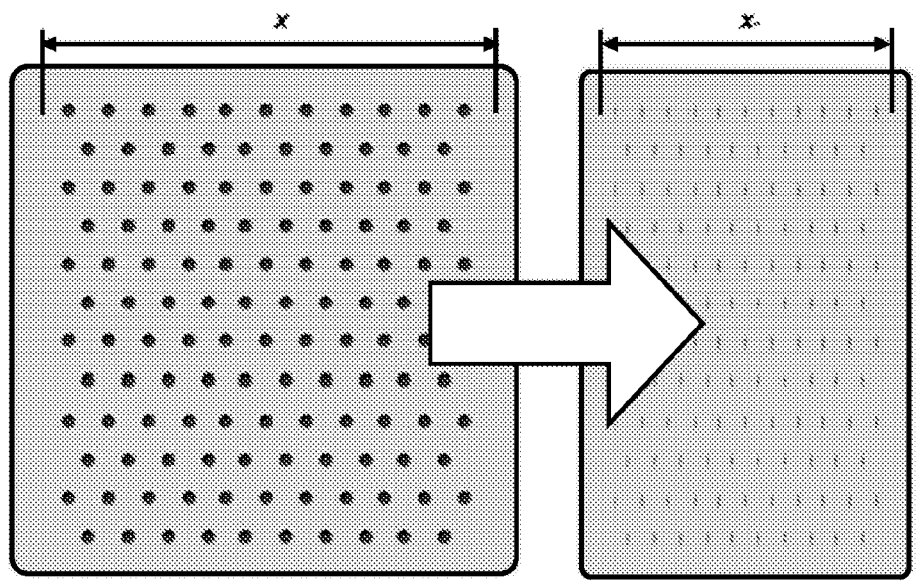
FIG. 16 is a schematic depicting reduction of tissue in a treated area by closure of ablations in a preferred direction.

A compressive wound dressing may be applied after ablation to promote skin tightening. A hole created by penetration into the skin with the ablation members of the tip may be closed with a suture, staple, dressing, tunable dressing, glue, sealant, and/or other compression retaining devices. Such dressings may be applied in the proximity of the treatment zone or at a distant site provided that it conveys the appropriate mechanical force on the treatment site (e.g., by gluing the surrounding area into a compressed state, which then confers compression to the treated area). Wound dressings may be applied in a preferred direction to promote healing in a particular direction or along particular axes (FIG. 16). For example, healing may be engineered to occur along Langer lines. In some embodiments, a photo-chemical agent may be applied to the tissue and the tissue then irradiated with visible light to produce a seal.

EXAMPLES

Example 1: Stamping Mechanism

Figure 17:
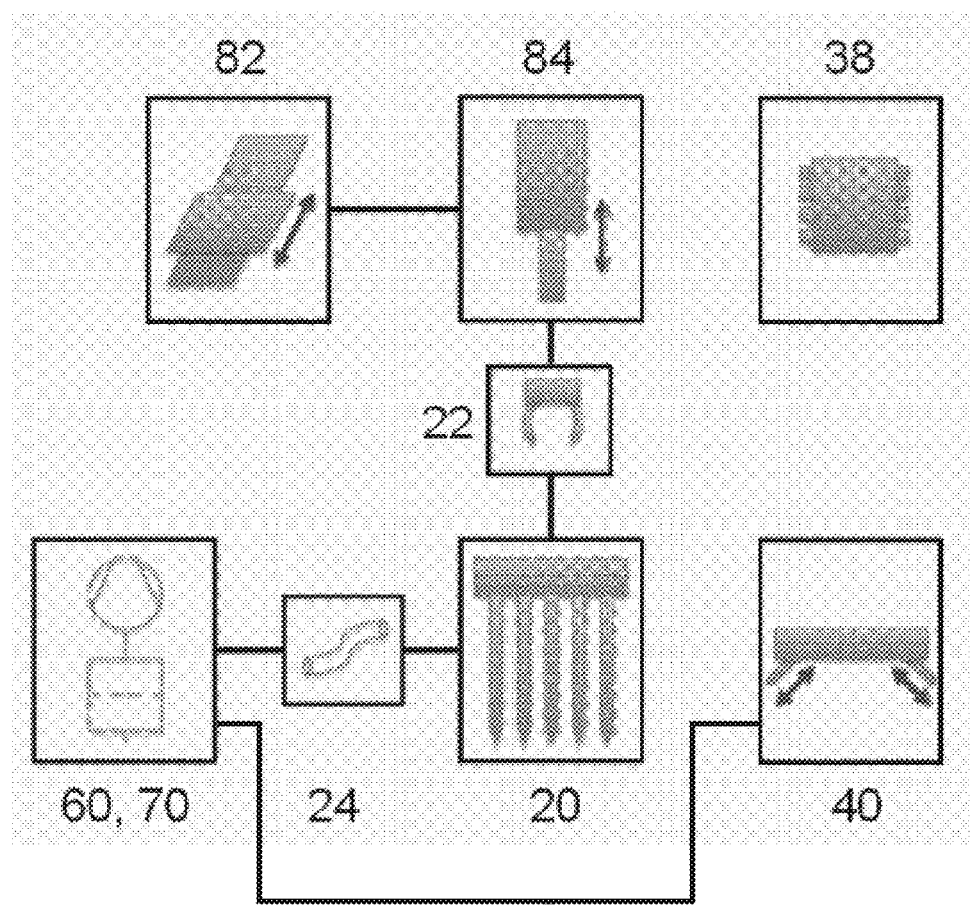
FIG. 17 is a schematic depicting the architecture of a "stamping" device. The "stamping" device of the invention includes z-actuator 84, x-actuator 82, control electronics 38, array gripper 22, skin-penetrating component 20, tubing 24, reservoir for waste collection 60, vacuum source 70, and skin positioning apparatus 40.

In one example, a system of the invention includes the apparatus, a reservoir for collecting waste materials (e.g., tissue, blood, and/or interstitial fluids), a low pressure generating source, a skin gripper and/or lifter, a base unit, and a cable coupling the apparatus and the base unit. FIG. 17 shows a schematic representation of the components of this system. The handheld apparatus has a separate module disposed between the tip and the main body that includes reservoir 60 for waste collection. This module is detachably attachable to both the tip and the main body via a quick-release mechanism. Both the body of the tip and the waste module are made of plastic materials and are meant to be disposed of after a single use (e.g., after treatment of a distinct region of the skin of a subject) either as a single unit or as two separated components.

Skin-penetrating component 20 of the tip includes an array of hollow, cylindrical, metallic coring needles that are sharpened and open at their tips. The needles are coupled to a substrate and are further coupled to plastic tubing 24 that establishes fluid communication between the needles, reservoir, and low pressure generating source 70 of the system. This low pressure generating source is a scroll-type oil-free vacuum pump disposed in the base unit and separated from the reservoir and needles by a series of filters (e.g., stainless steel 0.2 µm membrane filters) to prevent aspiration of waste materials into the device. A solenoid valve disposed in the main body of the apparatus allows for separation of the treatment site from the vacuum source without ceasing power supply to the vacuum pump. A user interface disposed on the main body of the apparatus permits a user to activate actuation mechanisms to drive needles into and across the skin as well as to activate the solenoid valve and thus provide suction to the treatment site. The user interface also indicates the number and configuration of needles in the array of the tip, the level of vacuum being supplied to the system and the powered status of the vacuum, the powered status of the apparatus, the mode of operation, and other useful information. The user interface of the main body receives signal from a user interface of the base unit via a cable coupling the apparatus and the base unit, and changes made in one user interface are reflected in the other. The user interface of the base unit includes a touch screen as well as various buttons to provide power to the vacuum source; actuation, translation, and position detection mechanisms of the apparatus; and control electronics 38. The base unit receives electrical power from a wall unit and transmits power to components of the system via the cable coupling the base unit and the apparatus.

The main body includes the actuation mechanisms to drive needle action. Electromagnetic z-actuator 84 controls the timing and depth of needle penetration as well as the withdrawal of the needles, while electromagnetic x-actuator 82 controls the movement of the apparatus across the treatment surface. Separate buttons disposed on the main body operate the z- and x-actuators. The actuation mechanisms may be configured by the user interface of the base unit (e.g., the depth of penetration into the skin by the needles may be selected from a range of options; controlling the penetration depth may involve supplying electrical signals with different amplitudes to the actuator). Array gripper 22 provides a mechanical connection between the needle array and the actuation mechanisms.

Prior to treatment, the skin region may be sterilized, plucked, shaved, massaged, heated, cooled, treated with chemicals and/or bioactive agents, and/or otherwise prepared. The region of skin is positioned using skin positioning apparatus 40 that utilizes tensioning rods to apply a compressive force. System components are supplied with power, and the desired operating parameters are selected on either user interface (e.g., the depth of penetration by the needles). The skin-penetrating component is placed upon the surface of the skin and the z-actuator is activated to cause the needles to penetrate into the skin. Before the needles are retracted, the solenoid valve is activated and vacuum applied to the treatment area, removing tissue (e.g., ablated tissue portions) from within the needle and waste materials from the area and depositing tissue, blood, interstitial fluids, and/or any other debris within the reservoir. After the valve is closed, activation of the z-actuator causes the needles to withdraw from the skin. Subsequent activation of the x-actuator moves the apparatus to an adjacent treatment area, where the actions may be repeated. The amount of movement caused by activation of the x-actuator depends on the size of the area but may be selected to be as far as 50 mm. The tip and/or reservoir may be replaced at any point during the treatment, though preferably after the treatment of a given region is complete. The system may be configured to remove between about 5% and about 70% of tissue from the treatment area. For example, the system may be configured to remove about 10% of tissue from the treatment area. Accordingly, the system may be configured to produce a particular arrangement, density, and geometry of ablated tissue portions.

Figure 18A:
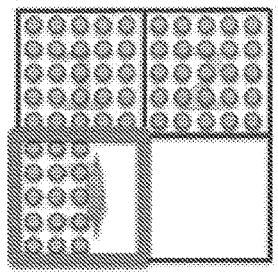
FIGS. 18A, 18B, and 18C illustrate operation of a device with a "stamping" architecture (18A) and automatic (18B) and manual (18C) operation of a device with a "brushing" architecture.

FIG. 18A demonstrates this treatment method schematically. In the illustration, adjacent areas are treated with a system including a 2-dimensional needle array. This treatment method may be thought of as a "stamping" mechanism.

Example 2: Brushing Mechanism

Figure 18B:
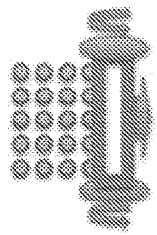
Figure 18C:
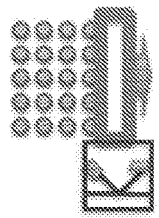
Figure 19:
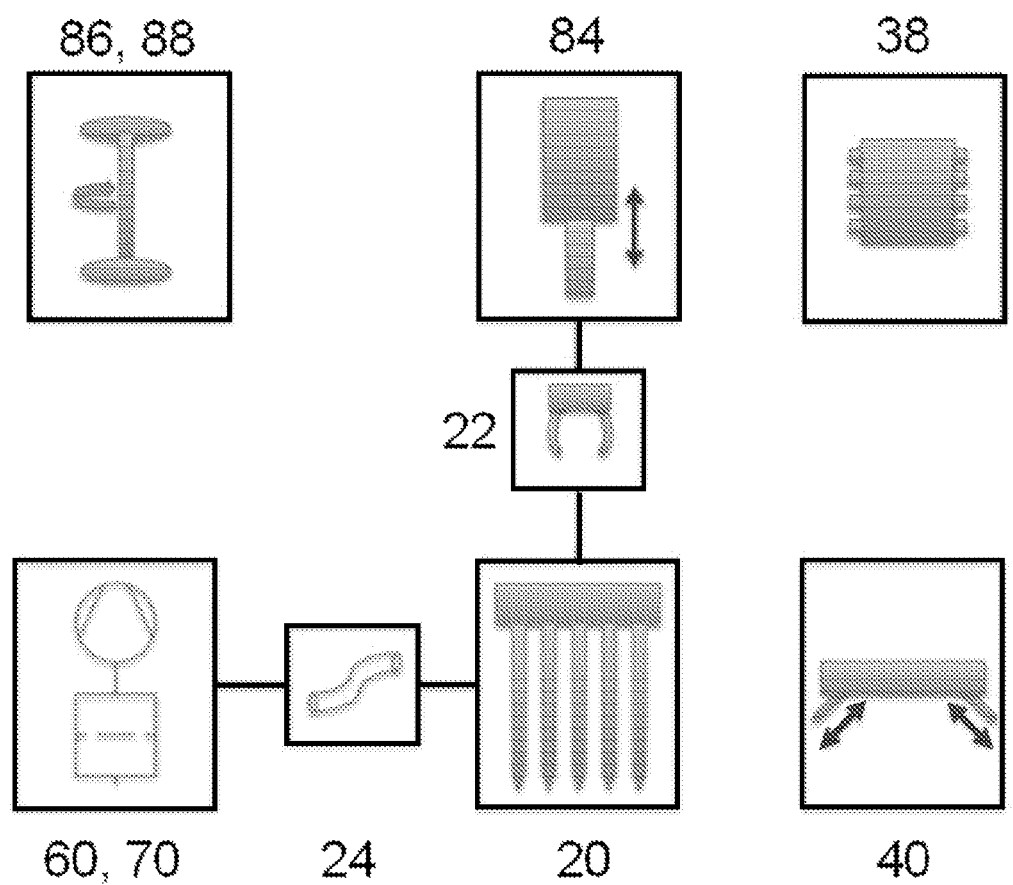
FIG. 19 is a schematic depicting the architecture of a "brushing" device. The "brushing" device of the invention includes z-actuator 84, translating mechanism 86, position detection mechanism 88, control electronics 38, array gripper 22, skin-penetrating component 20, tubing 24, reservoir for waste collection 60, vacuum source 70, and skin positioning apparatus 40.

In a second example, a system of the invention may have substantially the same components and configuration as a system designed to operate with a "stamping mechanism" but may include a translation mechanism in place of an x-actuator. Such a system is schematically represented in FIG. 19. In this system, translation mechanism 86 features driving wheels which can be detachably coupled to the tip. The translation mechanism may be nearly continuously activated by means of a button disposed on the main body such that action of the device resembles a "brushing" motion (FIG. 18B). The system operator may alternatively select to manually translate the device across the skin surface. Manual translation may be particularly useful in skin regions with small or irregular geometries such as on the face. The system further includes a position detection mechanism (i.e., an optical tracking mechanism) to assist the operator in providing even treatment across a skin surface (FIG. 18C). For example, the position detection mechanism may facilitate automatic operation of the apparatus by detecting the distance between the previous needle insertion and the current device position and activating penetration into the skin by the needles when the device has reached the desired position. The system may also include a camera configured to transmit images to a viewing station such as a computer of the base unit. The camera is disposed on the main body of the apparatus and assists the operator in selecting regions for treatment and translating the apparatus across the region.

Example 3: Treatment of Skin Laxity and/or Rhytides in the Face

An apparatus or system of the invention may be used to administer treatment to the skin of a subject. Treatment may be performed outside of an operating room environment, thereby minimizing the cost of treatment.

The system used for treatment of the subject may be any of those described herein. For example, the system may be that of Example 1. For treatment of skin laxity in the face, a tip with a rectangular array of, e.g., 50 metallic coring needles may be selected for application to a treatment area of about 4 mm by about 9 mm. The selected needles may be 24 gauge needles and may be affixed to the tip structure by plastic molded around one end of each needle. The other needle ends may be, e.g., sharpened to fine points. The minimum distance between any two needles may be about 0.9 mm. With this tip, about 10% of the area of skin may be ablated upon activation of the device. The needles may be configured to penetrate about 2 mm into the skin. Thus, with this tip, ablated tissue portions may have volumes of about 0.2 mm$^3$.

As described above, the skin area may first be sterilized, treated with chemicals, and/or otherwise prepared for treatment. The tensioning rods of the optional skin positioning apparatus may subsequently be applied to the skin to position the skin and facilitate ease and effectiveness of device operation. Treatment may proceed with the driving of the needles into the skin by activation of the z-actuator, removal of waste materials by activation of suction, removal of the needles from the skin, and translation of the device to an adjacent region for treatment. When sufficient tissue area has been treated, the device components may be powered off, any residual fluids and/or debris are removed, the skin surface and/or holes are cleaned and/or flushed with fluid, and a compressive wound dressing applied to the skin to cause the holes to close in a preferred direction. The tip and the separate reservoir module may be disposed of, and other components of the system may be sterilized.

The treatment may be rapid (e.g., less than 30 minutes), minimizing patient downtime and allowing treatment to be carried out as an outpatient procedure. Within days, a reduction in skin laxity and/or rhytides in the treatment area may be observed. The treatment should be more effective at reducing skin laxity, inducing skin tightening, and/or rejuvenating skin (i.e., improving skin architecture, reducing wrinkles) than energy-based skin treatment methods, such as laser, ultrasound, and radio frequency methods, while requiring similar or reduced patient downtime and environmental/training requirements. In certain applications and configurations, the treatment may also allow deeper tissue ablation than is possible with lasers, for example, to permit the treatment of scars and the removal of sub-dermal tissue layers.

OTHER EMBODIMENTS

All publications, patent applications, and patents mentioned in this specification are herein incorporated by reference.

Various modifications and variations of the described apparatuses, systems, kits, and methods of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention are intended to be within the scope of the invention.

The invention claimed is:

1. An apparatus for non-thermal tissue ablation comprising:
   a) a main body configured for handheld operation, and
   b) a tip comprising a skin-penetrating component comprising one or more sharpened hollow coring needles, wherein said tip is detachably attached to said main body and wherein each of said one or more sharpened hollow coring needles is configured to produce a plurality of ablated tissue portions by penetrating into and retracting from skin;
   the apparatus further comprising a positioning apparatus for positioning skin, wherein the positioning apparatus is configured to grip and/or lift the skin;
   wherein the positioning apparatus is or comprises one or more vacuum grippers; and
   the apparatus further comprising a translating mechanism disposed in the main body for driving said one or more sharpened hollow coring needles across a region of the skin in one or two directions that are orthogonal to a longitudinal movement of the hollow coring needles penetrating into the skin and retracting the hollow coring needles from the skin;
   wherein the positioning apparatus is configured to ensure that the non-thermal tissue ablation occurs at a desired location at the region of the skin by the needles translated by the translating mechanism.

2. The apparatus of claim 1, wherein said one or more sharpened hollow coring needles are configured to be in fluid communication with a pressure generating source.

3. The apparatus of claim 2, wherein said pressure generating source is capable of producing a pressure of about 0.1 kPa to about 6.0 kPa.

4. The apparatus of claim 3, wherein said pressure generating source produces vacuum.

5. The apparatus of claim 2, wherein said pressure generating source is separate from said apparatus.

6. The apparatus of claim 1, wherein the one or more sharpened hollow coring needles comprise two or more sharpened hollow coring needles arranged in a 1-dimensional array.

7. The apparatus of claim 1, wherein the one or more sharpened hollow coring needles comprise three or more sharpened hollow coring needles arranged in a 2-dimensional array.

8. The apparatus of claim 1, wherein one or more sharpened hollow coring needles comprise 1-100 sharpened hollow coring needles.

9. The apparatus of claim 1, wherein one or more sharpened hollow coring needles comprise two or more sharpened hollow coring needles that are spaced about 0.1 mm to about 5 mm apart.

10. The apparatus of claim 1, wherein said one or more sharpened hollow coring needles are 19-26 gauge needles.

11. The apparatus of claim 10, wherein said one or more sharpened hollow coring needles are 22 or 24 gauge needles.

12. The apparatus of claim 1, wherein said apparatus is configured to provide an ablated tissue portion having a change in width as a function of depth.

13. The apparatus of claim 12, wherein the width to depth ratio of said ablated tissue portion is between about 1:0.3 and about 1:75.

14. The apparatus of claim 1, wherein said one or more sharpened hollow coring needles have a width at their widest points of about 0.01 mm to about 2 mm.

15. The apparatus of claim 1, wherein said apparatus is configured to remove about 5% to about 70% of tissue within a treatment area.

16. The apparatus of claim 1, wherein said apparatus is configured to remove about 5% of tissue within a treatment area.

17. The apparatus of claim 1, further comprising an actuation mechanism for driving penetration into skin by said sharpened hollow coring needles, wherein said actuation mechanism is mechanically or electrically coupled to said one or more sharpened hollow coring needles.

18. The apparatus of claim 17, wherein said actuation mechanism is configured to drive penetration into the skin by said one or more sharpened hollow coring needles to a depth of about 0.1 mm to about 15 mm.

19. The apparatus of claim 18, wherein said actuation mechanism is configured to drive penetration into the skin by said one or more sharpened hollow coring needles to a depth of about 2 mm to about 5 mm.

20. The apparatus of claim 17, wherein said actuation mechanism is configured to drive penetration into the skin by said one or more sharpened hollow coring needles with a force of about 0.5 N to about 20 N per sharpened hollow coring needle.

21. The apparatus of claim 1, further comprising a position detection mechanism.

22. The apparatus of claim 1, further comprising a release mechanism for detaching said tip.

23. The apparatus of claim 1, further comprising a reservoir for collecting waste materials.

24. The apparatus of claim 23, wherein the apparatus is coupled to a base unit.

25. The apparatus of claim 24, wherein said base unit comprises said reservoir.

26. The apparatus of claim 24, wherein said base unit comprises a pressure generating source.

27. The apparatus of claim 24, wherein said base unit comprises a user interface.

28. An apparatus for non-thermal tissue ablation comprising:
a) a main body configured for handheld operation;
b) a tip comprising a skin-penetrating component comprising one or more sharpened hollow coring needles, wherein said tip is detachably attached to said main body and wherein each of said one or more sharpened hollow coring needles is configured to produce a plurality of ablated tissue portions by penetrating into and retracting from skin;
c) a pressure generating source in fluid communication with said one or more sharpened hollow coring needles configured to produce vacuum or suction to convey the ablated tissue portions through said one or more sharpened hollow coring needles;
d) a reservoir for collecting waste materials configured to be in fluid communication with the one or more sharpened hollow coring needles; and
e) a translating mechanism disposed in the main body for driving said one or more sharpened hollow coring needles across a region of the skin in one or two directions that are orthogonal to a longitudinal movement of the hollow coring needles penetrating into the skin and retracting the hollow coring needles from the skin.

* * * * *